United States Patent
Verstreken et al.

(10) Patent No.: US 11,332,526 B2
(45) Date of Patent: May 17, 2022

(54) TARGETING SYNAPTOGYRIN-3 IN TAUOPATHY TREATMENT

(71) Applicants: VIB VZW, Ghent (BE); KATHOLIEKE UNIVERSITEIT LEUVEN, K.U.LEUVEN R&D, Leuven (BE)

(72) Inventors: Patrik Verstreken, Blanden (BE); Joseph McInnes, Leuven (BE); Lujia Zhou, Leuven (BE)

(73) Assignees: VIB VZW, Ghent (BE); Katholieke Univeriteit Leuven, K.U. Leuven R&D, Leuven (BE)

( * ) Notice: Subject to any disclaimer, the term of this patent is extended or adjusted under 35 U.S.C. 154(b) by 0 days.

(21) Appl. No.: 16/631,400

(22) PCT Filed: Jul. 16, 2018

(86) PCT No.: PCT/EP2018/069228
§ 371 (c)(1),
(2) Date: Jan. 15, 2020

(87) PCT Pub. No.: WO2019/016123
PCT Pub. Date: Jan. 24, 2019

(65) Prior Publication Data
US 2020/0216531 A1 Jul. 9, 2020

(30) Foreign Application Priority Data
Jul. 17, 2017 (EP) .................................. 17181659

(51) Int. Cl.
| C07K 16/28 | (2006.01) |
| A61K 38/46 | (2006.01) |
| C12N 15/113 | (2010.01) |
| C12N 15/115 | (2010.01) |
| G01N 33/544 | (2006.01) |

(52) U.S. Cl.
CPC ............ *C07K 16/28* (2013.01); *A61K 38/465* (2013.01); *C12N 15/115* (2013.01); *C12N 15/1138* (2013.01); *G01N 33/544* (2013.01); *C07K 2317/34* (2013.01); *C07K 2317/76* (2013.01); *C12N 2310/11* (2013.01); *C12N 2310/14* (2013.01); *G01N 2500/04* (2013.01)

(58) Field of Classification Search
None
See application file for complete search history.

(56) References Cited

FOREIGN PATENT DOCUMENTS

| WO | 2007140975 A1 | 12/2007 |
| WO | 2008020435 A2 | 2/2008 |

OTHER PUBLICATIONS

Belizaire "Characterization of Synaptogyrin 3 as a New Synaptic Vesicle Protein" The Journal of Comparative Neurology 470:266-281 (Year: 2004).*
Liu, et al., "Co-immunoprecipitation with Tau Isoform-specific Antibodies Reveals Distinct Protein Interactions and Highlights a Putative Role for 2N Tau in Disease," Journal of Biological Chemistry, Apr. 8, 2016, vol. 291, No. 15, pp. 8173-8188.
PCT International Search Report and Written Opinion; Application No. PCT/EP2018/069228, filing date of Jul. 16, 2018, dated Sep. 25, 2018, 11 pages.

* cited by examiner

*Primary Examiner* — Adam Weidner
(74) *Attorney, Agent, or Firm* — Patent Law Works, LLP

(57) ABSTRACT

The invention relates to identification of synaptogyrin-3 as a target for treating or inhibiting progression of tauopathies or symptoms of tauopathies. In particular, synaptogyrin-3 inhibitors for use as a medicament in general, and for treating or inhibiting progression of tauopathies or symptoms of tauopathies are envisaged. The invention further relates to methods for identification of or for screening for inhibitors of synaptogyrin-3.

8 Claims, 14 Drawing Sheets

Figure 1:
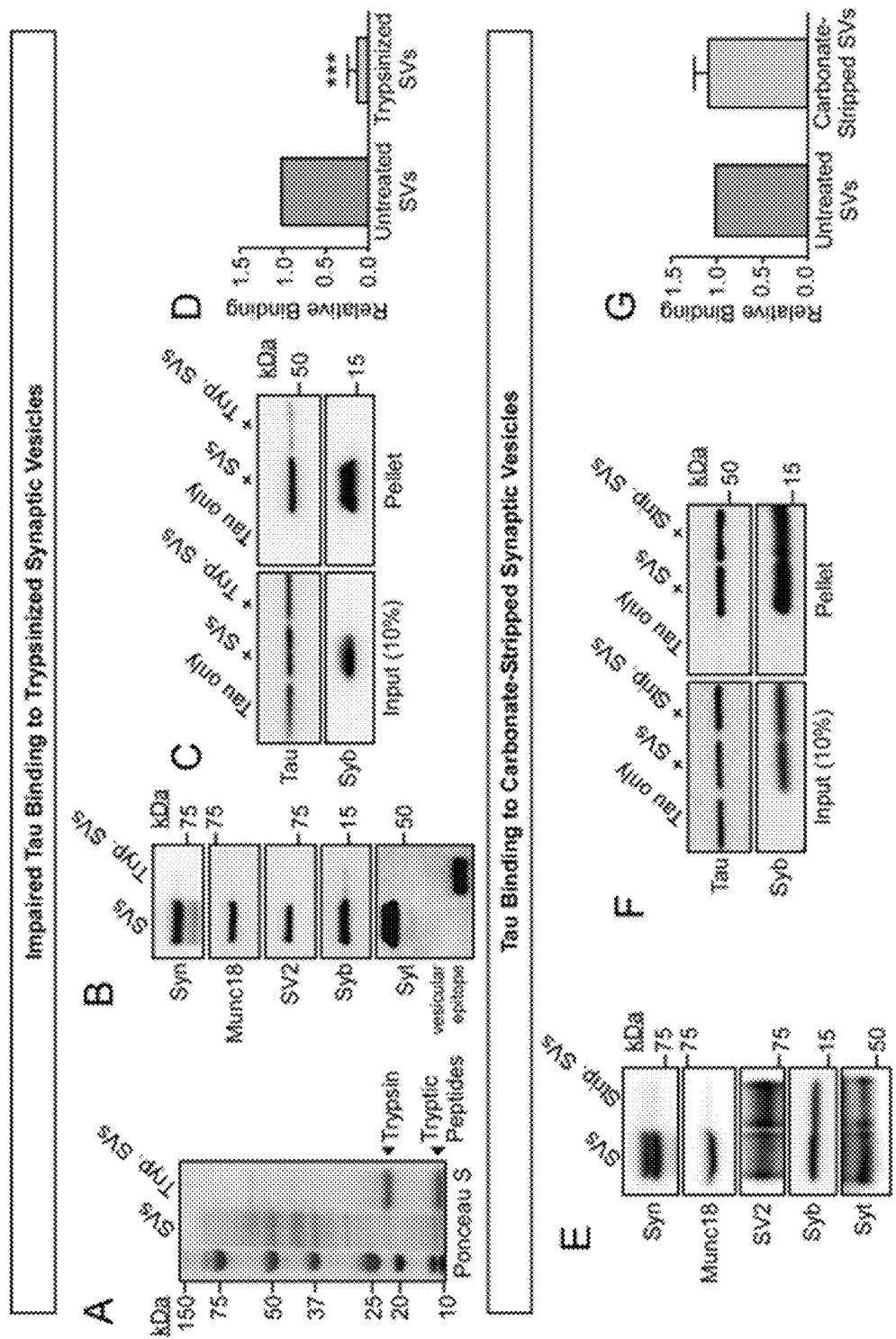
Figure 1:
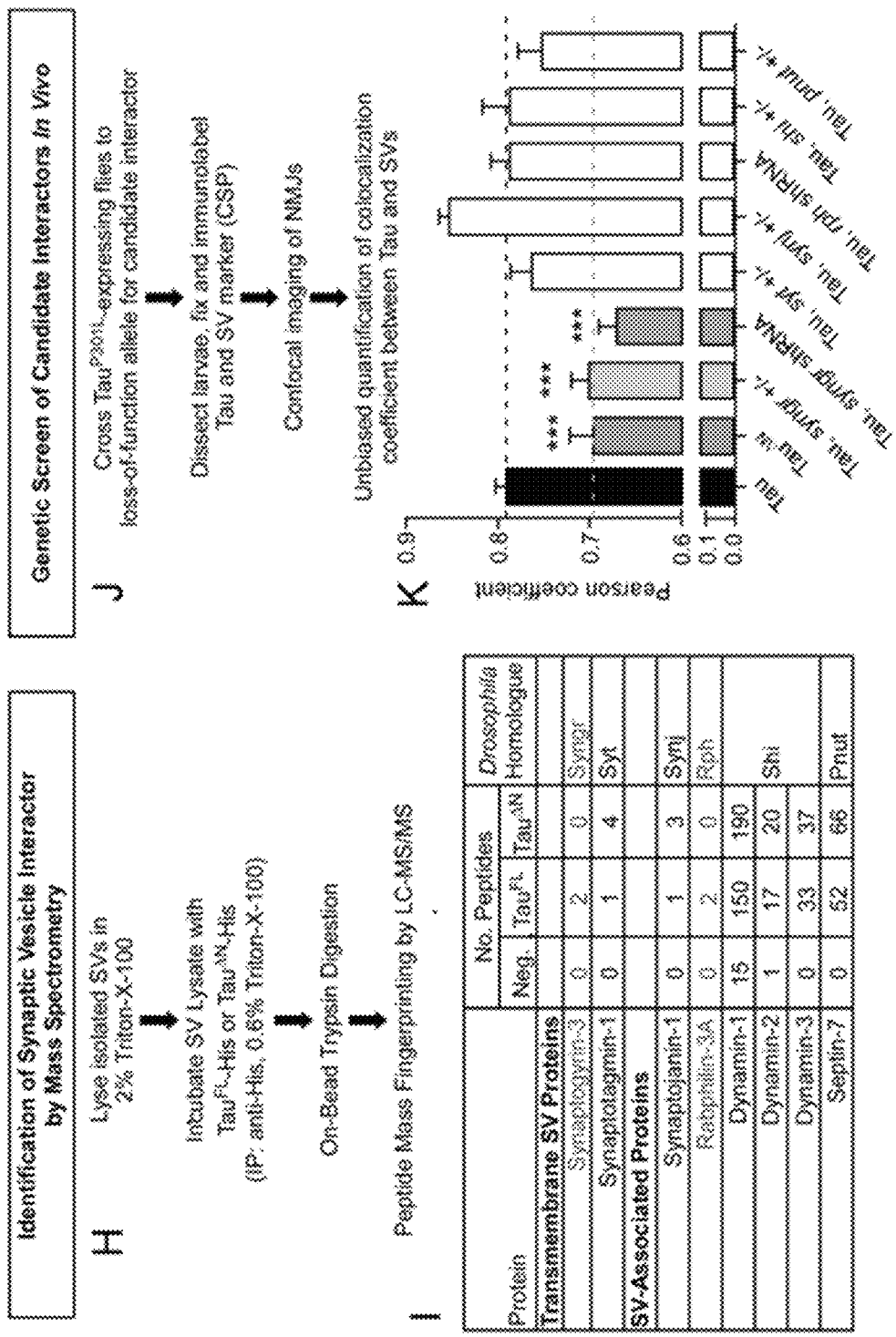

Specification includes a Sequence Listing.

SEQUENCE LISTING

```
<160> NUMBER OF SEQ ID NOS: 17

<210> SEQ ID NO 1
<211> LENGTH: 229
<212> TYPE: PRT
<213> ORGANISM: Homo sapiens

<400> SEQUENCE: 1

Met Glu Gly Ala Ser Phe Gly Ala Gly Arg Ala Gly Ala Ala Leu Asp
1               5                   10                  15

Pro Val Ser Phe Ala Arg Arg Pro Gln Thr Leu Leu Arg Val Ala Ser
                20                  25                  30

Trp Val Phe Ser Ile Ala Val Phe Gly Pro Ile Val Asn Glu Gly Tyr
            35                  40                  45
```

```
Val Asn Thr Asp Ser Gly Pro Glu Leu Arg Cys Val Phe Asn Gly Asn
 50                  55                  60
Ala Gly Ala Cys Arg Phe Gly Val Ala Leu Gly Leu Gly Ala Phe Leu
 65                  70                  75                  80
Ala Cys Ala Ala Phe Leu Leu Leu Asp Val Arg Phe Gln Gln Ile Ser
                 85                  90                  95
Ser Val Arg Asp Arg Arg Arg Ala Val Leu Leu Asp Leu Gly Phe Ser
                100                 105                 110
Gly Leu Trp Ser Phe Leu Trp Phe Val Gly Phe Cys Phe Leu Thr Asn
                115                 120                 125
Gln Trp Gln Arg Thr Ala Pro Gly Pro Ala Thr Thr Gln Ala Gly Asp
130                 135                 140
Ala Ala Arg Ala Ala Ile Ala Phe Ser Phe Phe Ser Ile Leu Ser Trp
145                 150                 155                 160
Val Ala Leu Thr Val Lys Ala Leu Gln Arg Phe Arg Leu Gly Thr Asp
                165                 170                 175
Met Ser Leu Phe Ala Thr Glu Gln Leu Ser Thr Gly Ala Ser Gln Ala
                180                 185                 190
Tyr Pro Gly Tyr Pro Val Gly Ser Gly Val Glu Gly Thr Glu Thr Tyr
                195                 200                 205
Gln Ser Pro Pro Phe Thr Glu Thr Leu Asp Thr Ser Pro Lys Gly Tyr
210                 215                 220
Gln Val Pro Ala Tyr
225

<210> SEQ ID NO 2
<211> LENGTH: 29
<212> TYPE: PRT
<213> ORGANISM: Homo sapiens

<400> SEQUENCE: 2

Met Glu Gly Ala Ser Phe Gly Ala Gly Arg Ala Gly Ala Ala Leu Asp
 1               5                  10                  15
Pro Val Ser Phe Ala Arg Arg Pro Gln Thr Leu Leu Arg
                 20                  25

<210> SEQ ID NO 3
<211> LENGTH: 14
<212> TYPE: PRT
<213> ORGANISM: Homo sapiens

<400> SEQUENCE: 3

Arg Phe Gln Gln Ile Ser Ser Val Arg Asp Arg Arg Arg Ala
 1               5                  10

<210> SEQ ID NO 4
<211> LENGTH: 61
<212> TYPE: PRT
<213> ORGANISM: Homo sapiens

<400> SEQUENCE: 4

Gln Arg Phe Arg Leu Gly Thr Asp Met Ser Leu Phe Ala Thr Glu Gln
 1               5                  10                  15
Leu Ser Thr Gly Ala Ser Gln Ala Tyr Pro Gly Tyr Pro Val Gly Ser
                 20                  25                  30
Gly Val Glu Gly Thr Glu Thr Tyr Gln Ser Pro Pro Phe Thr Glu Thr
                 35                  40                  45
Leu Asp Thr Ser Pro Lys Gly Tyr Gln Val Pro Ala Tyr
```

<210> SEQ ID NO 5
<211> LENGTH: 11
<212> TYPE: PRT
<213> ORGANISM: Artificial Sequence
<220> FEATURE:
<223> OTHER INFORMATION: TATp;protein

<400> SEQUENCE: 5

```
Tyr Gly Arg Lys Lys Arg Arg Gln Arg Arg Arg
1               5                   10
```

<210> SEQ ID NO 6
<211> LENGTH: 18
<212> TYPE: PRT
<213> ORGANISM: Artificial Sequence
<220> FEATURE:
<223> OTHER INFORMATION: MAP protein

<400> SEQUENCE: 6

```
Lys Leu Ala Leu Lys Leu Ala Leu Lys Ala Leu Lys Ala Ala Leu Lys
1               5                   10                  15

Leu Ala
```

<210> SEQ ID NO 7
<211> LENGTH: 16
<212> TYPE: PRT
<213> ORGANISM: Artificial Sequence
<220> FEATURE:
<223> OTHER INFORMATION: penetratin protein

<400> SEQUENCE: 7

```
Arg Gln Ile Lys Ile Trp Phe Gln Asn Arg Arg Met Lys Trp Lys Lys
1               5                   10                  15
```

<210> SEQ ID NO 8
<211> LENGTH: 112
<212> TYPE: PRT
<213> ORGANISM: Homo sapiens

<400> SEQUENCE: 8

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110
```

<210> SEQ ID NO 9
<211> LENGTH: 141
<212> TYPE: PRT
<213> ORGANISM: Homo sapiens

<400> SEQUENCE: 9

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg
    130                 135                 140

<210> SEQ ID NO 10
<211> LENGTH: 170
<212> TYPE: PRT
<213> ORGANISM: Homo sapiens

<400> SEQUENCE: 10

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg
                165                 170

<210> SEQ ID NO 11
<211> LENGTH: 36
<212> TYPE: DNA
<213> ORGANISM: Artificial Sequence
<220> FEATURE:
<223> OTHER INFORMATION: Primer

<400> SEQUENCE: 11
ggggacacgt ctccacggca tctcagcaat gtctcc        36

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
tcccccagcc tagaccacga gaat        24

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
caaatgttgc ttgtctggtg        20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
gtcagtcgag tgcacagttt        20

<210> SEQ ID NO 15
<211> LENGTH: 29
<212> TYPE: DNA
<213> ORGANISM: Artificial Sequence
<220> FEATURE:
<223> OTHER INFORMATION: syngr3A shRNA

<400> SEQUENCE: 15
gttcgtaggc ttctgtttcc tcaccaatc        29

<210> SEQ ID NO 16
<211> LENGTH: 29
<212> TYPE: DNA
<213> ORGANISM: Artificial Sequence
<220> FEATURE:
<223> OTHER INFORMATION: syngr3B shRNA

<400> SEQUENCE: 16
gagcctgccg cttcggcgtc gtactaggt        29

<210> SEQ ID NO 17
<211> LENGTH: 29
<212> TYPE: DNA
<213> ORGANISM: Artificial Sequence
<220> FEATURE:
<223> OTHER INFORMATION: scramble shRNA

<400> SEQUENCE: 17
gcactaccag agctaactca gatagtact        29

TARGETING SYNAPTOGYRIN-3 IN TAUOPATHY TREATMENT

FIELD OF THE INVENTION

The invention relates to identification of synaptogyrin-3 as a target for treating or inhibiting progression of tauopathies or symptoms of tauopathies. In particular, synaptogyrin-3 inhibitors for use as a medicament in general, and for treating or inhibiting progression of tauopathies or symptoms of tauopathies are envisaged. The invention further relates to methods for identification of or for screening for inhibitors of synaptogyrin-3.

BACKGROUND TO THE INVENTION

Tau pathology is associated with more than twenty neurodegenerative diseases, including Alzheimer's disease (Wang & Mandelkow 2016). Hyperphosphorylation or mutation of the microtubule-associated protein Tau is common to all of these diseases, collectively termed Tauopathies, and filamentous inclusions of hyperphosphorylated Tau are hallmark pathologies of Alzheimer's disease and other Tauopathies (Ballatore et al. 2007). Tau pathology is not merely a byproduct of other pathological pathways, but is a key mediator of neurotoxicity itself. In mouse models of familial Alzheimer's disease modeling excessive β-amyloid production, reduction of endogenous Tau ameliorates neurotoxicity and cognitive deficits (Roberson et al. 2007). Moreover, mutations in the Tau-encoding MAPT locus are causative of Frontotemporal dementia with parkinsonism linked to chromosome 17 (FTDP-17) (Hutton et al. 1998), and Tau duplications or haplotypes which have elevated Tau expression levels are strongly associated with dementia (Caffrey & Wade-Martins 2007; Le Guennec et al. 2016). These data support Tau as an executor of neuronal toxicity and degeneration in human disease.

Under physiological conditions, Tau is expressed in neurons and is bound to axonal microtubules. However, under pathological conditions, mutations in Tau (in FTDP-17) or abnormal phosphorylation of Tau (including sporadic Alzheimer's disease) decrease its microtubule binding affinity (Hong et al. 1998; Wang & Mandelkow 2016), leading to its dissociation from axonal microtubules and subsequent mislocalization to synapses (Spires-Jones & Hyman 2014; Tai et al. 2012; 2014). In Alzheimer's disease patients and animal models of Tauopathy, Tau mislocalization to synaptic compartments correlates well with the onset of synaptic dysfunction and cognitive decline (DeKosky & Scheff 1990; Spires-Jones & Hyman 2014; Yoshiyama et al. 2007). Importantly, synaptic defects are associated with soluble forms of Tau preceding Tau tangle formation in early disease stages (Koss et al. 2016), in agreement with studies showing that soluble Tau is sufficient to drive neuronal dysfunction in the absence of tangles (Crimins et al. 2012; Polydoro et al. 2014; Rocher et al. 2010; Santacruz et al. 2005). These findings highlight a key role of soluble Tau in perturbing synaptic function in early disease stages, which may contribute to subsequent synapse loss and neurodegeneration. However, the mechanisms by which Tau affects synaptic function remain underexplored.

Previous work has elucidated functions of pathological Tau in contributing to postsynaptic dysfunction on account of its mislocalization to dendritic spines and interference with glutamate receptor organization (Hoover et al. 2010; Ittner et al. 2010; Zhao et al. 2016). However, in addition to its post-synaptic localization, pathological Tau is also present in pre-synaptic compartments (Tai et al. 2014; 2012; Zhou et al. 2017), suggesting that Tau function at the presynapse may also contribute to disease pathogenesis. A presynaptic function of Tau is also pertinent given that neurodegeneration is thought to begin with loss of presynaptic terminals and proceed retrograde in a dyeing-back process (Yoshiyama et al. 2007), and in fly and rat neurons Tau can interfere with neurotransmitter release by associating with synaptic vesicles at presynaptic terminals (Zhou et al. 2017).

Bodily fluid levels of synaptogyrin-1, synaptogyrin-3 or variants thereof have been suggested as biomarkers for Alzheimer's disease (WO2007/140975).

SUMMARY OF THE INVENTION

In one aspect, the invention relates to a synaptogyrin-3 inhibitor for use as a medicament. In particular, it relates to a synaptogyrin-3 inhibitor for use in (a method for) treating or inhibiting progression of a tauopathic disorder or for use in (a method for) treating or inhibiting a symptom of a tauopathic disorder. Further, the synaptogyrin-3 can be specified as for instance being human synaptogyrin-3; and the synaptogyrin-3 inhibitor can be specified as an inhibitor specific to synaptogyrin-3 and even further specified as an inhibitor selected from the group consisting of an antisense oligonucleotide, a gapmer, a siRNA, a shRNA, an antisense oligonucleotide, a zinc-finger nuclease, a meganuclease, a TAL effector nuclease, a CRISPR-Cas effector, an antibody or a fragment thereof binding to synaptogyrin-3, an alpha-body, a nanobody, an intrabody, an aptamer, a DARPin, an affibody, an affitin, an anticalin, and a monobody.

One type of synaptogyrin-3 inhibitor for use (in a method) as described herein is an inhibitor capable of blocking binding of synaptogyrin-3 to the N-terminal region of the Tau protein. In relation hereto, such inhibitor is for example an antibody or fragment thereof, an alpha-body, a nanobody, an intrabody, an aptamer, a DARPin, an affibody, an affitin, an anticalin, or a monobody capable of binding to at least one intraneuronally exposed region of synaptogyrin-3, such as selected from the group consisting of SEQ ID NO:2, SEQ ID NO:3, SEQ ID NO:4, and variants thereof.

In any of the above, the tauopathic disorder may be selected from the group consisting of Alzheimer's disease, progressive supranuclear palsy (PSP), progressive supranuclear palsy-parkinsonism (PSP-P), Richardson's syndrome, argyrophilic grain disease, corticobasal degeneration Pick's disease, frontotemporal dementia with parkinsonism associated with chromosome 17 (FTDP-17), post-encephalitic parkinsonism, Parkinson's disease complex of Guam, Guadeloupean parkinsonism, Huntington disease, Down's syndrome, dementia pugilistica, familial British dementia, familial Danish dementia, myotonic dystrophy, Hallevorden-Spatz disease, Niemann Pick type C, chronic traumatic encephalopathy, tangle-only dementia, white matter tauopathy with globular glial inclusions, subacute sclerosing panencephalitis, SLC9A6-related mental retardation, non-Guamanian motor neuron disease with neurofibrillary tangles, neurodegeneration with brain iron accumulation, Gerstmann-Sträussler-Scheinker disease, frontotemporal lobar degeneration, diffuse neurofibrillary tangles with calcification, chronic traumatic encephalopathy, amyotrophic lateral sclerosis of Guam, amyotrophic lateral sclerosis and parkinsonism-dementia complex, prion protein cerebral amyloid angiopathy, and progressive subcortical gliosis.

In any of the above, the symptom of the tauopathic disorder may be selected from the group of mild cognitive impairment, dementia, cognitive decline, decline of motor function, oculomotor and bulbar dysfunction, synaptic dysfunction, neurotoxicity, neuronal degeneration, neuronal dysfunction, synapse loss, and amyloid deposition. The synaptic dysfunction may be further specified as pre-synaptic dysfunction.

In a further aspect, the invention relates to methods, in particular in vitro methods, for identifying or screening for synaptogyrin-3 inhibitors.

One such in vitro method for identifying a synaptogyrin-3 inhibitor may be comprising the steps of:
  i) providing synaptogyrin-3, or a fragment of synaptogyrin-3 comprising one or more of the intraneuronally exposed regions of synaptogyrin-3;
  ii) providing Tau protein, or a fragment of Tau comprising the N-terminal region;
  iii) providing a compound that is candidate for being a synaptogyrin-3 inhibitor;
  iv) contacting the synaptogyrin-3 or fragment thereof provided in i) with the Tau protein or fragment thereof provided in ii) in the presence or absence of the compound provided in iii);
  v) identifying from iv) a compound that is, compared to identical conditions but for the absence of the compound, reducing binding of the Tau protein or fragment thereof to synaptogyrin-3 or fragment thereof; and
  vi) identifying, from v), as inhibitor of synaptogyrin-3 a compound that is specifically binding to the synaptogyrin-3 or fragment thereof.

A further in vitro method for identifying a synaptogyrin-3 inhibitor may be comprising the steps of: i) providing synaptogyrin-3, or a fragment of synaptogyrin-3 comprising one or more of the intraneuronally exposed regions of synaptogyrin-3;
  ii) providing Tau protein, or a fragment of Tau comprising the N-terminal region;
  iii) providing a synaptogyrin-3-specific compound that is candidate for being a synaptogyrin-3 inhibitor;
  iv) contacting the synaptogyrin-3 or fragment thereof provided in i) with the Tau protein or fragment thereof provided in ii) in the presence or absence of the compound provided in iii);
  v) identifying as synaptogyrin-3 inhibitor, from iv) a compound that is, compared to identical conditions but for the absence of the compound, reducing binding of the Tau protein or fragment thereof to synaptogyrin-3 or fragment thereof.

In the above methods for identifying or screening for synaptogyrin-3 inhibitors the synaptogyrin-3 or fragment thereof may be provided on isolated synaptic vesicles, on virus-like particles, or in liposomes. Furthermore, the Tau protein or fragment thereof may be immobilized on a solid carrier, such as a magnetic solid carrier. Alternatively, or also, the synaptic vesicle, the virus-like particle or the liposome may be immobilized on a solid carrier. A further possibility is that the synaptogyrin-3 or fragment thereof and the Tau protein or fragment thereof are provided in a neuronal cell. In all of these methods the binding of the synaptogyrin-3 or fragment thereof to the Tau protein or fragment thereof may be determined by any suitable method such as immunologic or radiologic detection, co-sedimentation, co-immunoprecipitation, or electron microscopy.

A further in vitro method for identifying a synaptogyrin-3 inhibitor may be comprising the steps of:
  i) providing cells expressing synaptogyrin-3 or a fragment of synaptogyrin-3 comprising one or more of the intraneuronally exposed regions of synaptogyrin-3;
  ii) providing a synaptogyrin-3-specific compound that is candidate for being an inhibitor of synaptogyrin-3 expression;
  iii) administering a compound provided in ii) to the cells provided in i); and
  iv) identifying as synaptogyrin-3 inhibitor, from iii), a compound provided in ii) that is, compared to identical conditions but for the absence of the compound, reducing expression of synaptogyrin-3 or fragment thereof.

LEGENDS TO THE FIGURES

FIG. 1. Integrated forward proteomic and genetic screens identify Synaptogyrin-3 as a physical and genetic interactor of Tau. (A-D) Protein-protein interactions are required for the binding of Tau to SVs. (A) Ponceau S staining of fractions taken during Trypsin digestion of SVs shows proteolysis of SV proteins by Trypsin. (B) Immunoblotting of trypsinized SVs shows proteolytic degradation of the SV-associated proteins Synapsin (Syn) and Munc18, and degradation of the cytoplasmic domains of the transmembrane SV proteins SV2, Synaptobrevin-2 (Syb) (cytoplasmic epitopes) and Synaptotagmin-1 (Syt) (intravesicular epitope). (C) Representative immunoblots from co-sedimentation assay with purified recombinant human Tau-His and untreated or trypsinized SVs. Immunoblotting for Tau (anti-His antibody) in the SV pellet assesses binding to SVs as quantified in (D). Graph depicts mean±SD (n=3 experiments, Student's t-test). (E-G) Tau binding to SVs is mediated by interactions with transmembrane SV proteins. (E) Immunoblotting of untreated or carbonate-stripped SVs confirms removal of the SV-associated proteins Syn and Munc18 but retention of the transmembrane SV proteins SV2, Syt and Syb (cytoplasmic epitopes). (F) Representative immunoblots from co-sedimentation assay assessing Tau binding to untreated or carbonate-stripped SVs as quantified in (G). Graph depicts mean±SD (n=2 experiments) (H-I) Identification of the SV interactor of Tau by mass spectrometry. (H) Experimental workflow of co-IP of SV protein lysate with purified recombinant human Tau. (I) Filtered results from LC-MS/MS analysis showing peptide counts summed from 3 replicates. Proteins specific to the N-terminus of Tau are Synaptogyrin-3 and Rabphilin-3A. See Table S2 for unfiltered raw dataset. (J-K) In vivo follow-up screen of candidate interactors in *Drosophila*. (J) Experimental workflow to assess Tau binding to SVs at NMJs upon loss of candidate interactors identified in (I). (K) Binding of Tau to SVs was quantified by calculating the Pearson colocalization coefficient of immunolabeled Tau and the SV marker CSP at NMJs (see also FIG. 2). *Drosophila* larvae express UAS-Tau$^{P301L}$ or UAS-Tau$^{P301L}$ ΔN under the motor neuron-specific D42-Gal4 driver. Graph depicts mean±SEM (n≥8 NMJs per genotype from ≥4 animals per genotype, one-way ANOVA). See also FIGS. 5 and 6.

Figure 2:
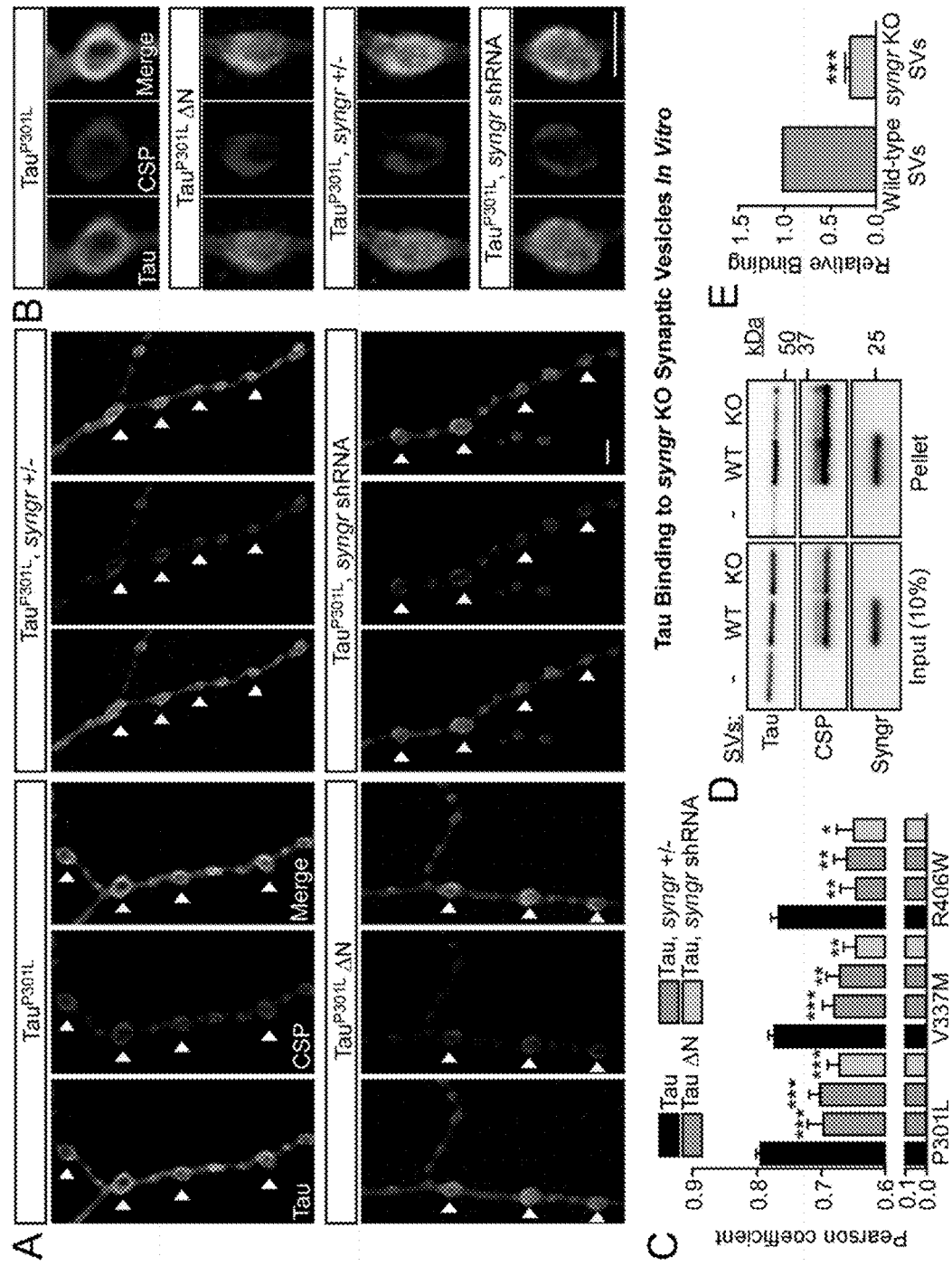

FIG. 2. *Drosophila* Synaptogyrin mediates Tau association with synaptic vesicles in vivo and in vitro. *Drosophila* larvae express pathological mutant UAS-Tau, UAS-Tau ΔN, and/or UAS-syngr shRNA under control of the D42-Gal4 motor neuron promoter on a wild-type (WT) or syngr$^{+/-}$ background. (A) Representative confocal images of immunolabeled Tau (DAKO antibody) and SVs (CSP antibody) at *Drosophila* NMJs. Arrows indicate presynaptic boutons. Boutons are shown enlarged in (B). Scale bars are 5 μm. (C) Quantification of Pearson colocalization coefficient of Tau and CSP upon heterozygous loss or knockdown of Syngr in larvae expressing pathological Tau mutants. Graph depicts mean±SEM (n=10-28 NMJs from ≥6 animals per genotype, one-way ANOVA, each condition compared to Tau-only for each respective mutant genotype). (D) Representative immunoblots detecting recombinant human Tau binding to SVs isolated from WT or syngr KO fly brains in co-sedimentation assay as quantified in (E). Graph depicts mean±SD (n=4 experiments, Student's t-test). See also FIG. 6.

Figure 3:
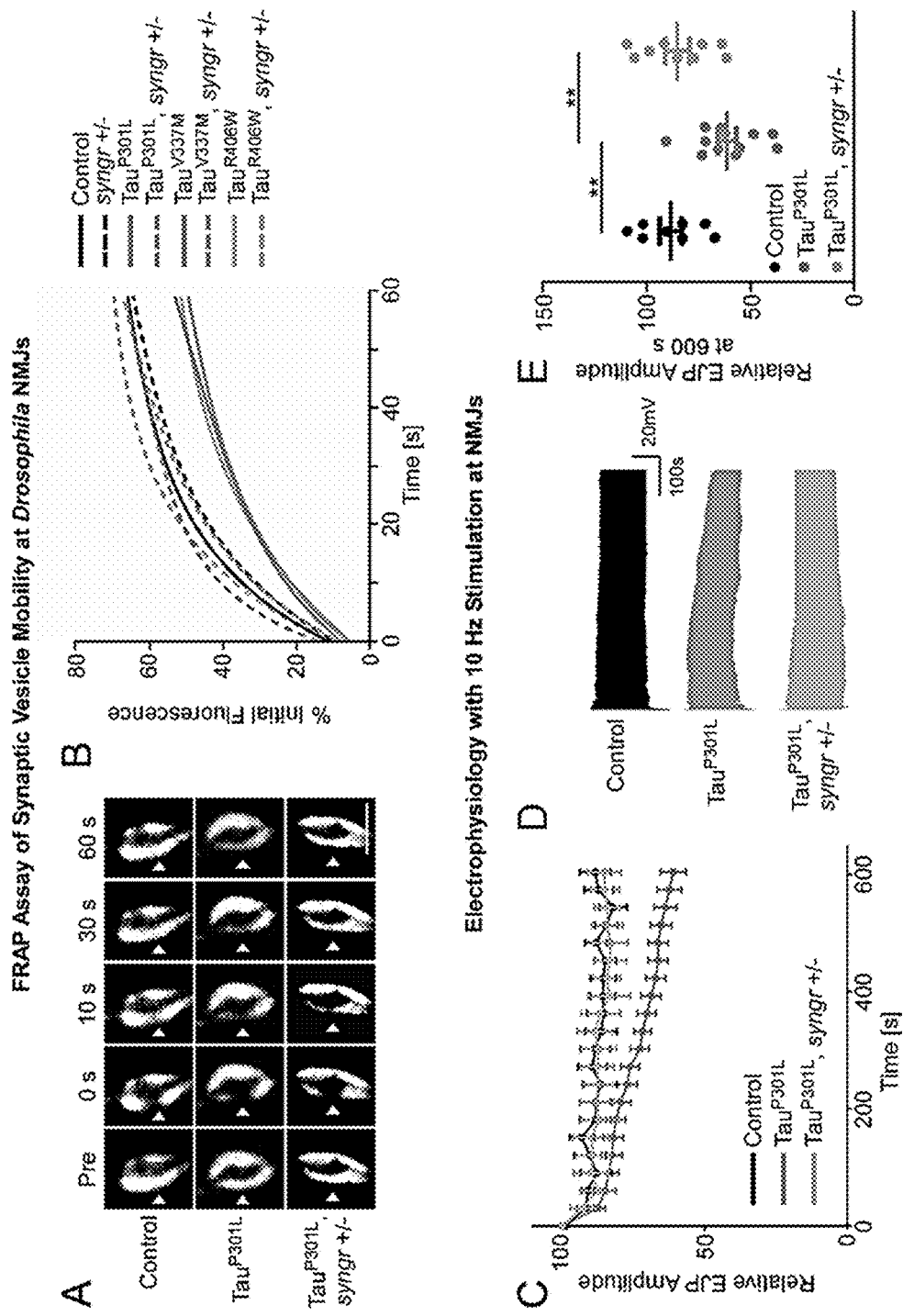

FIG. 3. Reduction of Synaptogyrin rescues Tau-induced defects in synaptic vesicle mobility and neurotransmitter release at Drosophila neuromuscular junctions. (A-B) FRAP assay to measure SV mobility within presynaptic boutons. Drosophila larvae express UAS-Syt-GFP and UAS-Tau under control of the D42-Gal4 motor neuron driver on a WT or syngr$^{+/-}$ background. (A) Representative images of Syt-GFP signal pre- and after photobleaching show fluorescence recovery after photobleaching of small area (arrow) of Syt-GFP fluorescence in presynaptic bouton during 60 s. Control is D42>Syt-GFP only. Scale bar is 5 μm. (B) Plot of Syt-GFP fluorescence recovery over time fit to a double-exponential curve. Traces are averaged from n=10-15 boutons from ≥5 animals. (C-E) Electrophysiological recordings of neurotransmitter release at NMJs. (C) Plot of average excitatory junction potential (EJP) amplitudes in response to 10 Hz stimulation over 10 min from control (D42 driver only, n=8), D42>Tau$^{P301L}$ (n=12) or Tau$^{P301L}$, syngr$^{+/-}$ (n=9) NMJs (1 NMJ per animal). Amplitudes are binned at 30 s intervals and normalized to the average of the first 15 s. Graph depicts mean±SEM. (D) Representative raw data traces. (E) Relative evoked EJP amplitude at 600 s plotted as individual data points. Graph depicts mean±SEM (one-way ANOVA).

Figure 4:
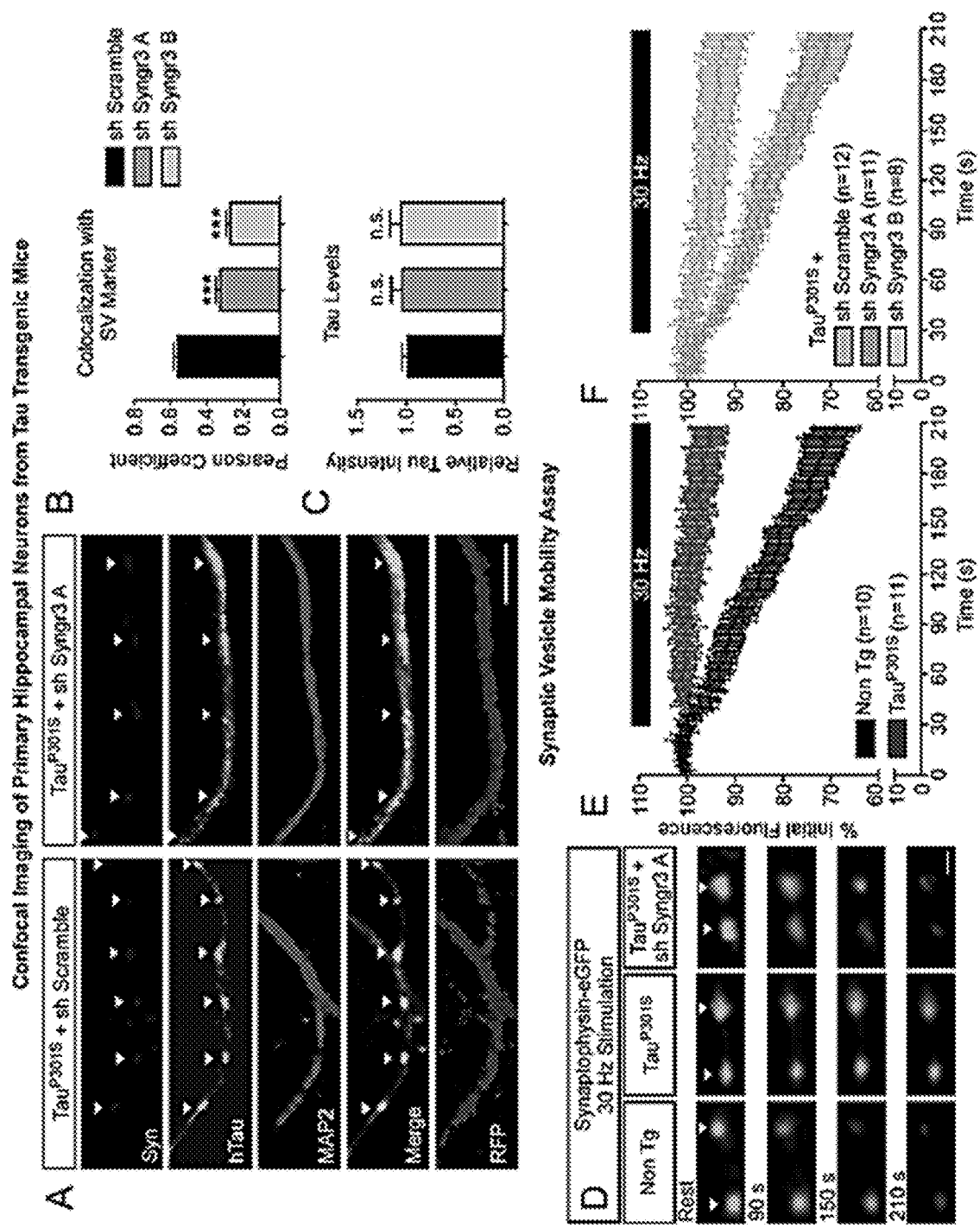
Figure 4:
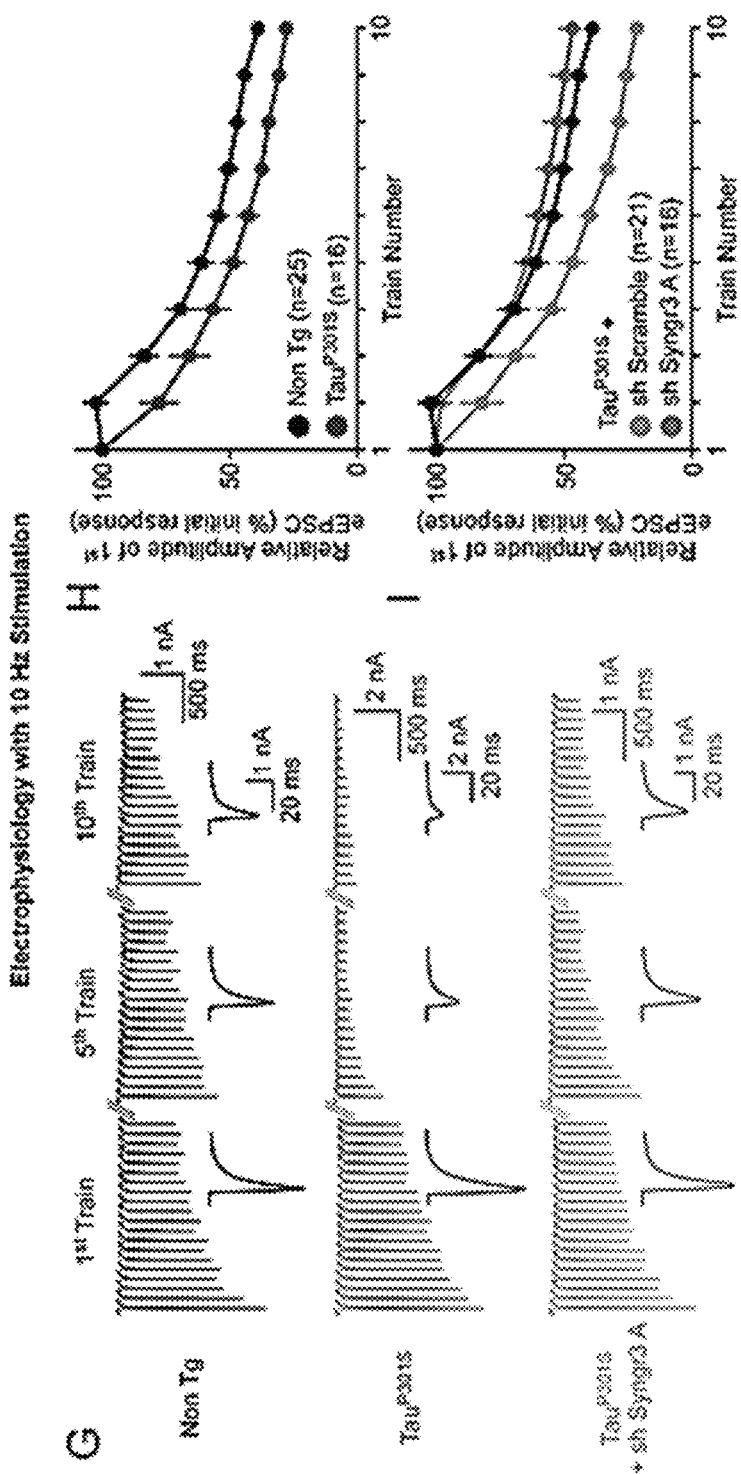

FIG. 4. Reduction of Synaptogyrin-3 rescues presynaptic dysfunction in primary hippocampal neurons from Tau transgenic mice. (A-C) Syngr3 mediates Tau localization to presynaptic vesicle clusters. (A) Representative confocal images of Tau$^{P301S}$ neurons (at DIV 17) transduced with lentivirus expressing RFP and encoding scrambled or Syngr3 knock-down shRNAs and immunolabeled for Tau$^{P301S}$ (hTau HT7 antibody), the SV marker Synapsin (Syn) and the dendritic marker MAP2 Arrows indicate presynaptic Syn puncta along axons. Scale bar is 5 μm. (B) Quantification of Tau$^{P301S}$ localization to SVs (Pearson coefficient of Tau and Syn along axons). (C) Quantification of overall Tau$^{P301S}$ levels (hTau intensity along axons). Graphs depict mean±SEM (n=85 axons/cells from >24 coverslips per condition from 6 independent cultures, one-way ANOVA). (D-F) Synaptogyrin-3 mediates Tau-induced defects in vesicle mobility. Neurons from non-transgenic (Non Tg) littermates or Tau$^{P301S}$ mice were transduced with lentivirus expressing Syph-GFP only or in combination with scrambled or Syngr3 shRNA virus. (D) Representative images of Syph-GFP fluorescence intensity during sustained 30 Hz stimulation. Arrows indicate presynaptic Syph-GFP puncta (SV clusters). Scale bar is 1 μm. (E-F) Plots depicting change in Syph-GFP fluorescence intensity in Non Tg and Tau$^{P301S}$ neurons (E) or in Tau$^{P301S}$ neurons co-transduced with shRNA virus (F). Neurons were imaged at rest for 30 s then stimulated at 30 Hz in a field stimulation chamber for 3 min. The change in fluorescence was calculated for ≥20 puncta from ≥3 axons per coverslip then averaged to give n=1 trace per coverslip. Plots depict mean±SEM (n is indicated from ≥5 independent cultures). See also FIG. 7. (G-I) Knock-down of Synaptogyrin-3 rescues Tau-induced defects in evoked neurotransmitter release. (G) Representative traces from recordings of autaptic hippocampal neurons in response to 10 consecutive high frequency stimulation trains (10 Hz for 10 s with 30 s interval) using patch clamp electrophysiology. (H-I) Relative first eEPSCs for each train plotted to train number from recordings of Tau$^{P301S}$ and Non Tg littermates (H) or Tau$^{P301S}$ neurons transduced with shRNA virus (I). Plots depict mean±SEM (n is indicated from ≥3 independent cultures). See also FIG. 7.

Figure 5:
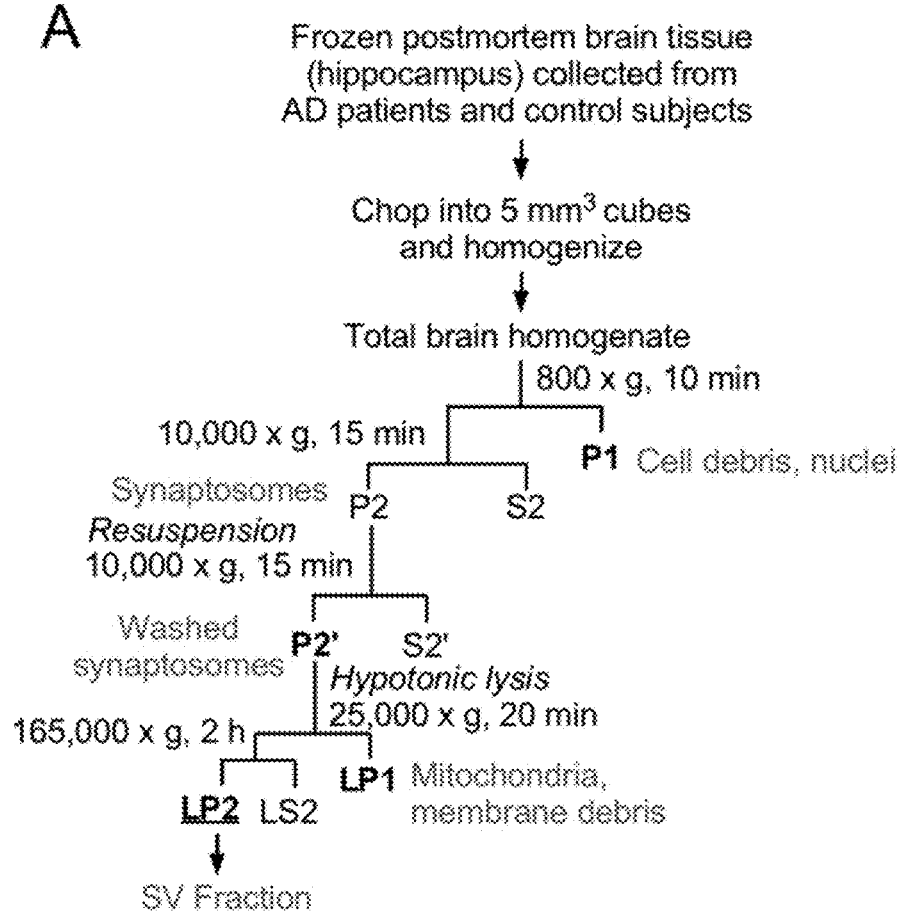
Figure 5:
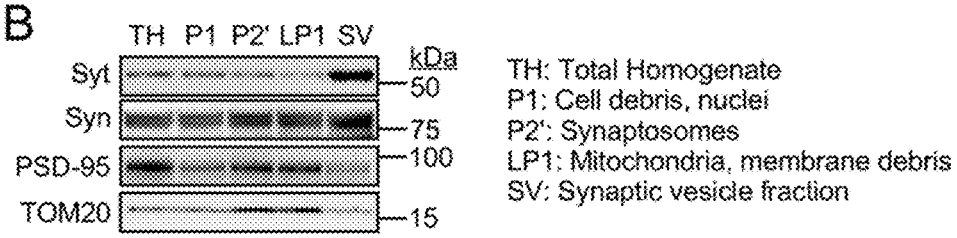
Figure 5:
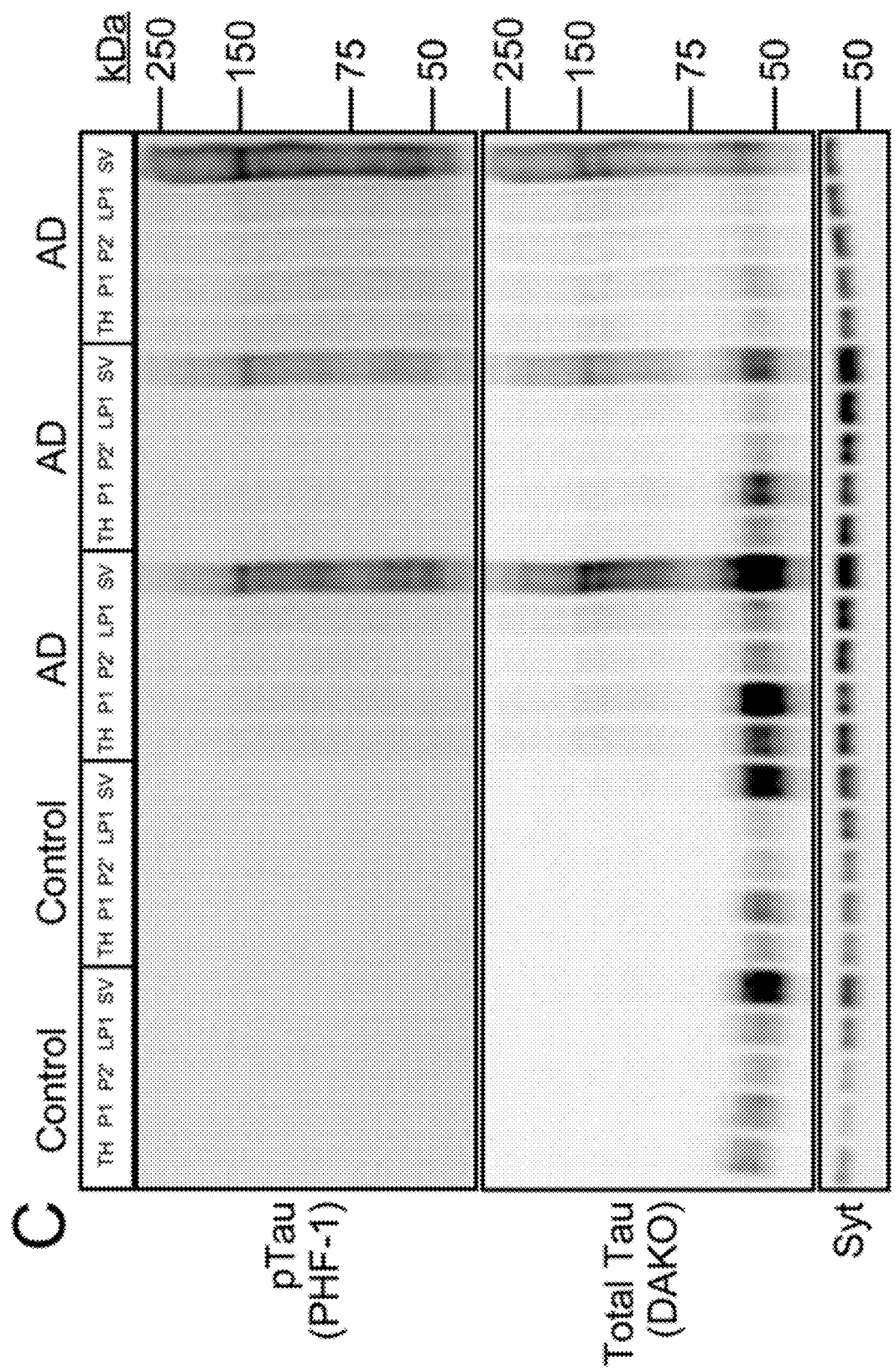
Figure 5:
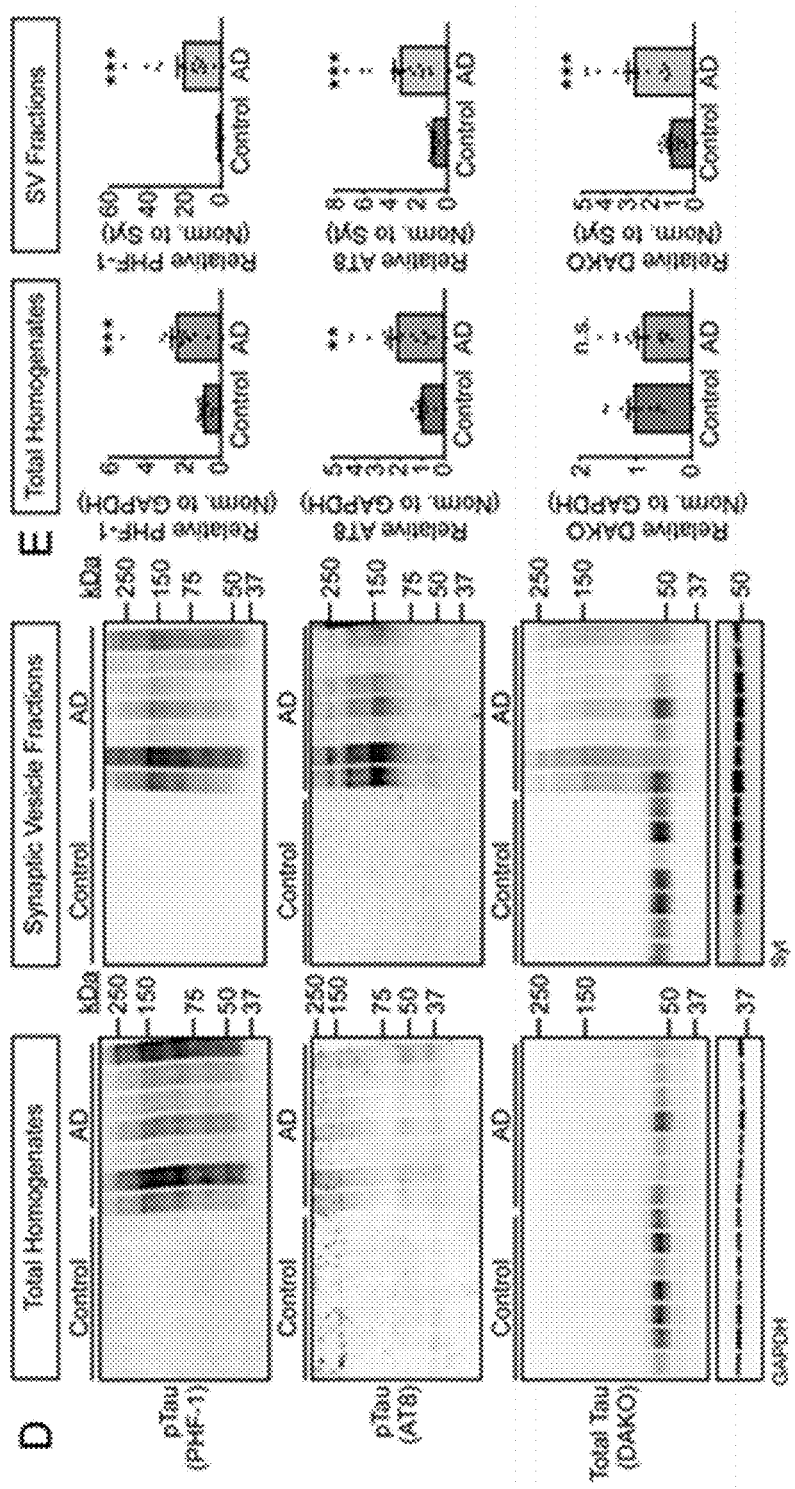

FIG. 5. Pathological Tau species accumulate on synaptic vesicles isolated from Alzheimer disease (AD) patient brains. Related to FIG. 1. (A) Schematic depicting isolation of SVs from postmortem human brain tissue. (B) Representative immunoblots of fractions (20 μg protein of each fraction) collected during SV isolation from a non-demented control subject show enrichment of the SV markers Synaptotagmin-1 (Syt) and Synapsin-1 (Syn), and depletion of the post-synaptic marker PSD-95 and the mitochondrial marker TOM20. (C) Representative immunoblots detecting phospho-Tau (pTau) using PHF-1 antibody (phospho-Ser396/Ser404 epitope) or total Tau (DAKO) antibody of representative subcellular fractions (20 μg protein of each fraction) collected during SV isolation from AD patient brains in comparison to control subject brains. Immunoblotting of Syt verifies enrichment of SVs in the SV fractions. Note the presence of both monomeric (around 50 kDa) as well as oligomeric (≥100 kDa) pTau species. (D) Representative immunoblots directly comparing the amount of pTau detected with PHF-1 antibody or AT8 antibody (phospho-Ser202/Thr205 epitope), or total Tau (DAKO antibody) present in total homogenates or in SV fractions from AD patients or controls. GAPDH and Syt are used as loading controls for total homogenates and SV fractions, respectively. (E) Quantifications of immunoblots comparing pTau or total Tau levels in control and AD patient brain in either total homogenate or SV fractions. Graphs depict mean±SEM (n=13 non-demented control subjects, n=15 AD patients, Student's t-test). See Table 51 for patient case information.

Figure 6:
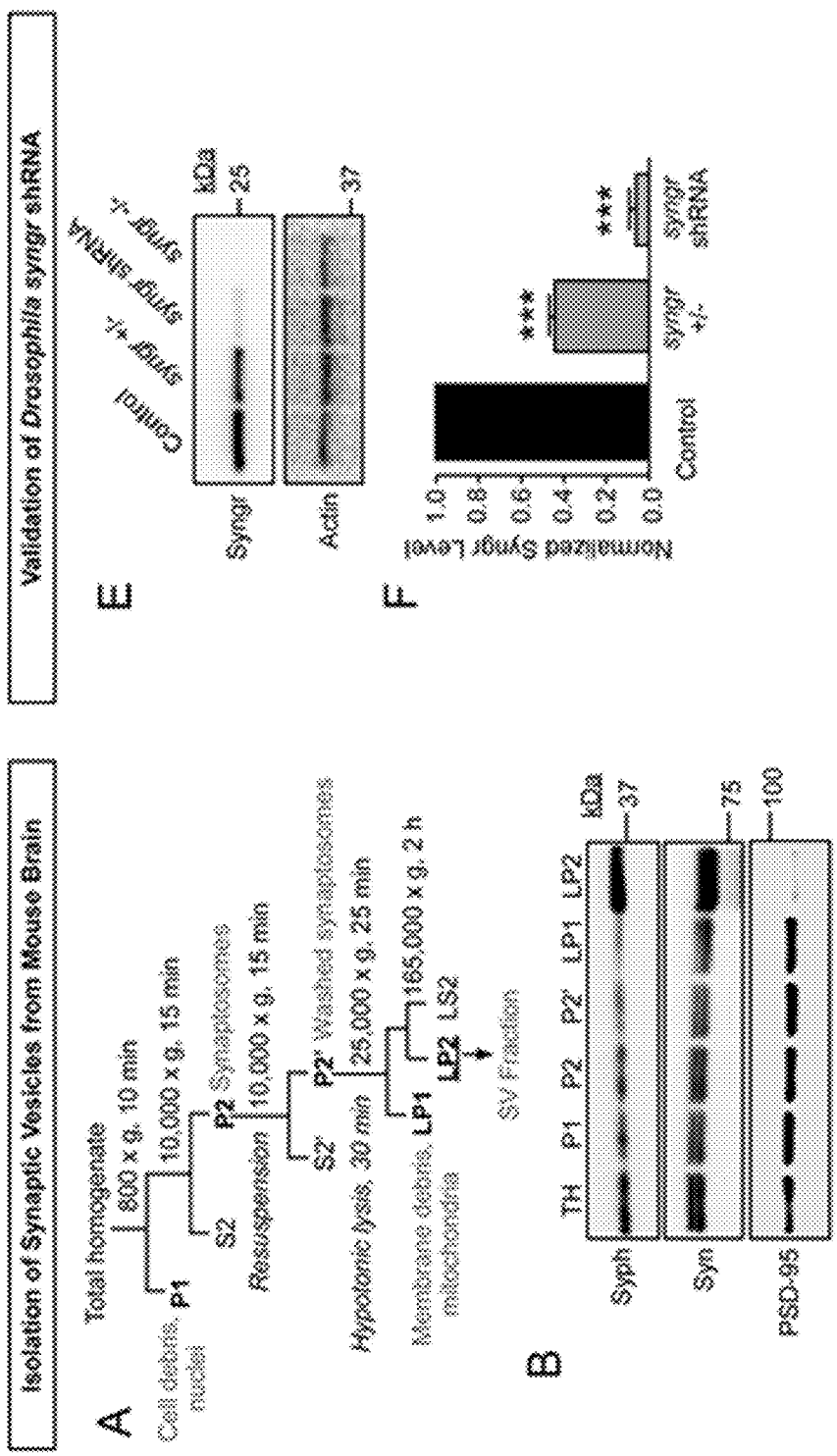
Figure 6:
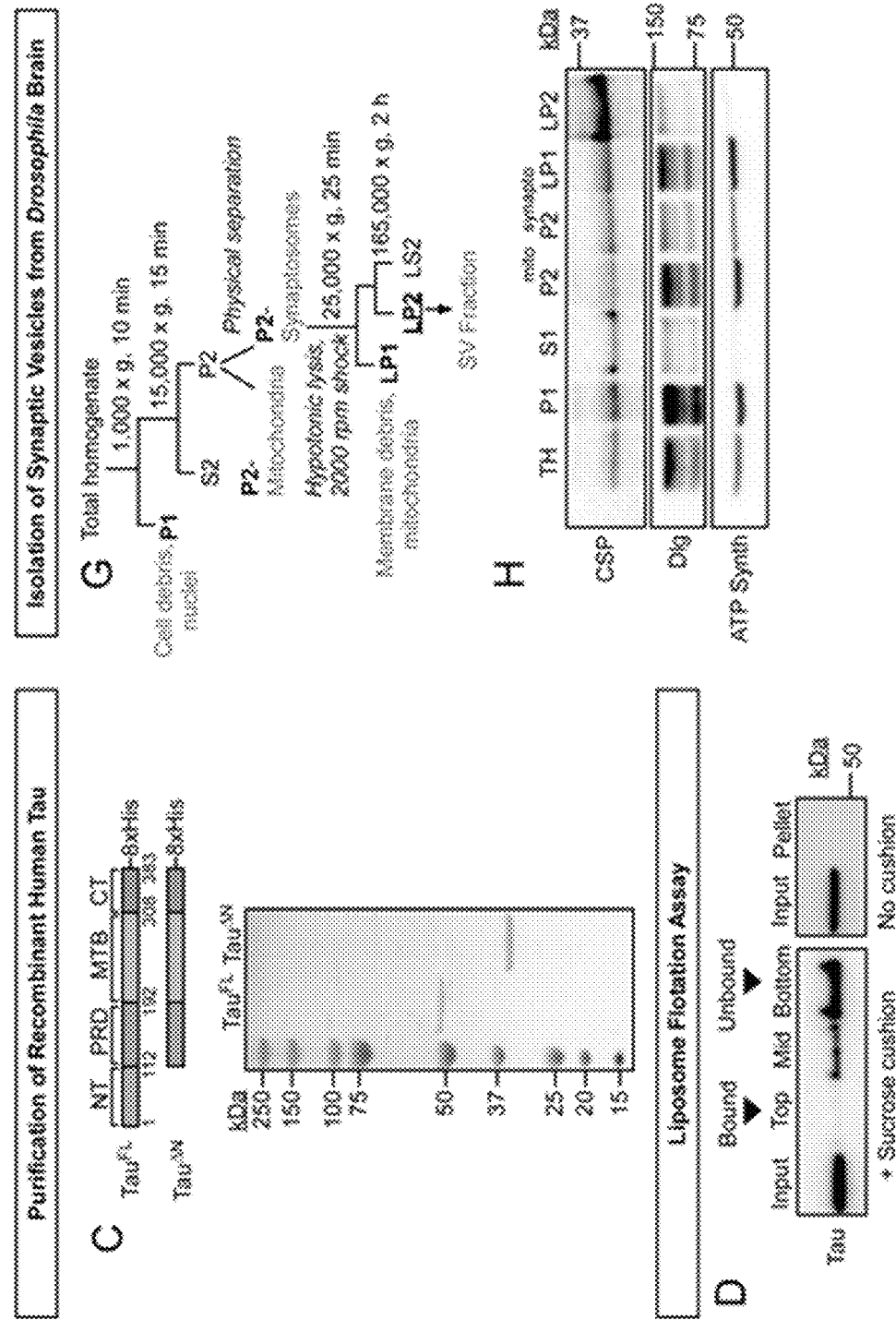

FIG. 6. Related to Figures 1 and 2. (A-B) Isolation of synaptic vesicles from mouse brain. (A) Schematic depicting isolation procedure of SVs from mouse brain. (B) Immunoblotting of fractions collected during SV isolation (20 μg protein of each fraction) shows the SV fraction (LP2) is enriched for the SV markers Synaptophysin (Syph) and Synapsin (Syn) and depleted of the postsynaptic marker PSD-95. (C) Purification of recombinant human Tau. Colloidal coomassie staining (1 μg protein) of recombinant 8×His-tagged full-length (FL, aa 1-383) or N-terminally truncated (ΔN, aa 113-383) wild-type human Tau (0N4R isoform) purified from bacterial cultures. (D) Co-flotation assay of recombinant Tau and liposomes. Tau and liposomes were incubated together, then covered by a sucrose cushion and centrifuged. Due to their density, liposomes rise to the top fraction of the sucrose cushion after centrifugation. Left panel: Immunoblot showing that recombinant Tau (anti-His antibody) does not rise to the top fraction together with liposomes in a co-flotation assay, indicating a lack of binding. Each fraction was loaded in equal volumes. Right panel: The retention of Tau in the bottom fraction is not due to the pelleting of Tau (e.g. due to aggregation), as Tau alone does not pellet in the absence of a sucrose cushion. Inputs are 10%. (E-F) Knock-down efficiency of Drosophila syngr shRNA. (E) Representative immunoblot of Syngr levels in protein lysates from adult fly brain, as quantified in (F). Level was normalized to actin loading control. Wild-type w1118 flies were used as controls. The UAS-syngr shRNA is driven by the pan-neuronal nSyb-Gal4 driver. Graph depicts mean±SD (n=3 experiments, one-way ANOVA). (G-H) Isolation of synaptic vesicles from adult Drosophila brain. (G) Schematic depicting isolation procedure of SVs from adult *Drosophila* brain. (H) Immunoblots of fractions collected during SV isolation (20 μg protein of each fraction) shows the SV fraction is enriched for the SV marker Cysteine String Protein (CSP), and depleted of the postsynaptic marker Discs-large (Dlg) and the mitochondrial marker ATP synthase.

Figure 7:
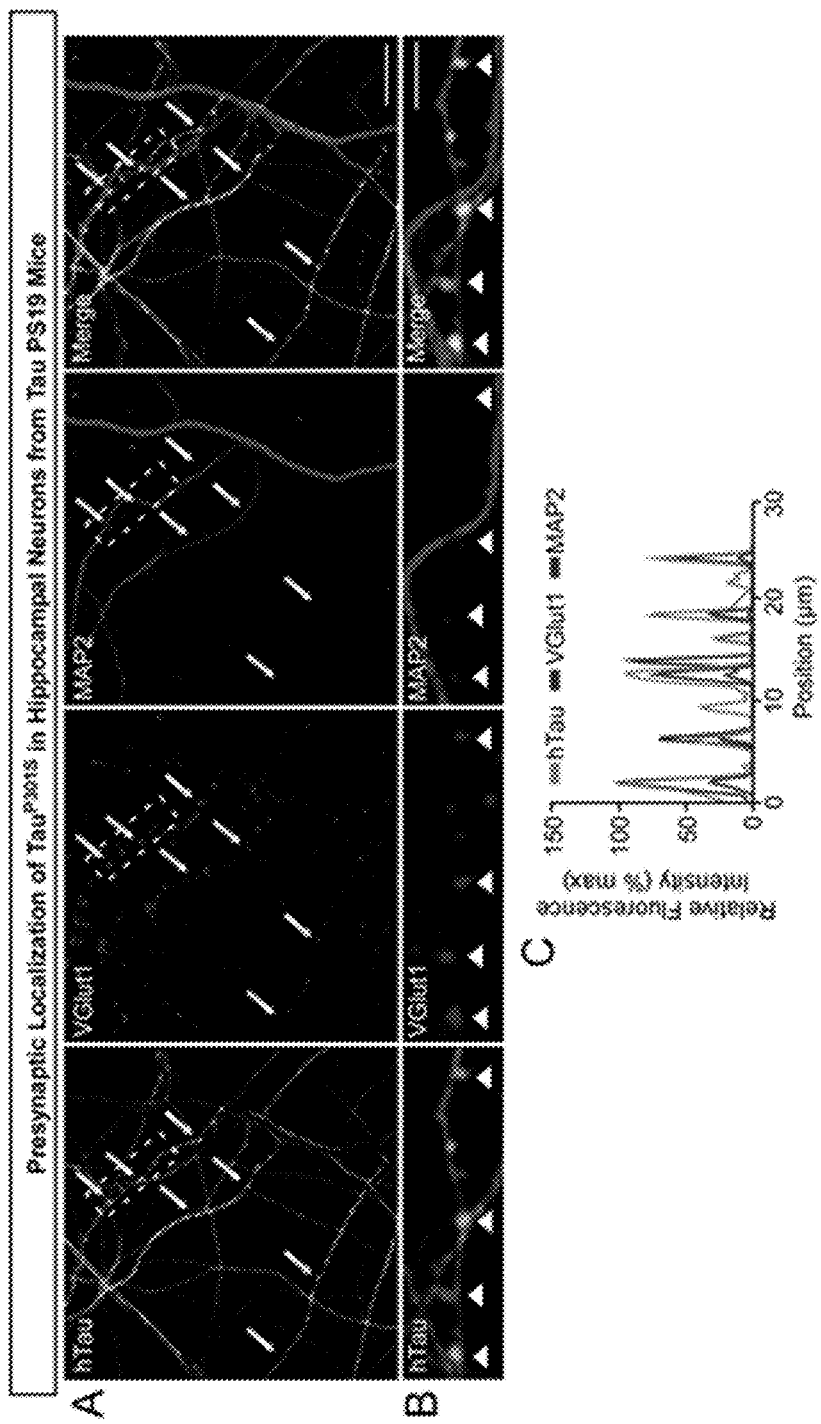
Figure 7:
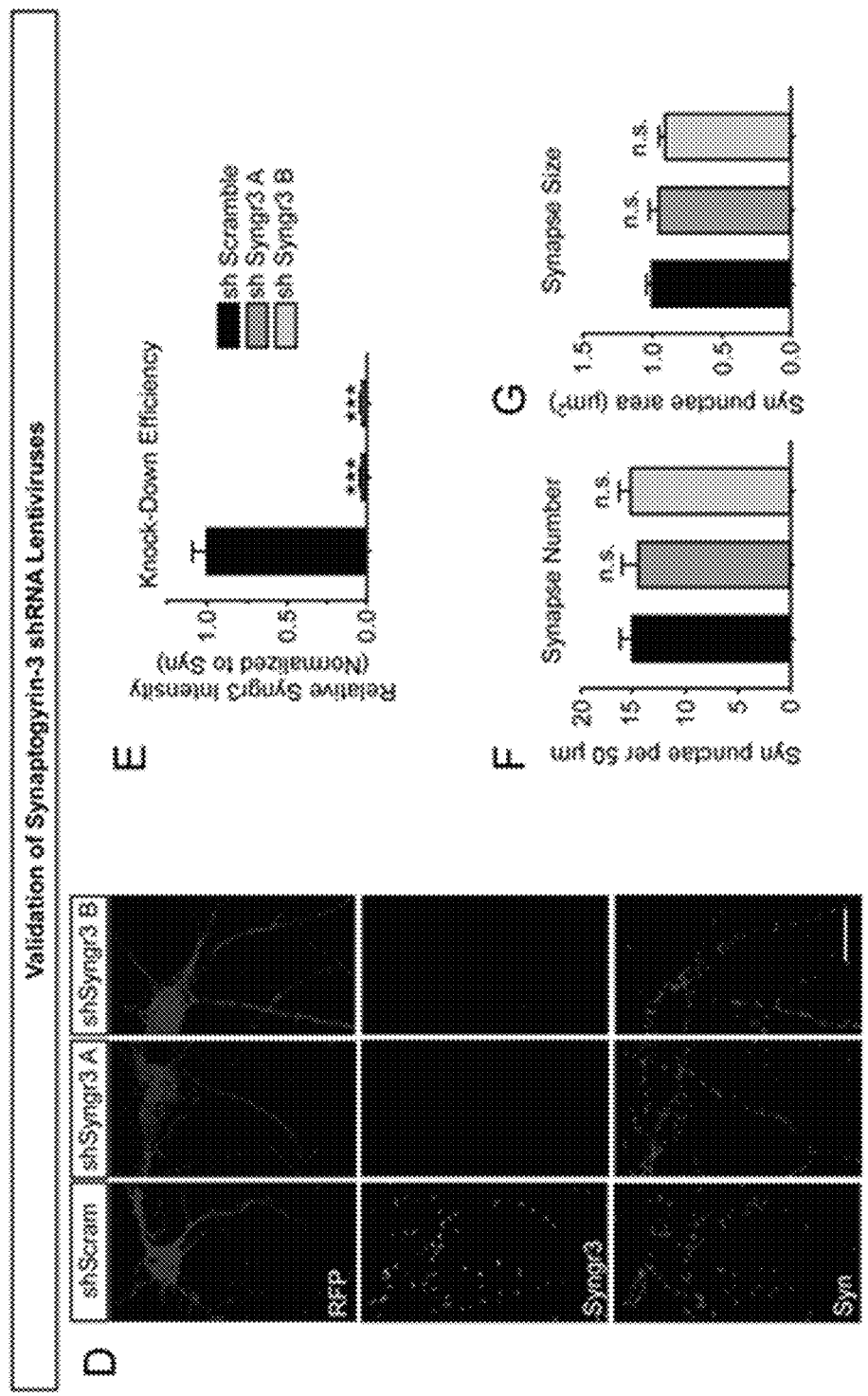

FIG. 7. Related to FIG. 4. (A-C) Tau$^{P301S}$ displays punctate presynaptic localization in primary neurons from Tau transgenic mice. (A) Representative images of primary hippocampal neurons (at DIV17) from Tau PS19 mice immunolabeled for Tau$^{P301S}$ (hTau), the presynaptic SV marker VGlut1, and the dendritic marker MAP2. Note the punctate staining pattern of hTau (HT7 antibody) in distal axons (arrows), which colocalizes with VGlut1. Scale bar is 15 μm. (B) Higher magnification of axonal segment depicted in box in (A). Arrows indicate presynaptic VGlut1 puncta. Scale bar is 5 μm. (C) Plot of relative fluorescence intensities by position along the axon depicted in (B) showing that hTau intensity peaks at positions of VGlut1. (D-G) Validation of Synaptogyrin-3 knock-down using lentiviruses encoding Synaptogyrin-3 shRNAs. Primary neurons were transduced on DIV5 with lentivirus encoding RFP and scrambled or Syngr3 shRNAs, then fixed on DIV11 and immunolabeled for Synaptogyrin-3 (Syngr3) and Synapsin (Syn). (D) Representative images of primary neurons transduced with lentivirus expressing RFP and encoding either scramble or Syngr3 shRNAs. Scale bar is 25 μm. (E) Quantification of Syngr3 levels. Synapses were identified by Syn labeling, and each synapse was measured for Syngr3 and Syn intensity. Syngr3 intensity at each puncta was normalized to Syn intensity, and all synaptic puncta were averaged to give the mean Syngr3 intensity value per cell. Graph depicts mean±SEM (n=50 axons/cells from ≥12 coverslips from 3 independent cultures, one-way ANOVA). (F) Quantification of number of synapses along axons of transduced neurons was measured as the number of Syn punctae per 50 μm of axon length per axon/cell. (G) Quantification of synapse area was measured as the area of each Syn puncta along an axon which was averaged to give the average synapse size for each axon/cell. In (F) and (G) graphs depict mean±SEM (n=20 axons/cells, one-way ANOVA).

Figure 8:
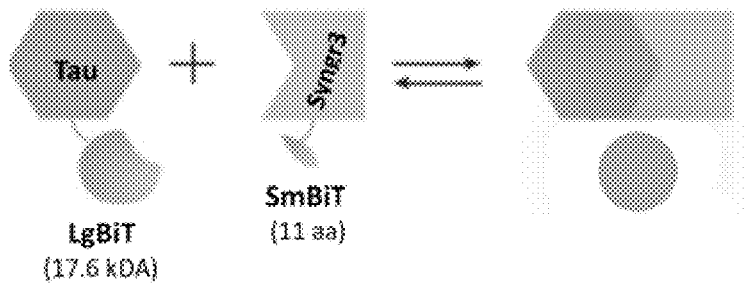

FIG. 8. Schematic representation of split luciferase assay. Tau and Syngr3 are coupled to one of the two luciferase subunits (i.e. LgBit and SmBit). Structural complementation generates a luminescent signal.

Figure 9:
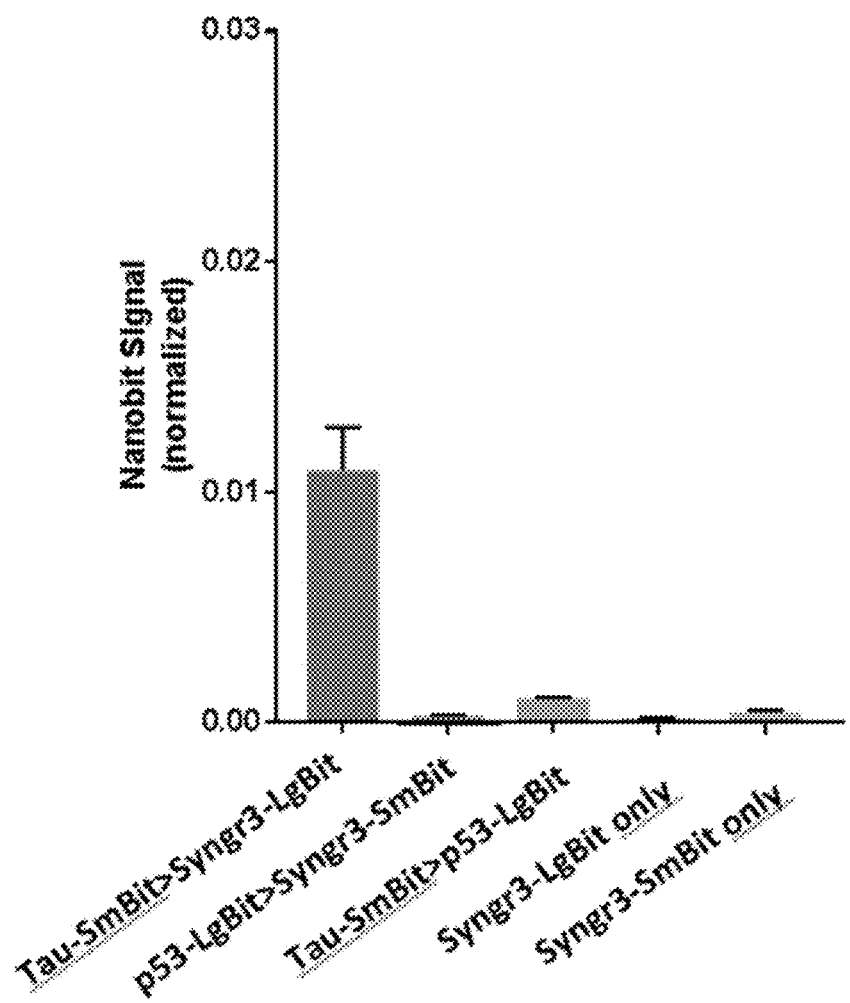

FIG. 9. Split luciferase assay showing the direct interaction between Tau and Syngr3. The normalized luminescent signal generated by the Tau-Syngr3 pair is significantly higher than that of the control interactions between p53 and Syngr3 or Tau or that of the single constructs.

DETAILED DESCRIPTION OF THE INVENTION

In work leading to the current invention, it was shown that hyperphosphorylated Tau species accumulate on presynaptic vesicles isolated from Alzheimer's disease patient brain, suggesting this pathway contributes to synaptic dysfunction in human disease. Early synaptic dysfunction is a key feature of neurodegenerative diseases associated with Tau, including Alzheimer's disease. Using unbiased proteomic and genetic approaches, it was found that the transmembrane synaptic vesicle protein Synaptogyrin-3 mediates the association of Tau with synaptic vesicles in vitro and in vivo. Reduction of *Drosophila* Synaptogyrin or murine Synaptogyrin-3 levels in neurons from fly and mouse models of tauopathy reduced the association of Tau with synaptic vesicles, and subsequently rescued Tau-induced defects in vesicle mobility and neurotransmitter release. These findings identify Synaptogyrin-3 as a novel Tau interactor, more specifically as an N-tau interactor, that mediates synaptic dysfunction associated with Tau, providing important insights into Tau biology and opening new avenues for specifically targeting early presynaptic dysfunction in various Tauopathies including Alzheimer's disease, conditions for which there continues to be a high unmet need for therapies.

In one aspect, the current invention therefore generally relates to a synaptogyrin-3 inhibitor for use as a medicament. In one embodiment thereto, the synaptogyrin-3 inhibitor is for use in (a method for) treating or inhibiting progression of a tauopathic disorder or for use in (a method for) treating or inhibiting a symptom of a tauopathic disorder. In particular, the synaptogyrin-3 inhibitor is an inhibitor of human synaptogyrin-3. The nature of the inhibitor is not vital/essential to the invention as long as, as explained further herein, the expression or function of synaptogyrin-3 is (partially) inhibited such as to restore pathological Tau-induced presynaptic dysfunction. In the methods for treating or inhibiting progression of a tauopathic disorder or a symptom of a tauopathic disorder, a synaptogyrin-3 inhibitor is administered to a subject in need thereof (a subject suffering of or displaying a tauopathy or symptom thereof) in an effective amount, i.e. in an amount sufficient to treat or to inhibit progression of a tauopathic disorder or a symptom of a tauopathic disorder.

For the purpose of treating, preventing or inhibiting (progression of) an intended disease or disorder, and in method for treating, preventing or inhibiting (progression of) an intended disease or disorder, an effective amount of the therapeutic compound is administered to a subject in need thereof. An "effective amount" of an active substance in a composition is the amount of said substance required and sufficient to elicit an adequate response in treating, preventing, inhibiting (progression of) the intended or targeted medical indication. It will be clear to the skilled artisan that such response may require successive (in time) administrations with the composition as part of an administration scheme or—schedule. The effective amount may vary depending on the nature of the compound, the route of administration of the compound (crossing of the blood-brain barrier and the cell membrane are potential barriers to be taken by synaptogyrin-3 inhibitors as described herein), the health and physical condition of the individual to be treated, the age of the individual to be treated (e.g. dosing for infants may be lower than for adults) the taxonomic group of the individual to be treated (e.g. human, non-human primate, primate, etc.), the capacity of the individual's system to respond effectively, the degree of the desired response, the formulation of the active substance, the treating doctor's assessment and other relevant factors. The effective amount further may vary depending on whether it is used in monotherapy or in combination therapy. Determination of an effective amount of a compound usually follows from pre-clinical testing in a representative animal or in vitro model (if available) and/or from dose-finding studies in early clinical trials.

Inhibition of Synaptogyrin-3

Inhibition of synaptogyrin-3 may be obtained at the expression level (gene expression and/or protein production) or at the functional level (interfering with the protein's function or structure) as described in more detail hereafter. As herein demonstrated (see Example 2.2; heterozygous loss of synaptogyrin-3), partial inhibition of synaptogyrin-3 is sufficient to restore pathological Tau-induced presynaptic dysfunction. As such, inhibition of synaptogyrin-3 implies several possible levels of inhibition, e.g., at least 20%, at least 30%, at least 40%, at least 50%, at least 60%, at least 70%, at least 80%, at least 90%, at least 95% or even 100% inhibition. The nature of the inhibitor is not vital/essential to the invention as long as the expression or function of synaptogyrin-3 is (partially) inhibited such as to restore pathological Tau-induced presynaptic dysfunction. In describing hereafter different processes of inhibition, the synaptogyrin-3 gene or protein will be referred to as target gene or gene of interest, as protein of interest, or shortly as target of interest.

One process of modulating expression of a gene of interest relies on antisense oligonucleotides (ASOs), or variants thereof such as gapmers. An antisense oligonucleotide (ASO) is a short strand of nucleotides and/or nucleotide analogues that hybridizes with the complementary mRNA in a sequence-specific manner via Watson-Crick base pairing. Formation of the ASO-mRNA complex ultimately results in downregulation of target protein expression. Depending on the target sequence, ASOs can act in different ways. If the ASO is taken up by cellular endocytosis and hybridizes with target mRNA in the cytoplasm, formation of an ASO-mRNA complex can induce activation of RNase H (selective degradation of bound mRNA) or can sterically interference with ribosomal assembly. In case the ASO can enter the nucleus, mRNA maturation can be modulated by inhibition of 5' cap formation, inhibition of mRNA splicing or activation of RNaseH (Chan et al. 2006, Clin Exp Pharmacol Physiol 33:533-540; this reference also describes some of the software available for assisting in design of ASOs). Modifications to ASOs can be introduced at one or more levels: phosphate linkage modification (e.g. introduction of one or more of phosphodiester, phosphoramidate or phosphorothioate bonds), sugar modification (e.g. introduction of one or more of LNA (locked nucleic acids), 2'-O-methyl, 2'-O-methoxy-ethyl, 2'-fluoro, S-constrained-ethyl or tricyclo-DNA and/or non-ribose modifications (e.g. introduction of one or more of phosphorodiamidate morpholinos or peptide nucleic acids). The introduction of 2'-modifications has been shown to enhance safety and pharmacologic properties of antisense oligonucleotides. Antisense strategies relying on degradation of mRNA by RNase H requires the presence of nucleotides with a free 2'-oxygen, i.e. not all nucleotides in the antisense molecule should be 2'-modified. The gapmer strategy has been developed to this end. A gapmer antisense oligonucleotide consists of a central DNA region (usually a minimum of 7 or 8 nucleotides) with (usually 2 or 3) 2'-modified nucleosides flanking both ends of the central DNA region. This is sufficient for the protection against exonucleases while allowing RNAseH to act on the (2'-modification free) gap region.

After reaching the nervous system, most antisense oligonucleotides are readily taken up by neurons and glia. Therapeutic nucleotides tend to display a significant higher half-life in neuronal tissues compared to peripheral tissues (Whitesell et al. 1995, Proc Natl Acad Sci USA 90:4665-4669; Butler et al. 2005, Neuroscience 131:707-715). Antidote strategies are available as demonstrated by administration of an oligonucleotide fully complementary to the antisense oligonucleotide (Crosby et al. 2015, Nucleic Acid Ther 25:297-305).

Another process to modulate expression of a gene of interest is based on the natural process of RNA interference. It relies on double-stranded RNA (dsRNA) that is cut by an enzyme called Dicer, resulting in double stranded small interfering RNA (siRNA) molecules which are 20-25 nucleotides long. siRNA then binds to the cellular RNA-Induced Silencing Complex (RISC) separating the two strands into the passenger and guide strand. While the passenger strand is degraded, RISC is cleaving mRNA specifically at a site instructed by the guide strand. Destruction of the mRNA prevents production of the protein of interest and the gene is 'silenced'. siRNAs are dsRNAs with 2 nt 3' end overhangs whereas shRNAs are dsRNAs that contains a loop structure that is processed to siRNA. shRNAs are introduced into the nuclei of target cells using a vector (e.g. bacterial or viral) that optionally can stably integrate into the genome. Apart from checking for lack of cross-reactivity with non-target genes, manufacturers of RNAi products provide guidelines for designing siRNA/shRNA. siRNA sequences between 19-29 nt are generally the most effective. Sequences longer than 30 nt can result in nonspecific silencing. Ideal sites to target include AA dinucleotides and the 19 nt 3' of them in the target mRNA sequence. Typically, siRNAs with 3' dUdU or dTdT dinucleotide overhangs are more effective. Other dinucleotide overhangs could maintain activity but GG overhangs should be avoided. Also to be avoided are siRNA designs with a 4-6 poly(T) tract (acting as a termination signal for RNA pol III), and the G/C content is advised to be between 35-55%. shRNAs should comprise sense and antisense sequences (adviced to each be 19-21 nt in length) separated by loop structure, and a 3' AAAA overhang. Effective loop structures are suggested to be 3-9 nt in length. It is suggested to follow the sense-loop-antisense order in designing the shRNA cassette and to avoid 5' overhangs in the shRNA construct. shRNAs are usually transcribed from vectors, e.g. driven by the Pol III U6 promoter or H1promoter. Vectors allow for inducible shRNA expression, e.g. relying on the Tet-on and Tet-off inducible systems commercially available, or on a modified U6 promoter that is induced by the insect hormone ecdysone. A Cre-Lox recombination system has been used to achieve controlled expression in mice. Synthetic shRNAs can be chemically modified to affect their activity and stability. Plasmid DNA or dsRNA can be delivered to a cell by means of transfection (lipid transfection, cationic polymer-based nanoparticles, lipid or cell-penetrating peptide conjugation) or electroporation. Viral vectors include lentiviral, retroviral, adenoviral and adeno-associated viral vectors.

Kumar et al. 2007 (Nature 448:39-43) demonstrated uptake of small interfering RNA (siRNA) in the brain after coupling to a 29-amino acid peptide derived from rabies virus glycoprotein (RVG) which is specifically binding the acetylcholine receptor.

Ribozymes (ribonucleic acid enzymes) are another type of molecules that can be used to modulate expression of a target gene. They are RNA molecules capable of catalyzing specific biochemical reactions, in the current context capable of targeted cleavage of nucleotide sequences. Examples of ribozymes include the hammerhead ribozyme, the Varkud Satellite ribozyme, Leadzyme and the hairpin ribozyme.

Besides the use of the inhibitory RNA technology, modulation of expression of a gene of interest can be achieved at DNA level such as by gene therapy to knock-out or disrupt the target gene. As used herein, a "gene knock-out" can be a gene knockdown or the gene can be knocked out by a mutation such as, a point mutation, an insertion, a deletion, a frameshift, or a missense mutation by techniques such as described hereafter, including, but not limited to, retroviral gene transfer. Another way in which genes can be knocked out is by the use of zinc finger nucleases. Zinc-finger nucleases (ZFNs) are artificial restriction enzymes generated by fusing a zinc finger DNA-binding domain to a DNA-cleavage domain. Zinc finger domains can be engineered to target desired DNA sequences, which enable zinc-finger nucleases to target unique sequence within a complex genome. By taking advantage of the endogenous DNA repair machinery, these reagents can be used to precisely alter the genomes of higher organisms. Other technologies for genome customization that can be used to knock out genes are meganucleases and TAL effector nucleases (TALENs, Cellectis bioresearch). A TALEN® is composed of a TALE DNA binding domain for sequence-specific recognition fused to the catalytic domain of an endonuclease that introduces double strand breaks (DSB). The DNA binding domain of a TALEN® is capable of targeting with high precision a large recognition site (for instance 17 bp). Meganucleases are sequence-specific endonucleases, naturally occurring "DNA scissors", originating from a variety of single-celled organisms such as bacteria, yeast, algae and some plant organelles. Meganucleases have long recognition sites of between 12 and 30 base pairs. The recognition site of natural meganucleases can be modified in order to target native genomic DNA sequences (such as endogenous genes). Another recent genome editing technology is the CRISPR/Cas system, which can be used to achieve RNA-guided genome engineering. CRISPR interference is a genetic technique which allows for sequence-specific control of gene expression in prokaryotic and eukaryotic cells. It is based on the bacterial immune system-derived CRISPR (clustered regularly interspaced palindromic repeats) pathway. Recently, it was demonstrated that the CRISPR-Cas editing system can also be used to target RNA. It has been shown that the Class 2 type VI-A CRISPR-Cas effector C2c2 can be programmed to cleave single stranded RNA targets carrying complementary protospacers (Abudayyeh et al 2016 Science 353/science.aaf5573). C2c2 is a single-effector endoRNase mediating ssRNA cleavage once it has been guided by a single crRNA guide toward the target RNA.

As indicated above, inhibition of synaptogyrin-3 may be obtained at the functional level by interfering with the protein's function or structure. Interfering with structure, which can also result in inhibition of function, can be achieved by e.g. binding moieties that shield e.g. the binding site on the protein of interest for a ligand of interest. Non-limiting examples are (monoclonal) antibodies or antigen-binding fragments thereof, alpha-bodies, nanobodies, intrabodies (antibodies binding and/or acting to intracellular target; this typically requires the expression of the antibody within the target cell, which can be accomplished by gene therapy), aptamers, DARPins, affibodies, affitins, anticalins, monobodies, phosphatases (in case of phosphorylated target) and kinases (in case of a phosphorylatable target).

The term "antibody" as used herein refers to any naturally occurring format of antibody or antigen-binding protein the production of which is induced by an immune system (immunoglobulins or IgGs). It is clear, however, that not all antibodies are naturally occurring as e.g. some antigens are problematic in the sense that they are poor or not at all immunogenic, or are not recognized by the immune system (e.g. self-antigens); artificial tricks may be required to obtain antibodies against such antigens (e.g. knock-out mice: e.g. Declercq et al. 1995, J Biol Chem 270:8397-8400; DNA immunization for e.g. transmembrane antigens; e.g. Liu et al. 2016, Emerg Microbes Infect 5:e33). "Conventional" antibodies comprise two heavy chains linked together by disulfide bonds and two light chains, one light chain being linked to each of the heavy chains by disulfide bonds. Each heavy chain has at one end a variable domain (VH) followed by a number of constant domains (three or four constant domains, CH1, CH2, CH3 and CH4, depending on the antibody class). Each light chain has a variable domain (VL) at one end and a constant domain (CL) at its other end; the constant domains of the light chains each align with the first constant domains of the heavy chains, and the light chain variable domains each align with the variable domains of the heavy chains. This type of antibodies exist in camels, dromedaries and llamas along with an "unconventional" naturally occurring type of antibodies consisting of only two heavy chains, and thus being devoid of light chains. Other "unconventional" naturally occurring antibodies exist in in the serum of nurse sharks (Ginglymostomatidae) and wobbegong sharks (Orectolobidae). These latter antibodies are called Ig new antigen receptors (IgNARs). They are disulfide-bonded homodimers consisting of five constant domains (CNAR) and one variable domain (VNAR). There is no light chain, and the individual variable domains are independent in solution and do not appear to associate across a hydrophobic interface (Greenberg et al. 1995, Nature 374, 168-173; Nuttall et al. 2001, Mol Immunol 38, 313-326; Diaz et al. 2002, Immunogenetics 54, 501-512; Nuttall et al. 2003, Eur J Biochem 270, 3543-3554). Due to the heavy chain dimer structure characteristic of camelid and shark antibodies, these are sometimes termed "Heavy-Chain Mini-Antibodies" (mnHCAbs) or simply "Mini-Antibodies" (mnAbs) (Holliger & Hudson 2005, Nature Biotechnol 23, 1 126-1136). The complementary determining region 3 (CDR3) of camel antibodies and shark antibodies is usually longer (comprising about 16-21 amino acids, and about 16-27 amino acids, respectively) than the CDR3 of mouse VH region (comprising about 9 amino acids) (Muyldermans et al. 1994, Prot Eng 7, 1129-1135; Dooley & Flajnik 2005, Eur J Immunol 35, 936-945). Without the light chain, these heavy-chain antibodies bind to their antigens by one single domain, the variable antigen binding domain of the heavy-chain immunoglobulin, referred to as Vab (camelid antibodies) or V-NAR (shark antibodies). These smallest intact and independently functional antigen-binding fragment Vab is referred to as nano-antibody or nanobody (Muyldermans 2001, J Biotechnol 74, 277-302). Multivalent (etc. divalent, trivalent, tetravalent and pentavalent) Vab and/or V-NAR domains may be preferred in some instances due to their potentially higher cellular intake and retention and may be made by recombinant technology or by chemical means, such as described in WO 2010/033913. The variable domains of the light and/or heavy chains are involved directly in binding the antibody to the antigen. The variable domains of naturally occurring light and heavy chains have the same general structure: four framework regions (FRs) connected by three complementarity determining regions (CDRs) (see e.g. Kabat et al. 1991, Sequences of Proteins of Immunological Interest, 5 th Ed. Public Health Service, National Institutes of Health, Bethesda, Md.). The CDRs in a light or heavy chain are held in close proximity by the FRs and contribute to the formation of the antigen binding site. An antibody, or antibody fragment as described hereafter, may also be part of a multivalent and/or multispecific antigen binding molecule. An overview of e.g. available bispecific formats (around 100) is provided in Brinkmann & Kontermann 2017 (mAbs 9:182-212).

The term "antibody fragment" refers to any molecule comprising one or more fragments (usually one or more CDRs) of an antibody (the parent antibody) such that it binds to the same antigen to which the parent antibody binds. Antibody fragments include Fv, Fab, Fab', Fab'-SH, single-chain antibody molecules (such as scFv), F(ab') 2, single variable VH domains, and single variable VL domains (Holliger & Hudson 2005, Nature Biotechnol 23, 1126-1136), Vab and V-NAR. The term further includes microantibodies, i.e. the minimum recognition unit of a parent antibody usually comprising just one CDR (Heap et al. 2005, J Gen Virol 86, 1791-1800). Any of the fragments can be incorporated in a multivalent and/or multispecific larger molecule, e.g. mono- or bi-specific Fab 2, mono- or tri-specific Fab 3, bis-scFv (mono- or bispecific), diabodies (mono- or bi-specific), triabodies (e.g. trivalent monospecific), tetrabodies (e.g. tetravalent monospecific), minibodies and the like (Holliger & Hudson 2005, Nature Biotechnol 23, 1 126-1136). Any of the fragments can further be incorporated in e.g. V-NAR domains of shark antibodies or VhH domains of camelid antibodies (nanobodies). All these are included in the term "antibody fragment".

Alphabodies are also known as Cell-Penetrating Alphabodies and are small 10 kDa proteins engineered to bind to a variety of antigens.

Aptamers have been selected against small molecules, toxins, peptides, proteins, viruses, bacteria, and even against whole cells. DNA/RNA/XNA aptamers are single stranded and typically around 15-60 nucleotides in length although longer sequences of 220 nt have been selected; they can contain non-natural nucleotides (XNA) as described for antisense RNA. A nucleotide aptamer binding to the vascular endothelial growth factor (VEGF) was approved by FDA for treatment of macular degeneration. Variants of RNA aptamers are spiegelmers are composed entirely of an unnatural L-ribonucleic acid backbone. A Spiegelmer of the same sequence has the same binding properties of the corresponding RNA aptamer, except it binds to the mirror image of its target molecule. Peptide aptamers consist of one (or more) short variable peptide domains, attached at both ends to a protein scaffold, e.g. the Affimer scaffold based on the cystatin protein fold. A further variation is described in e.g. WO 2004/077062 wherein e.g. 2 peptide loops are attached to an organic scaffold. Phage-display screening of such peptides has proven to be possible in e.g. WO 2009/098450.

DARPins stands for designed ankyrin repeat proteins. DARPin libraries with randomized potential target interaction residues, with diversities of over $10^{12}$ variants, have been generated at the DNA level. From these, DARPins can be selected for binding to a target of choice with picomolar affinity and specificity.

Affitins, or nanofitins, are artificial proteins structurally derived from the DNA binding protein Sac7d, found in *Sulfolobus acidocaldarius*. By randomizing the amino acids on the binding surface of Sac7d and subjecting the resulting protein library to rounds of ribosome display, the affinity can be directed towards various targets, such as peptides, proteins, viruses, and bacteria.

Anticalins are derived from human lipocalins which are a family of naturally binding proteins and mutation of amino acids at the binding site allows for changing the affinity and selectivity towards a target of interest. They have better tissue penetration than antibodies and are stable at temperatures up to 70° C.

Monobodies are synthetic binding proteins that are constructed starting from the fibronectin type III domain (FN3) as a molecular scaffold.

Based on the above, a synaptogyrin-3 inhibitor for use (in a method) according to the invention can be defined as those inhibitors specific to synaptogyrin-3 including those selected from the group consisting of an antisense oligonucleotide, a gapmer, a siRNA, a shRNA, an antisense oligonucleotide, a zinc-finger nuclease, a meganuclease, a TAL effector nuclease, a CRISPR-Cas effector, an antibody or a fragment thereof binding to synaptogyrin-3, an alphabody, a nanobody, an intrabody, an aptamer, a DARPin, an affibody, an affitin, an anticalin, and a monobody.

In one embodiment, the synaptogyrin-3 inhibitor for use (in a method) according to the invention is an inhibitor, in particular an inhibitor specific to synaptogyrin-3, capable of blocking binding of synaptogyrin-3 to the N-terminal region of the Tau protein.

In the above, "specific to synaptogyrin-3" is referring to the fact that the inhibitor is acting at the level of synaptogyrin-3 and not at the level of another protein or other neurological factor. Specificity can be ascertained by e.g. determining physical interaction of the inhibitor to synaptogyrin-3. In one of the aspects of current application, the synaptogyrin-3 inhibitor as referred to in current document is an inhibitor of the binding between synaptogyrin-3 and Tau, more particularly the N-terminal region of Tau. In more particular aspects, said inhibitor blocks the interaction between synaptogyrin-3 and the Tau protein.

In alternative aspects of current application, the synaptogyrin-3 inhibitor that is capable of inhibiting or blocking the interaction between synaptogyrin-3 and the (N-terminal region of) Tau protein, might act at the level of synaptogyrin-3 and at the level of another protein. A non-limiting example of said another protein is the Tau protein, more particularly the N-terminal region of Tau. In yet other alternative aspects, the synaptogyrin-3 inhibitor that is capable of inhibiting or blocking the interaction between synaptogyrin-3 and the (N-terminal region of) Tau protein, might act at the level of the (N-terminal region of) Tau protein and not at the level of synaptogyrin-3.

Synaptogyrin-3 and Fragments Thereof

In humans, 6 synaptogyrins have currently been identified. Synaptogyrin-1 comes in three isoforms (1a predominantly expressed in neurons of the central nervous system; 1b and 1c, not expressed in the central nervous system). Synaptogyrin-2 is not expressed in the brain, and synaptogyrin-3 is expressed in brain and placenta (Kedra et al. 1998, Human Genet 103:131-141). The full-length amino acid sequence of human synaptogyrin-3 (GenBank accession number 043761) is depicted below:

```
                                          (SEQ ID NO: 1)
MEGASFGAGR AGAALDPVSF ARRPQTLLRV ASWVFSIAVF

GPIVNEGYVN TDSGPELRCV FNGNAGACRF GVALGLGAFL

ACAAFLLLDV RFQQISSVRD RRRAVLLDLG FSGLWSFLWF

VGFCFLTNQW QRTAPGPATT QAGDAARAAI AFSFFSILSW

VALTVKALQR FRLGTDMSLF ATEQLSTGAS QAYPGYPVGS

GVEGTETYQS PPFTETLDTS PKGYQVPAY
```

Exposed intraneuronally, but at the outside of the presynaptic vesicle are the N- and C-termini as well as the loop between the $2^{nd}$ and $3^{rd}$ transmembrane regions; based on the annotations of GenBank accession number 043761, these regions are defined for human synaptogyrin-3 as: N-terminal region: amino acids 1-29, with amino acid sequence

```
                                          (SEQ ID NO: 2)
MEGASFGAGR AGAALDPVSF ARRPQTLLR;
```

Loop spanning 2$^{nd}$ and 3$^{rd}$ transmembrane region: amino acids 91-104, with amino acid sequence

```
                                        (SEQ ID NO: 3)
RFQQISSVRD RRA;
```

C-terminal region: amino acids 169-229, with amino acid sequence

```
                                        (SEQ ID NO: 4)
QRFRLGTDMS LFATEQLSTG ASQAYPGYPV GSGVEGTETY

QSPPFTETLD TSPKGYQVPA Y
```

The delineation of these regions can vary depending on the definition of the transmembrane regions: these are e.g. defined differently by Kedra et al. 1998 (Human Genet 103:131-141), which yields slightly different intraneuronally exposed regions. It is clear that such variation is within the scope of the current invention. Also within the scope of the invention are amino acid sequence variants as may exist due to allelic variation. Such variations are defined herein as "variants of the intraneuronally exposed regions of synaptogyrin-3", or as "variants of SEQ ID NO:2, SEQ ID NO:3 and/or SEQ ID NO:4".

Binding between synaptogyrin-3 and (the N-terminal sequence of) the tau protein is at the heart of the current invention. In this context, fragments of synaptogyrin-3 refer to the intraneuronally exposed regions of synaptogyrin-3 as discussed above. It has, however, not yet been fully elucidated how tau binds to synaptogyrin-3, but it can be envisaged this binding will involve one or more of the intraneuronally exposed regions. Compared to human synaptogyrin-1a (the only other isoform present in the brain), these intraneuronally exposed regions are remarkably different: the N-terminal regions share 36% identity, the loop regions share 59% identity, and the C-terminal regions share only 21% identity. This renders these regions excellent targets for designing synaptogyrin-3-specific interacting molecules including drug candidates.

In a further embodiment, and in case of the synaptogyrin-3 inhibitor being an antibody or fragment thereof, an alpha-body, a nanobody, an intrabody, an aptamer, a DARPin, an affibody, an affitin, an anticalin, or a monobody, this type of inhibitor is binding to at least one intraneuronally exposed region of synaptogyrin-3. In particular, the inhibitor is binding to one or more (one, any combination of 2, or all 3) intraneuronally exposed region of synaptogyrin-3 defined by SEQ ID NO:2, SEQ ID NO:3 or SEQ ID NO:4 or variants thereof (as defined above).

Tauopathic Disorders

The pathway leading from soluble and monomeric to hyperphosphorylated, insoluble and filamentous tau protein is at the centre of many human neurodegenerative diseases, collectively referred to as tauopathies (Spillantini & Goedert 2013, Lancet Neurol 12:609-622). Tauopathies are a diverse group of disorders all having in common their association with prominent accumulation of intracellular tau protein. The tau protein is abundantly expressed in the central nervous system. The group of tauopathies is growing as recently Huntington disease (Fernandez-Nogales et al. 2014, Nat Med 20:881-885) and chronic traumatic encephalopathy (CTE; McKee et al. 2009, J Neuropathol Exp Neurol 68,709-735) were added.

Different classifications of tauopathies exist. In one classification system, tauopathic disorders are divided in predominant Tau pathologies, tauopathies associated with amyloid deposition, and tauopathies associated with another pathology (Williams et al. 2006, Intern Med J 36:652-660). Predominant Tau pathologies include progressive supranuclear palsy (PSP), progressive supranuclear palsy-parkinsonism (PSP-P), Richardson's syndrome, argyrophilic grain disease, corticobasal degeneration, Pick's disease, frontotemporal dementia with parkinsonism associated with chromosome 17 (FTDP-17), post-encephalitic parkinsonism, Parkinson's disease complex of Guam, and Guadeloupean parkinsonism. Tauopathic disorders associated with amyloid deposition include Alzheimer's disease, Down's syndrome, dementia pugilistica, familial British dementia, and familial Danish dementia. Tauopathic disorders associated with another pathology include myotonic dystrophy, Hallevorden-Spatz disease, and Niemann Pick type C.

Another classification is based on the isoform type found in the aggregates although overlaps may exist: 4R tauopathies include progressive supranuclear palsy (PSP), corticobasal degeneration, tangle predominant dementia, and argyrophilic grain disease. 3R tauopathies include Pick disease, and 3R+4R tauopathies include Alzheimer's disease (Dickson et al. 2011, J Mol Neurosci 45:384-389; Murray et al. 2014, Alzheimer's Res Ther 6:1). The tau protein is discussed herein in more detail further below.

Further tauopathies include tangle-only dementia, white matter tauopathy with globular glial inclusions, subacute sclerosing panencephalitis, SLC9A6-related mental retardation, non-Guamanian motor neuron disease with neurofibrillary tangles, neurodegeneration with brain iron accumulation, Gerstmann-Sträussler-Scheinker disease, frontotemporal lobar degeneration, diffuse neurofibrillary tangles with calcification, chronic traumatic encephalopathy, amyotrophic lateral sclerosis of Guam, amyotrophic lateral sclerosis and parkinsonism-dementia complex, prion protein cerebral amyloid angiopathy, and progressive subcortical gliosis (Murray et al. 2014, Alzheimer's Res Ther 6:1; Spillantini & Goedert 2013, Lancet Neurol 12:609-622).

Symptoms of tauopathic disorders include clinical or pathological symptoms such as mild cognitive impairment, dementia, cognitive decline (e.g. apathy, impairment in abstract thought), decline of motor function (causing e.g. postural instability, tremor or dystonia), oculomotor and bulbar dysfunction. Criteria for diagnosing dementia are outlined in e.g. the Diagnostic and Statistical Manual of Mental Disorders (DSM) or in the International Classification of Disease (ICD) and are subject to regular updates. The type of clinical symptoms depends on which region of the brain is affected by the tauopathy and explains why Alzheimer's disease is mainly a dementing disease and why Parkinson's disease is mainly affecting movement. Stereotypical temporospatial propagation of tau inclusions creates a consistent pattern of brain lesions in at least Alzheimer's disease and argyrophilic grain disease. The spreading may in part occur in a trans-synaptic manner (Spillantini & Goedert 2013, Lancet Neurol 12:609-622; Liu et al. 2012, PloS One 7:e31802). Molecular symptoms of tauopathic disorders include synaptic dysfunction (in particular pre-synaptic dysfunction), neurotoxicity, neuronal degeneration, neuronal dysfunction, synapse loss, and amyloid deposition.

The synaptogyrin-3 inhibitor as described hereinabove is thus applicable for use in (a method for) treating or inhibition progression of a tauopathic disorder wherein the tauopathic disorder is selected from the group consisting of Alzheimer's disease, progressive supranuclear palsy (PSP), progressive supranuclear palsy-parkinsonism (PSP-P), Richardson's syndrome, argyrophilic grain disease, corticobasal degeneration Pick's disease, frontotemporal dementia with parkinsonism associated with chromosome 17 (FTDP-17), post-encephalitic parkinsonism, Parkinson's disease complex of Guam, Guadeloupean parkinsonism, Huntington disease, Down's syndrome, dementia pugilistica, familial British dementia, familial Danish dementia, myotonic dystrophy, Hallevorden-Spatz disease, Niemann Pick type C, chronic traumatic encephalopathy, tangle-only dementia, white matter tauopathy with globular glial inclusions, subacute sclerosing panencephalitis, SLC9A6-related mental retardation, non-Guamanian motor neuron disease with neurofibrillary tangles, neurodegeneration with brain iron accumulation, Gerstmann-Sträussler-Scheinker disease, frontotemporal lobar degeneration, diffuse neurofibrillary tangles with calcification, chronic traumatic encephalopathy, amyotrophic lateral sclerosis of Guam, amyotrophic lateral sclerosis and parkinsonism-dementia complex, prion protein cerebral amyloid angiopathy, and progressive subcortical gliosis.

The synaptogyrin-3 inhibitor as described hereinabove is thus likewise applicable for use in (a method for) treating or inhibition progression of a symptom of tauopathic disorder selected from the group of mild cognitive impairment, dementia, cognitive decline, decline of motor function, oculomotor and bulbar dysfunction, synaptic dysfunction, neurotoxicity, neuronal degeneration, neuronal dysfunction, synapse loss, and amyloid deposition. In particular, in relation to synaptic dysfunction it concerns pre-synaptic dysfunction.

"Treatment" refers to any rate of reduction or retardation of the progress of the disease or disorder compared to the progress or expected progress of the disease or disorder when left untreated. More desirable, the treatment results in no/zero progress of the disease or disorder (i.e. "inhibition" or "inhibition of progression") or even in any rate of regression of the already developed disease or disorder.

Tauopathies are in general progressive disorders, and progression may imply propagation of pathological tau protein (Asai et al. 2015, Nat Neurosci 18:1584-1593; deCalignon et al. 2012, Neuron 73:685-697).

Diagnosis of Tauopathic Disorders

Magnetic resonance imaging (MRI) in itself allows for radiologic determination of brain atrophy. Midbrain atrophic signs such as the Hummingbird or Penguin silhouette are for instance indicators of PSP. Determination of tau protein content in the cerebrospinal fluid (CSF) may also serve as an indicator of tauopathies. The ratio between the 33 kDa/55 kDa tau-forms in CSF was e.g. found to be reduced in a patients with PSP (Borroni et al. 2008, Neurology 71:1796-1803).

Recently, in vivo imaging techniques of neurodegeneration have become available. Such techniques can clearly support the clinical diagnosis of neurodegenerative diseases in general and of tauopathies in particular. In vivo diagnosis of tauopathies benefits from the existence of Tau imaging ligands detectable by positron emission tomography (PET), and include the radiotracers 2-(1-(6-((2-[$^{18}$F]fluoroethyl)(methyl) amino)-2-naphthyl)ethylidene) malononitrile ([$^{18}$F]FDDNP), 2-(4-aminophenyl)-6-(2-([$^{18}$F]fluoroethoxy))quinolone ([$^{18}$F]THK523), and [$^{18}$F]T807 and [$^{18}$F]T808 (Murray et al. 2014, Alzheimer's Res Ther 6:1). In addition, MRI can be used to detect tauopathies, and PET imaging with fluorodeoxyglucose (FDG, $^{18}$F agent) is indicative of synaptic activity (Murray et al. 2014, Alzheimer's Res Ther 6:1). Beta amyloid, that can be detected in vivo, e.g. by using florbetapir (or other amyloid markers) in combination with PET, proved to be an accurate biomarker for at least Alzheimer's disease (Clark et al. 2011, J Am Med Assoc 305:275-283) and the florbetapir-PET technique received FDA approval in 2012. The availability of in vivo tauopathy detection techniques is further supportive for selecting subjects that can benefit from synaptogyrin-3 inhibitory therapies as described herein.

Drug Administration Across Blood-Brain Barrier

The blood-brain barrier (BBB) is a protective layer of tightly joined cells that lines the blood vessels of the brain which prevents entry of harmful substances (e.g. toxins, infectious agents) and restricts entry of (non-lipid) soluble molecules that are not recognized by specific transport carriers into the brain. This poses a challenge in the delivery of drugs, such as the synaptogyrin-3 inhibitors described herein, to the central nervous system/brain in that drugs transported by the blood not necessarily will pass the blood-brain barrier. Although the BBB often is to some degree affected/broken down in case of a tauopathic disorder, it may be needed to rely on a means to enhance permeation of the BBB for a candidate drug for treating a tauopathic disorder to be able to enter the affected brain cells. Several options are nowadays available for delivery of drugs across the BBB (Peschillo et al. 2016, J Neurointervent Surg 8:1078-1082; Miller & O'Callaghan 2017, Metabolism 69:S3-S7; Drapeau & Fortin 2015, Current Cancer Drug Targets 15:752-768).

Drugs can be directly injected into the brain (invasive strategy) or can be directed into the brain after BBB disruption with a pharmacological agent (pharmacologic strategy). Invasive means of BBB disruption are associated with the risk of hemorrhage, infection or damage to diseased and normal brain tissue from the needle or catheter. Direct drug deposition may be improved by the technique of convection-enhanced delivery. Longer term delivery of a therapeutic protein (e.g. a neurotrophic factor or nerve growth factor, or a proteinaceous synaptogyrin-3 inhibitor as describe herein) can be achieved by implantation of genetically modified stem cells, by recombinant viral vectors, by means of osmotic pumps, or by means of incorporating the therapeutic drug in a polymer (slow release; can be implanted locally).

Pharmacologic BBB disruption has the drawback of being non-selective and can be associated with unwanted effects on blood pressure and the body's fluid balance. This is circumvented by targeted or selective administration of the pharmacologic BBB disrupting agent. As an example, intra-arterial cerebral infusion of an antibody (bevacizumab) in a brain tumor was demonstrated after osmotic disruption of the BBB with mannitol (Boockvar et al. 2011, J Neurosurg 114:624-632); other agents capable of disrupting the BBB pharmacologically include bradykinin and leukotriene C4 (e.g. via intracarotid infusion; Nakano et al. 1996, Cancer Res 56:4027-4031).

BBB transcytosis and efflux inhibition are other strategies to increase brain uptake of drugs supplied via the blood. Using transferrin or transferrin-receptor antibodies as carrier of a drug is one example of exploiting a natural BBB transcytosis process (Friden et al. 1996, J Pharmacol Exp Ther 278:1491-1498). Exploiting BBB transcytosis for drug delivery is also known as the molecular Trojan horse strategy. Another mechanism underlying BBB, efflux pumps or ATP-binding cassette (ABC) transporters (such as breast cancer resistance protein (BCRP/ABCG2) and P-glycoprotein (Pgp/MDR1/ABCB1)), can be blocked in order to increase uptake of compounds (e.g. Carcaboso et al. 2010, Cancer Res 70:4499-4508).

Therapeutic drugs can alternatively be loaded in liposomes to enhance their crossing of the BBB, an approach also known as liposomal Trojan horse strategy.

Especially in the field of treating cognitive and neurodegenerative disorders there has been quite some interest in intranasal delivery of drugs (e.g. Muhs et al. 2007, Proc Natl Acad Sci USA 104:9810-9815; Kao et al. 2000, Pharm Res 17:978-984; Hanson & Frey 2008, BMC Neurosci 9 (Suppl3): 55). This strategy is based on the trigeminal and olfactory nerves that innervate the nasal epithelium, representing direct connections between the external environment and the brain.

A more recent and promising avenue for delivering therapeutic drugs to the brain consists of (transient) BBB disruption by means of ultrasound, more particularly focused ultrasound (FUS; Miller et al. 2017, Metabolism 69:S3-S7). Besides being non-invasive, this technique has, often in combination with real-time imaging, the advantage of precise targeting to a diseased area of the brain. Therapeutic drugs can be delivered in e.g. microbubbles e.g. stabilized by an albumin or other protein, a lipid, or a polymer. Therapeutic drugs can alternatively, or in conjunction with microbubbles, be delivered by any other method, and subsequently FUS can enhance local uptake of any compound present in the blood (e.g. Nance et al. 2014, J Control Release 189:123-132). Just one example is that of FUS-assisted delivery of antibodies directed against toxic amyloid-beta peptide with demonstration of reduced pathology in mice (Jordao et al. 2010, PloS One 5:e10549). Microbubbles with a therapeutic drug load can also be induced to burst (hyperthermic effect) in the vicinity of the target cells by means of FUS, and when driven by e.g. a heat shock protein gene promoter, localized temporary expression of a therapeutic protein can be induced by ultrasound hyperthermia (e.g. Lee Titsworth et al. 2014, Anticancer Res 34:565-574). Alternatives for ultrasound to induce the hyperthermia effect are microwaves, laser-induced interstitial thermotherapy, and magnetic nanoparticles (e.g. Lee Titsworth et al. 2014, Anticancer Res 34:565-574).

Intracellular Drug Administration

Besides the need to cross the BBB, drugs targeting disorders of the central nervous system, such as the synaptogyrin-3 inhibitors described herein, may also need to cross the cellular barrier. One solution to this problem is the use of cell-penetrating proteins or peptides (CPPs). Such peptides enable translocation of the drug of interest coupled to them across the plasma membrane. CPPs are alternatively termed Protein Transduction Domains (TPDs), usually comprise 30 or less (e.g. 5 to 30, or 5 to 20) amino acids, and usually are rich in basic residues, and are derived from naturally occurring CPPs (usually longer than 20 amino acids), or are the result of modelling or design. A non-limiting selection of CPPs includes the TAT peptide (derived from HIV-1 Tat protein), penetratin (derived from *Drosophila* Antennapedia—Antp), pVEC (derived from murine vascular endothelial cadherin), signal-sequence based peptides or membrane translocating sequences, model amphipathic peptide (MAP), transportan, MPG, polyarginines; more information on these peptides can be found in Torchilin 2008 (Adv Drug Deliv Rev 60:548-558) and references cited therein. The commonly used CPP is the transduction domain of TAT termed TATp, defined by the amino acid sequence YGRKKRRQRRR (SEQ ID NO: 5). The MAP peptide is defined by the amino acid sequence KLALKLALKALKAALKLA (SEQ ID NO:6), and the penetratin peptide by RQIKIWFQNRRMKWKK (SEQ ID NO:7). The TAT peptide was e.g. used to shuffle a tau-fragment into neuronal cells (Zhou et al. 2017).

CPPs can be coupled to carriers such as nanoparticles, liposomes, micelles, or generally any hydrophobic particle. Coupling can be by absorption or chemical bonding, such as via a spacer between the CPP and the carrier. To increase target specificity an antibody binding to a target-specific antigen can further be coupled to the carrier (Torchilin 2008, Adv Drug Deliv Rev 60:548-558)

CPPs have already been used to deliver payloads as diverse as plasmid DNA, oligonucleotides, siRNA, peptide nucleic acids (PNA), proteins and peptides, small molecules and nanoparticles inside the cell (Stalmans et al. 2013, PloS One 8:e71752).

Methods for Identifying Synaptogyrin-3 Inhibitors

In another aspect, the invention relates to methods for identifying synaptogyrin-3 inhibitors described hereinabove. Compounds tested in the methods for identifying synaptogyrin-3 inhibitors do not necessarily be pre-screened for their specificity towards synaptogyrin-3 (e.g. by using a binding assay). When not pre-screened, the candidate synaptogyrin-3 inhibitors identified in an assay as described herein need to undergo a further screening in order to identify synaptogyrin-3-specific compounds.

In first instance methods are described for identifying or for screening for synaptogyrin-3 inhibitors that inhibit synaptogyrin-3 at the functional level (and thus not at the genetic level or level of expression).

Thus one in vitro method for identifying a synaptogyrin-3 inhibitor, is a method comprising the steps of:
  i) providing synaptogyrin-3, or a fragment of synaptogyrin-3 comprising one or more of the intraneuronally exposed regions of synaptogyrin-3;
  ii) providing Tau protein, or a fragment of Tau comprising the N-terminal region;
  iii) providing a compound that is candidate for being a synaptogyrin-3 inhibitor;
  iv) contacting the synaptogyrin-3 or fragment thereof provided in i) with the Tau protein or fragment thereof provided in ii) in the presence or absence of the compound provided in iii);
  v) identifying from iv) a compound that is, compared to identical conditions but for the absence of the compound, reducing binding of the Tau protein or fragment thereof to synaptogyrin-3 or fragment thereof; and
  vi) identifying, from v), as inhibitor of synaptogyrin-3 a compound that is specifically binding to the synaptogyrin-3 or fragment thereof.

A variant in vitro method for identifying a synaptogyrin-3 inhibitor, is a method comprising the steps of:
  i) providing synaptogyrin-3, or a fragment of synaptogyrin-3 comprising one or more of the intraneuronally exposed regions of synaptogyrin-3;
  ii) providing Tau protein, or a fragment of Tau comprising the N-terminal region;
  iii) providing a synaptogyrin-3-specific compound that is candidate for being a synaptogyrin-3 inhibitor;
  iv) contacting the synaptogyrin-3 or fragment thereof provided in i) with the Tau protein or fragment thereof provided in ii) in the presence or absence of the compound provided in iii);
  v) identifying as synaptogyrin-3 inhibitor, from iv) a compound that is, compared to identical conditions but for the absence of the compound, reducing binding of the Tau protein or fragment thereof to synaptogyrin-3 or fragment thereof.

In one of the further embodiments to these methods the synaptogyrin-3 or fragment thereof can be provided on e.g. isolated synaptic vesicles, on virus-like particles, in liposomes, or in displayed by baculoviruses (Hamakubo et al. 2014, Biochim Biophys Acta 1844:1920-1924). The tau protein or fragment thereof can be immobilized on a solid carrier, such as a magnetic carrier. Alternatively, the synaptic vesicle, the virus-like particle or the liposome functioning as carrier of the synaptogyrin-3 or fragment thereof is immobilized on a solid carrier. In a further alternative, the synaptogyrin-3 or fragment thereof and the Tau protein or fragment thereof is provided in a neuronal cell.

The current document also provides a method for identifying an inhibitor of the interaction or binding between Synaptogyrin-3 and Tau, comprising expressing Synaptogyrin-3 and Tau in a cell, wherein the interaction or binding between Synaptogyrin-3 and Tau generates a measurable signal and wherein a compound is identified as an inhibitor of the interaction or binding between Synaptogyrin-3 and Tau when said measurable signal is smaller (or lower) in the presence of said compound than in the absence of said compound. A non-limiting example of measuring the interaction or binding between Synaptogyrin-3 and Tau is by use of luminescence as explained in Example 2.4 of current document. In one aspect, Synaptogyrin-3 and Tau are expressed in cells, particularly in human cells, more particularly in HEK cells. In particular aspects, said measurable signal of the Syngr-3/Tau interaction or binding is at least 10%, at least 20%, at least 30%, at least 40%, at least 50%, at least 60%, at least 70%, at least 80%, at least 90%, at least 100%, at least 2-fold, at least 3-fold, at least 5-fold or at least 10-fold smaller (or lower) in the presence of said compound than in the absence of said compound.

"Synaptic vesicles" provided in said in vitro system are defined as small secretory vesicles that contain a neurotransmitter, and are naturally abundantly present organelles of a uniform size inside an axon near the presynaptic membrane. The vesicles have a diameter of about 40 nm and accommodate a number of proteins and phospholipids. In physiological context, when a nerve impulse moves down the axon of a neuron and arrives at an axon terminal, it stimulates synaptic vesicles in the terminal to discharge neurotransmitters. After fusion with the membrane, a synaptic vesicle releases its contents into the synaptic cleft (Dillon & Goda 2005, Annu Rev Neurosci 28: 25-55). The production of virus-like particles as carrier of transmembrane proteins has been described (e.g. Zemanova et al. 2004, Biochemistry 43:9021-9028; Eyckerman et al. 2016, Nat Commun 7:11416).

In the above methods, the binding of the synaptogyrin-3 or fragment thereof to the Tau protein or fragment thereof can be determined by any suitable detection method including luminescent, fluorescent, immunologic or radiologic detection, co-sedimentation, co-immunoprecipitation, or electron microscopy (see e.g. methods as described in Zhou et al. 2017, or as described in the Examples herein).

In these and further methods for identifying synaptogyrin-3 inhibitors, "reducing binding" is obtained when binding of synaptogyrin-3 or fragment thereof to the Tau protein or fragment thereof is at least 20%, at least 30%, at least 40%, at least 50%, at least 60%, at least 70%, at least 80%, at least 90%, at least 95% or even 100% weaker as compared to the normal (100%) binding of the synaptogyrin-3 or fragment thereof to the Tau protein or fragment thereof in the absence of any inhibitor.

Compounds tested in the methods for identifying synaptogyrin-3 inhibitors are not limited to a specific type of the compound. In one embodiment, compound libraries (comprising at least two different compounds) are screened. Compound libraries are a large collection of stored compounds utilized for high throughput screening. Compounds in a compound library can have no relation to one another, or alternatively have a common characteristic. For example, a hypothetical compound library may contain all known compounds known to bind to a specific binding region. As would be understood by one skilled in the art, the methods of the invention are not limited to the types of compound libraries screened. For high-throughput screening, compound libraries may be used. Examples include, but are not limited to, natural compound libraries, allosteric compound libraries, peptide libraries, antibody fragment libraries, synthetic compound libraries, combinatorial chemical libraries etc. In one embodiment, high throughput screening methods involve providing a library containing a large number of compounds (candidate compounds) potentially having the desired activity. Such libraries are then screened in one or more assays, as described herein, to identify those library members that display the desired characteristic activity. The compounds thus identified can serve as conventional "hit compounds" or can themselves be used as potential or actual therapeutics.

In relation to these and further methods for identifying synaptogyrin-3 inhibitors, "synaptogyrin-3 or fragment thereof" has been described above; "tau protein or fragment of tau comprising the N-terminal region" is described hereafter.

Tau Protein and Fragments Thereof

The human tau protein in the brain is a collection of 6 isoforms generated through alternative splicing. The 6 isoforms lack or contain a different number of near-amino-terminal inserts ("N": 0N, 1N or 2N) and lack or contain "R2", one of the 4 repeats in the microtubule-binding domain. This yields the 6 variants, from the longest (splicing name 2N4R; 441 amino acids) to the shortest variant (splicing name 0N3R; 352 amino acids), with 4 intermediate variants (1N4R: 412 amino acids; 0N4R: 383 amino acids; 2N3R: 410 amino acids; 1N3R: 381 amino acids) (e.g. Wang & Mandelkow 2016).

As shown herein, the N-terminal sequence of the tau protein is of importance in view of its interaction with synaptogyrin-3. In the context of the present invention, fragments of tau refer to fragments comprising at least the N-terminal part of tau. It has, however, not yet been fully elucidated which part of tau's N-terminus is required for binding to synaptogyrin-3, so only by way of example, the N-terminal amino acid sequence (more particularly the N-terminal 112 amino acids) of the human tau 0NxR (wherein x=3 or 4) isoform is depicted below, as well as the same sequence in which the N1 repeat is inserted (1NxR), or in which the N1 and N2 repeats are inserted (2NxR).

Human tau isoform 0NxR, N-terminal 112 amino acids (Goedert et al. 1989, EMBO J 8:393-399)

(SEQ ID NO: 8)
MAEPRQEFEV MEDHAGTYGL GDRKDQGGYT MHQDQEGDTD

AGLKAEEAGI GDTPSLEDEA AGHVTQARMV SKSKDGTGSD

DKKAKGADGK TKIATPRGAA PPGQKGQANA TR

Human tau isoform 1NxR, N-terminal 112 amino acids of isoform 0NxR containing the N1 amino-terminal insert (underlined; Goedert et al. 1989, Neuron 3:519-526)

(SEQ ID NO: 9)
MAEPRQEFEV MEDHAGTYGL GDRKDQGGYT MHQDQEGDTD

AGLKESPLQT PTEDGSEEPG SETSDAKSTP TAEAEEAGIG

DTPSLEDEAA GHVTQARMVS KSKDGTGSDD KKAKGADGKT

KIATPRGAAP PGQKGQANAT R

Human tau isoform 2NxR, N-terminal 112 amino acids of isoform 0NxR containing the N1 and N2 amino-terminal inserts (Goedert et al. 1989, Neuron 3:519-526)

(SEQ ID NO: 10)
MAEPRQEFEV MEDHAGTYGL GDRKDQGGYT MHQDQEGDTD

AGLKESPLQT PTEDGSEEPG SETSDAKSTP TAEDVTAPLV

DEGAPGKQAA AQPHTEIPEG TTAEEAGIGD TPSLEDEAAG

HVTQARMVSK SKDGTGSDDK KAKGADGKTK IATPRGAAPP

GQKGQANATR

In second instance methods are described for identifying or for screening for synaptogyrin-3 inhibitors that inhibit synaptogyrin-3 at the genetic level or level of expression (and thus not at the functional level).

In particular, an in vitro method for identifying a synaptogyrin-3 inhibitor is provided wherein said method is comprising the steps of:
  i) providing cells expressing synaptogyrin-3 or a fragment of synaptogyrin-3 comprising one or more of the intraneuronally exposed regions of synaptogyrin-3;
  ii) providing a synaptogyrin-3-specific compound that is candidate for being an inhibitor of synaptogyrin-3 expression;
  iii) administering a compound provided in ii) to the cells provided in i); and
  iv) identifying as synaptogyrin-3 inhibitor, from iii), a compound provided in ii) that is, compared to identical conditions but for the absence of the compound, reducing expression of synaptogyrin-3 or fragment thereof.

In one embodiment, the cells expressing synaptogyrin-3 or fragment thereof are neuronal cells or stem cells of non-embryogenic origin (e.g. derived from single blastomers as described by Chung et al. 2008, Cell Stem Cell 2:113-118, or parthenogenetic activated unfertilized oocytes).

In these and further methods for identifying synaptogyrin-3 inhibitors, "reducing expression" is obtained when expression of synaptogyrin-3 or fragment thereof is at least 20%, at least 30%, at least 40%, at least 50%, at least 60%, at least 70%, at least 80%, at least 90%, at least 95% or even 100% weaker as compared to the normal (100%) expression of the synaptogyrin-3 or fragment thereof in the absence of any inhibitor.

Other Definitions

The present invention is described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. Unless specifically defined herein, all terms used herein have the same meaning as they would to one skilled in the art of the present invention. Practitioners are particularly directed to Sambrook et al., Molecular Cloning: A Laboratory Manual, 4th ed., Cold Spring Harbor Press, Plainsview, N.Y. (2012); and Ausubel et al., current Protocols in Molecular Biology (Supplement 100), John Wiley & Sons, New York (2012), for definitions and terms of the art. The definitions provided herein should not be construed to have a scope less than understood by a person of ordinary skill in the art.

The term "defined by SEQ ID NO:X" as used herein refers to a biological sequence consisting of the sequence of amino acids or nucleotides given in the SEQ ID NO:X. For instance, an antigen defined in/by SEQ ID NO:X consists of the amino acid sequence given in SEQ ID NO:X. A further example is an amino acid sequence comprising SEQ ID NO:X, which refers to an amino acid sequence longer than the amino acid sequence given in SEQ ID NO:X but entirely comprising the amino acid sequence given in SEQ ID NO:X (wherein the amino acid sequence given in SEQ ID NO:X can be located N-terminally or C-terminally in the longer amino acid sequence, or can be embedded in the longer amino acid sequence), or to an amino acid sequence consisting of the amino acid sequence given in SEQ ID NO:X.

EXAMPLES

1. Experimental Procedures 1.1. Isolation of Synaptic Vesicles from Human, Mouse and Fly Brain The use of human tissue samples conformed to national and institutional ethics guidelines and was approved by the Edinburgh Brain Bank Ethics Committee and the Academic and Clinical Central Office for Research and Development medical research ethics committee. Case information for all patient samples used in this study is included in Table S1. All animal experiments were performed with ethical permission from and under the guidelines of the KU Leuven animal ethics committee. Isolation of crude synaptic vesicles (LP2 fraction) from mammalian brain or *Drosophila* adult fly brain was performed based on protocols (Ahmed et al., 2013) and (Depner et al., 2014), respectively, with modifications. For detailed fractionation centrifugation speeds and times see the respective schematics presented in FIGS. 5 and 6. All steps of fractionation experiments were carried out on ice or at 4° C. Aliquots of pellets were saved at various steps during fractionation and were lysed in RIPA buffer (150 mM NaCl, 1.0% IGEPAL CA-630/NP-40, 0.5% sodium deoxycholate, 0.1% SDS, 50 mM Tris, pH 8.0, Sigma) containing protease and phosphatase inhibitors and stored at −80° C. until analysis. Briefly, frozen (human) or fresh (mouse) brain tissue was chopped into 5 mm$^2$ cubes, and homogenized in sucrose buffer (320 mM sucrose, 4 mM HEPES pH 7.4, 1× Complete protease inhibitor cocktail (Roche), 1× PhosStop phosphatase inhibitor cocktail (Roche) at a volume of 9 mL per 1 g human brain sample or 3 mL per six-week-old mouse brain (C57BL/6 strain). For fly brains, 5 mL of sieved and collected fly heads were ground in a liquid nitrogen-cooled mortar with a pestle into fine powder and resuspended in 15 mL sucrose buffer per 5 mL adult fly heads. Homogenization was performed using 10 strokes at 600 pm (human and mouse brain) or 900 rpm (fly brain) in a Teflon glass homogenizer. Following pelleting of cell debris and nuclei, synaptosomes were isolated and washed once by resuspension in 10 mL sucrose buffer and re-pelleted. Synaptosomes were hypotonically lysed by resuspension of the synaptosome pellet in 10 volumes of HEPES-buffered water (5 mM HEPES pH 7.4, 1× Protease inhibitor cocktail, 1× Phosphatase inhibitor cocktail and Pepstatin A (Roche, fly samples) and incubated for 30 min at 4° C. with rotation. For fly brains, the osmotic shock suspension was homogenized using 3 strokes at 2000 rpm. Following osmotic shock, a 25,000×g centrifugation step removed mitochondria and large synaptic membrane debris; finally, synaptic vesicles were collected from the supernatant by centrifugation at 165,000×g for 2 h. The resulting crude synaptic vesicle pellet (LP2/SV) was resuspended in SV resuspension buffer (5 mM HEPES pH 7.4, 300 mM glycine) and frozen in aliquots at −80° C. Vesicles were quantified according to protein content using the Bradford Quick Start reagent (Bio-Rad). The purity of the LP2/SV fraction was verified by immunoblotting 20 µg of protein from fractionation pellets (lysed in RIPA buffer) or 20 µg vesicle suspension for synaptic vesicle markers or contaminates.

1.2. SDS-PAGE and Immunoblotting

For denaturation of protein samples, 4× lithium dodecyl sulfate (LDS, Invitrogen) was added to samples to a final concentration of 1× supplemented with 1% β-mercaptoethanol and denatured for 10 min at 70-80° C. Protein samples were separated on NuPAGE 10%, 12% or 4-12% Bis-Tris mini polyacrylamide gels in MOPS buffer (Invitrogen), or 4-15% Bis-Tris Criterion TGX midi protein gels in Tris-Glycine-SDS buffer (Bio-Rad). For colloidal coomassie staining, gels were stained with PageBlue staining solution (Thermo Fisher) according to manufacturer's instructions. For immunoblotting, protein gels were transferred to nitrocellulose membranes using the TransBlot Turbo transfer system (Bio-Rad). Membranes were blocked in TBS-T (1× Tris-Buffered Saline solution+0.05% Tween-20) with 5% (w/v) milk powder for 30-60 min at room temperature. Primary antibodies were diluted in blocking buffer (see Table 1 below) and incubated with membranes for 1-2 h at room temperature or overnight at 4° C., followed by 4×10 min washing in TBS-T. Secondary HRP-conjugated antibodies (Jackson Immunoresearch) were diluted 1:10,000 in blocking buffer and incubated with membranes for 1 h at room temperature, then washed for 6×10 min in TBS-T. Immunoblots were developed using the Western Lightning Plus enhanced chemiluminescence kit (Perkin Elmer) and imaged on a Fuji Film imaging system. Densitometry analysis was performed using Image Studio Lite.

TABLE 1

Antibodies used in this study. Dilutions used for immunoblotting (IB) or immunohistochemistry (IHC) are given.

| Target | Host Species | Dilution for IB | Dilution for IHC | Supplier or Reference | Product Number |
|---|---|---|---|---|---|
| Actin | Mouse | 1:5000 | — | DSHB | JLA20 |
| ATP Synthase | Mouse | 1:10000 | — | Abcam | ab14730 |
| Drosophila Cysteine String Protein (CSP) | Mouse | 1:5000 | 1:1000 | DSHB | DCSP-2 (6D6) |
| Drosophila Discs-large (Dlg) | Mouse | 1:5000 | — | DSHB | 4F3 |
| Drosophila Synaptogyrin (Syngr) | Rabbit | 1:10000 | — | Troy Littleton Lab (R. J. Stevens et al., 2012) | |
| GAPDH | Mouse | 1:5000 | — | EMD Millipore | MAB374 (Clone 6C5) |
| His Tag | Mouse | 1:10000-1:1000 | — | Thermo Fisher | 37-2900 (Clone 4A12E4) |
| Human Tau "hTau" (HT7) | Mouse | — | 1:500 | Thermo Fisher | MN1000 |
| MAP2 | Chicken | — | 1:2000 | Abcam | ab5392 |
| Munc18-1 (Munc18) | Rabbit | 1:5000 | — | Cell Signaling | 13414 (D4O6V) |
| phospho-Tau pSer202/pThr205 (AT8) | Mouse | 1:1000-1:500 | — | Thermo Fisher | MN1020 |
| phospho-Tau pSer396/pSer404 (PHF-1) | Mouse | 1:5000-1:1000 | — | Peter Davies Lab (Greenberg et al., 1992; Otvos et al., 1994) | |
| PSD-95 | Rabbit | 1:10000 | — | Cell Signaling | 3450T (D27E11) |
| Synapsin-1 (Syn) | Rabbit | 1:10000 | 1:500 | EMD Millipore | AB1543P |
| Synaptic vesicle glycoprotein 2A (SV2) | Mouse | 1:5000 | — | DSHB | 5V2 |
| Synaptobrevin-2/VAMP2 (Syb) | Mouse | 1:10000 | — | Synaptic Systems | 104 211 (Clone 69.1) |
| Synaptogyrin-3 (Syngr3), C-terminus | Mouse | 1:50001 | 1:500 | Santa Cruz Biotechnology | sc-271046 (Clone E-11) |
| Synaptogyrin-3 (Syngr3), C-terminus | Rabbit | 1:5000 | 1:500 | Novus Biologicals | NBP2-30475 |
| Synaptophysin-1 (Syph) | Mouse | 1:10000 | 1:500 | Synaptic Systems | 101 011 (Clone 7.2) |
| Synaptotagmin-1 (Syt) cytoplasmic epitope | Mouse | 1:10000 | — | DSHB | mAb 48 (asv 48) |
| Synaptotagmin-1 (Syt) vesicular epitope | Rabbit | 1:1000 | — | Synaptic Systems | 105 102 |
| Total Tau (DAKO) | Rabbit | 1:10000-1:5000 | 1:1000 | DAKO | A002401 |
| VGlut1 | Guinea Pig | — | 1:500 | EMD Millipore | AB5905 |

DSHB: Developmental Studies Hybridoma Bank

1.3. Purification of Recombinant Human Tau

The purification of soluble recombinant human Tau from bacteria was described previously (Zhou et al., 2017). The cDNA sequences encoding human full-length Tau (0N4R isoform, 383 aa) or ΔN_Tau (aa 113-383) were cloned behind a N-terminal GST tag and PreScission Protease cleavage sequence in the pGEX-6P-1 plasmid and was followed by a C-terminal 8×-His tag (inserted into the reverse amplification primer). Sequence-verified plasmids were transformed into Rosetta bacteria (Novagen) and maintained in medium containing ampicillin and chloramphenicol. Overnight pre-cultures were diluted 1:10 into LB medium, incubated for 2 h at 37° C. to exponential phase, and then expression was induced by addition of IPTG to a final concentration of 0.4 mM. Expression was carried out for 2 h at 37° C., followed by pelleting of cells (5,000×g for 15 min); cell pellets were stored at −80° C. until use. For purification, all steps were carried out on ice or at 4° C. A 50 mL cell pellet was resuspended in 1.5 mL lysis buffer (1× PBS supplemented with 1× protease inhibitor cocktail, Lysozyme, Benzonase, 1% Triton-X-100, and 10% glycerol) and incubated for 30 min at 4° C. with mixing. Lysates were clarified by centrifugation at 16,000×g for 20 min, then incubated with 150 μL washed Glutathione Sepharose 4B (GE Healthcare) for 2 h at 4° C. Glutathione Sepharose beads were washed 3 times with PBS supplemented with 250 mM NaCl, and 2 times with PreScission Protease cleavage buffer (20 mM Tris-HCl pH 7.0, 50 mM NaCl, 0.5 mM EDTA, 1 mM DTT, 0.01% Tween-20). Beads were incubated overnight at 4° C. with GST-tagged PreScission Protease (GE Healthcare) in cleavage buffer to remove the N-terminal GST tag and liberate Tau from the Sepharose beads. The next morning, the supernatant was incubated for 1 h with 75 μL fresh, washed Glutathione Sepharose to remove any unbound protease or uncleaved Tau. Cleaved Tau-8×His was then purified against the C-terminal His tag by incubation with 50 uL Ni-NTA resin (Bio-Rad) for 45 min, then washed 3× in His wash buffer (50 mM NaH$_2$PO$_4$ pH 8.0, 300 mM NaCl, 20 mM imidazole), and eluted by incubation with His elution buffer for 15 min (same buffer with 250 mM imidazole). Purified Tau was concentrated using an Amicon Centrifugal Filter unit with 10 kDa molecular weight cut-off (Millipore) and quantified using the Bradford Quick Start reagent. Using this method, purification of one 50 mL cell pellet yields approximately 8 μg of soluble Tau with >95% purity. For all experiments, Tau was always purified freshly and used immediately upon finishing purification.

1.4. In Vitro Synaptic Vesicle Binding Assays.

The ability of purified recombinant Tau to bind isolated synaptic vesicles in vitro was assessed using a vesicle sedimentation assay (Piccoli et al., 2014; Zhou et al., 2017). In this assay, 500 ng of freshly purified Tau-8×His was incubated together with 20 μg (according to protein) isolated synaptic vesicles in 100 μL SV binding buffer (4 mM HEPES pH 7.4, 5 mM Tris-HCl pH 7.4, 220 mM glycine, 30 mM NaCl, 1× protease inhibitor cocktail) for 2 h at 4° C. with rotation. The 100 μL binding reaction was then diluted into 600 μL binding buffer to prevent tubes from breaking during centrifugation. Vesicles were pelleted by ultracentrifugation at 165,000×g for 1 h, and the pellet was resuspended and denatured in 1×LDS sample buffer. The presence of Tau co-sedimenting together with synaptic vesicles (detected by immunoblotting of the vesicle pellet with anti-His antibody) indicates binding.

Limited proteolysis of synaptic vesicles was carried out by incubating 75 μg synaptic vesicles together with 50 μL sepharose-coupled TPCK-treated trypsin (Thermo Fisher) for 3 h at 37° C. After 3 h, proteolysis was halted by the addition of 1× protease inhibitor cocktail, 1 mM PMSF, and 0.5 mg/mL soybean trypsin inhibitor (Sigma) and the sepharose-conjugated trypsin was removed by centrifugation at 3,000×g to remove the sepharose slurry. As a control, untreated vesicles were incubated at 37° C. for 3 h but in the absence of trypsin.

To remove peripheral synaptic vesicle-associated proteins, vesicles were stripped with carbonate (Brose et al., 1995). Isolated synaptic vesicles were diluted in buffer containing 100 mM Na$_2$CO$_3$ pH 11 and 1× protease inhibitors and incubated at 4° C. for 30 min. Vesicles were pelleted by ultracentrifugation at 165,000×g for 1 h then resuspended in neutral buffer (5 mM HEPES pH 7.4, 300 mM glycine). As a control, unstripped vesicles were handled the same except diluted in neutral buffer instead of carbonate buffer. Equal volumes of untreated or carbonate-stripped vesicles were introduced into the binding reaction.

1.5. Liposome Flotation Assay.

The liposome flotation assay is based on a protocol previously described (Bigay et al., 2005). To generate small protein-free liposomes 0.25 mg of bovine brain Folch-fraction lipid extract (Avanti Lipids) was dried under a nitrogen stream and desiccated overnight in a vacuum chamber. Liposomes of 30-60 nm diameter were generated by adding 2504 warmed SV binding buffer to the lipid film and sonicating for 5 min in a 37° C. bath. Electron microscopy verified uniform 30-60 nm diameter of liposomes. 64 μg of liposomes was mixed together with 1.5 μg freshly purified Tau in 150 μL SV binding buffer and incubated together for 1 h at 4° C. After 1 h, the density of the binding reaction was adjusted to 30% (w/v) sucrose by addition of 100 μL of a 75% sucrose solution. The 250 μL binding reaction in 30% sucrose was overlaid with a middle 200 μL layer of 25% sucrose and a top layer of 50 μL SV buffer (no sucrose). The gradient was centrifuged at 240,000×g for 1 h at 4° C., and then 30 μL fractions from the bottom, middle, or top layers were collected, denatured with LDS and immunoblotted for Tau with anti-His antibodies. Due to their density, liposomes rise to the top sucrose-free fraction during centrifugation, together with any proteins bound to them. Thus, immunoblotting for protein present in the top fraction indicates binding to liposomes.

1.6. Identification of Synaptic Vesicle Protein Interactors by Mass Spectrometry.

Synaptic vesicles isolated from mouse brains (LP2/SV fraction) were lysed in 2% Triton-X-100 in SV resuspension buffer (5 mM HEPES pH 7.4, 300 mM glycine) for 1 h at 4° C., followed by clearing of membrane debris and intact vesicles by centrifugation at 165,000×g for 1 h. The SV lysate was diluted in SV binding buffer to a final concentration of 0.6% Triton-X-100 and supplemented with fresh protease inhibitors and NaCl to a final concentration of 100 mM. For co-immunoprecipitation, 2 μg of purified Tau$^{FL}$-8×His or Tau$^{ΔN}$-8×His was bound to 25 μL of washed Protein G Dynabeads (Invitrogen) using 1 μg mouse anti-His IgG antibody (Thermo Fisher, clone 4A12E4) for 2 h at 4° C. Beads were washed twice then incubated with SV lysate (330 μg protein per reaction, 0.6% Triton-X-100, 100 mM NaCl) in SV buffer with 1% BSA and fresh protease inhibitors overnight at 4° C. with rotation. As a negative control, we incubated SV lysate together with Dynabeads containing only the anti-His IgG antibody. After the overnight incubation, beads were washed three times with SV buffer+0.6% Triton-X-100 and three times with SV buffer to remove detergents. Samples were immediately processed for mass spectrometry.

Intact Tau-protein complexes were processed using on-bead digestion by overnight incubation with 0.2 mg/mL Trypsin in buffer containing 50 mM ammonium bicarbonate at 37° C. The resulting peptide mixture was dried in a SpeedVac, and the peptide pellet was resuspended in loading solvent (2% acetonitrile, 0.1% trifluoroacetic acid). $1/10^{th}$ of each sample was run in triplicate by LC-MS/MS by 30 min separation on a 2-50% gradient of solvent (80% acetonitrile, 19.9% water and 0.1% formic acid) coupled to a LTQ-Orbitrap XL mass spectrometer. Peptide spectra were searched with Mascot Daemon software against a *Mus musculus* protein database to identify proteins. The unfiltered mass spectrometry dataset is shown in Table S2. Identified proteins were cross-referenced against comprehensive lists of synaptic vesicle proteins (Burré et al., 2006; Takamori et al., 2006) and were classified as transmembrane SV proteins, peripheral SV proteins, or non-SV proteins (likely contaminates). A filtered list of identified SV-specific proteins absent in the negative control is shown in FIG. 1I. Mass spectrometry experiments were performed at the VIB Proteomics Expertise Center (University of Ghent, Belgium).

1.7. *Drosophila* Stocks and Genetics

*Drosophila melanogaster* fly stocks were handled using standard protocols. All experimental crosses involving the UAS/Gal4 bipartite expression system were kept at 25° C. to induce transgene expression. Experiments at the neuromuscular junction (NMJ) utilized the motorneuron-specific driver D42-Gal4.

We previously described the generation and characterization of wild-type or FTDP-17 clinical mutant 0N4R (383 aa) Tau variants (P301L, V337M, R406W) or N-terminally truncated ΔN_Tau mutants into the 68A4 locus on chromosome III (Zhou et al., 2017). All transgenic flies were kept on the w1118 strain background. The D42-Gal4 driver was recombined together with UAS-Tau genes onto chromosome III and, where necessary, additionally combined with the $syngr^1$ loss-of-function allele on chromosome II (to give heterozygous $syngr^{+/-}$) or UAS-Synaptotagmin-eGFP on chromosome II. Syngr KO flies ($syngr^1$ loss-of-function allele, w1118 background) were previously generated by and gifted from the J. Troy Littleton lab (R. J. Stevens et al., 2012). Control crosses were to wild-type w1118 strain for consistency of the genetic background. The UAS-Synaptotagmin-eGFP stock was obtained from the Bloomington Stock Center (stock 6925) and the UAS-syngr shRNA stock is HMS01724 from the *Drosophila* Transgenic RNAi project (TRiP, Bloomington stock 38274). Other loss-of-function/knock-down alleles and stocks used in the SV interactor genetic screen include $syt^{AD4}$ (DiAntonio et al., 1993), $synj^2$ (Verstreken et al., 2003), UAS-rph shRNA (TRiP JF01970, Bloomington stock 25950), $shi^{12-12B}$ (Kasprowicz et al., 2014), and $pnut^{XP}$ (Bloomington stock 5687).

1.8. Immunohistochemistry of *Drosophila* Larvae

For immunohistochemistry at *Drosophila* larval NMJs, wandering third-instar larvae were dissected in freshly prepared HL3 buffer (110 mM NaCl, 5 mM KCl, 10 mM $NaHCO_3$, 5 mM HEPES, 30 mM sucrose, 5 mM trehalose, 10 mM $MgCl_2$, pH 7.4) on Sylgard-coated plates then fixed in HL3+3.7% formaldehyde for 20 min at room temperature. Larval filets were transferred to microcentrifuge tubes, washed with PBS and permeabilized with PBS+0.4% Triton-X-100 for 1 h at room temperature then blocked for 1 h in blocking buffer (PBS+1% BSA+0.4% Triton-X-100). Primary antibody incubation was performed overnight (1:1000 dilution, see antibody table) in blocking buffer. After overnight incubation, larvae were washed 3×20 min (PBS+0.4% Triton-X-100) then incubated for 2 h with Alexa-Fluor-488 or -555 antibodies (Invitrogen) diluted 1:1000 in blocking buffer, followed again by washing 3×20 min. Larvae were mounted on glass slides using VectaShield Antifade mounting medium (Vector Laboratories). Images of NMJs at segments A2/A3 of larval muscles 12/13 were acquired with a Nikon A1R confocal laser scanning microscope by acquiring Z-stacks through the entire NMJ in 0.2 µm depth intervals with a 1.0 Airy unit pinhole opening. All images of NMJs shown are maximum projections of Z-stacks.

To quantify the association between Tau and CSP-labeled synaptic vesicles in vivo at *Drosophila* NMJs, the "Colocalisation Test" plug-in in ImageJ software was used. Each bouton at an NMJ was individually encircled as an ROI, and the Z-position was selected where CSP was the widest/most peripheral around the bouton. The "Colocalisation Test" plug-in (Image J) was then run to measure the overlap between the Tau (DAKO antibody) and CSP channels using 75 iterations, Fay randomization, and measuring only on the individual Z-section. The R(obs) value was taken as the Pearson's coefficient for that bouton. The same analysis was performed for every bouton at a NMJ and averaged to give n=1 data point. Note that the large area of the bouton occupied by CSP-labeled synaptic vesicles gives rise to a high background Pearson coefficient, and therefore Tau ΔN (lacking the N-terminal synaptic vesicle binding domain) serves as a control for loss of synaptic vesicle binding in experiments depicting quantification of Pearson coefficients.

1.9. FRAP Assay of Synaptic Vesicle Mobility at *Drosophila* Larval NMJs

The use of a fluorescence recovery after photobleaching (FRAP) assay to assess synaptic vesicle mobility has been described previously (Seabrooke et al., 2010; Zhou et al., 2017). Flies expressing UAS-Synaptotagmin-GFP and UAS-Tau under control of the D42-Gal4 promoter were crossed with WT (w1118 strain) or Syngr KO flies to give a Syngr –/+ background. Third-instar larvae were dissected in fresh HL3 buffer and pinned down to Sylgard-coated plates. Synaptotagmin-GFP fluorescence was visualized on a Nikon A1R confocal laser microscope with a 60×1.0 N.A. water immersion objection immersed in HL3 buffer. Images were acquired at 1.12 µs/px, pinhole 1 airy unit, resolution 512× 512 px using the 488 nm laser line and appropriate filters for GFP fluorescence. All recordings were made from boutons at segments A2/A3 of muscles 12/13. Following acquisition of a pre-bleach baseline, a small spot (24×30 px) on the periphery of the bouton was photobleached using 95% laser power of both 405 nm and 488 nm laser lines (9 iterations). Imaging at normal acquisition settings was continued at 1 s intervals for 60 s. The intensity of the bleached spot, plotted as percent of initial fluorescence, was normalized to a non-bleached reference bouton and measured using Nikon analysis software (NIS-Elements AR 4.5), and the trace was fit to a double exponential curve in GraphPad Prism 7 software. FRAP traces from 2-4 boutons were acquired per larvae.

1.10. Electrophysiology at *Drosophila* Larval NMJs.

For electrophysiology, flies expressing D42>UAS-$Tau^{P301L}$ (recombined on chromosome III) were crossed to WT or syngr KO flies to give a $syngr^{+/-}$ background. Axons innervating NMJs at segments A2/A3 of larval muscles at 12/13 were cut and used for intracellular voltage recordings using sharp electrodes (~20 MΩ resistance, 2× stimulation threshold). NMJ excitatory junction potentials (EJPs) were recorded in response to 10 Hz stimulation with an Axoclamp 900A amplifier and digitized with a Digi-data 1440A device, and recorded in pClamp software (version 10.2, Molecular Devices). Maximum EJP amplitudes were binned every 30 s and normalized to the amplitude measured in response to the first 15 stimuli.

1.11. Primary Hippocampal Neuronal Culture from Tau Transgenic Mice

The generation and characterization of the Tau PS19 mouse model has been previously described (Yoshiyama et al., 2007). For primary neuronal cultures, hemizygous Tau PS19 males on a C57BL/6 background were mated with wild-type female C57BL/6 mice from an unrelated colony. Embryos were harvested on day E17.5, and brains isolated and dissected in Hank's balanced salt solution (HBSS) to obtain the hippocampi. Hippocampal pieces were incubated with 0.25% Trypsin and 0.1 mg/mL DNase in HBSS for 15 min at 37° C., followed by three washes in HBSS before resuspension in prewarmed MEM containing 10% (v/v) horse serum, 33 mM D-glucose, and 1× Pen-Strep (Invitrogen). Hippocampal pieces were gently triturated with glass Pasteur pipettes of decreasing size to obtain a single-cell suspension. Neurons were plated at a density of ~55,000 cells per 18 mm glass coverslip (nitric acid-washed and coated with 0.1 mg/mL poly-lysine and 1 µg/mL laminin). 2-4 h after plating, the medium was replaced with NB-B27 medium (Neurobasal medium+1× B27 supplement, 0.5 mM Glutamax, 0.2× Pen-Strep, Invitrogen). Neurons were kept in a 37° C. incubator with 5% $CO_2$. $\frac{1}{3}^{rd}$ of the medium was replaced with fresh medium every 7 days.

Neurons from hippocampi of each independent embryo were individually cultured, and genotyped using the primers 5'-GGGGACACGTCTCCACGG-CATCTCAGCAATGTCTCC-3' (forward; SEQ ID NO:11) and 5'-TCCCCCAGCCTAGACCACGAGAAT-3' (reverse; SEQ ID NO:12) which gives a hTau$^{P301S}$ transgene-specific PCR product at 350 bp. An internal control primer pair (forward 5'-CAAATGTTGCTTGTCTGGTG-3', SEQ ID NO:13; reverse 5'-GTCAGTCGAGTGCACAGTTT-3', SEQ ID NO:14), which gives a PCR product at 170 bp, was used as a positive control. DNA from embryonic tails was prepared and processed for genotyping using the KAPA Mouse Genotyping HotStart Kit (KAPA Biosystems) according to manufacturer's instructions. For functional assays, neurons from non-transgenic littermates were used as controls in comparison to neurons hemizygous for the Tau$^{P301S}$ transgene.

1.12. Preparation of Lentiviruses and Transduction of Primary Neurons.

Scramble and syngr3 knock-down vectors: Transfer plasmids encoding RFP (CMV promoter) and scramble or anti-mouse/rat syngr3 shRNAs (U6 promoter) were produced in the pRFP-CB-shLenti plasmid by Origene. The sh Syngr3 A targeting sequence is 5'-GTTCGTAGGCTTCTGTTTCCTCACCAATC-3' (SEQ ID NO:15) and the sh Syngr3 B targeting sequence is 5'-GAGCCTGCCGCTTCGGCGTCGTACTAGGT-3' (SEQ ID NO:16). The scramble sequence is 5'-GCAC-TACCAGAGCTAACTCAGATAGTACT-3' (SEQ ID NO:17). The loop sequence is 5'-TCAAGAG-3' (SEQ ID NO:18).

Synaptophysin-eGFP vector: The cDNA sequence encoding rat Synaptophysin (307 aa) was cloned upstream of a C-terminal eGFP fusion tag (238 aa) in a second-generation lentiviral transfer plasmid under control of the rat 1.1 kb Synapsin-1 promoter fragment.

Transfer plasmids, the psPAX2 packaging plasmid, and the pMD2.G envelope plasmid (Addgene) were propagated in TOP10 cells (Invitrogen) and plasmid DNA was purified for transfection using a Plasmid Plus Midi Kit (Qiagen). $1.3 \times 10^7$ HEK 293T cells (50-70% confluency) in a T175 flask were transfected with 1 µg pMD2.G, 9 µg psPAX2, and 10 µg transfer plasmid with Lipofectamine-2000 (Invitrogen) according to manufacturer's instructions in DMEM+ 2% fetal bovine serum (FBS). 6 h after the start of transfection, the medium was replaced with 15 mL fresh DMEM+10% FBS. Conditioned medium containing lentiviral particles was collected 48 h after the end of transduction, was passed through a 0.2 µm filter and concentrated using a Amicon Centrifugal Filter Unit with a 100 kDa molecular weight cut-off to a final volume of 1 mL, then was aliquoted, snap-frozen and stored at –80° C. until use. The viral titer was empirically tested; in general, 10-20 µL of concentrated lentivirus-containing medium (15 mL from one T175 flask concentrated to 1 mL) was used to transduce ~55,000 neurons on a 18 mm coverslip in a 12-well plate.

Primary hippocampal neurons were transduced on DIV4 or DIV5. Half of the culture medium was removed and moved to a new plate, to which another half of fresh NB-B27 medium was added. 10-20 µL of each lentivirus was added to each coverslip and left for 6 h to infect neurons. After 6 h, the lentivirus-containing medium was completely removed and was replaced with the half-conditioned/half-fresh NB-B27 mix. Medium was not changed again for 7 days following transduction.

1.13. Immunohistochemistry of Neuronal Cultures.

DIV 17 neurons were washed once with PBS (with $MgCl_2$ and $CaCl_2$) and fixed (4% paraformaldehyde+4% sucrose in PBS) for 25 min at room temperature. Neurons were permeabilized and blocked by incubation with 5% goat serum, 2% BSA, 0.3% Triton-X-100 in PBS for 1 h at room temperature. Coverslips were incubated with primary antibody (see table for dilutions) overnight at 4° C. in PBS with 2% goat serum, 2% BSA and 0.1% Triton-X-100. The next day coverslips were washed 3×5 min in PBS, then incubated with secondary Pacific Blue, Alexa-Fluor-488, -555 or -647 antibodies (Invitrogen) diluted 1:500 in PBS with 2% goat serum, 2% BSA and 0.1% Triton-X-100 for 2 h at room temperature. Following 3×5 min washes in PBS, coverslips were mounted onto glass slides with VectaShield Antifade mounting medium (Vector Laboratories). Images were acquired on a Nikon A1R confocal microscope with 1 Airy unit pinhole opening. All images of primary neurons shown are single optical sections (0.2 µm depth).

The quantification of the presynaptic localization of Tau in hippocampal neurons was measured as the Pearson colocalization coefficient between hTau$^{P301S}$ (HT7 antibody) and the synaptic vesicle marker Synapsin. Entire axon segments of approximately 20 µm were selected as ROIs. Distal axon segments (at least 60 µm away from cell body) were randomly chosen using Synapsin and RFP channels in an unbiased way. The "Colocalisation Test" plug-in in ImageJ was then run on acquired images to measure the overlap between the two channels using 75 iterations and Fay randomization. The R(obs) value was taken as the Pearson's coefficient.

Quantification of hTau$^{is}$ levels (HT7 antibody) in axons (using same images as for presynaptic localization) was performed in ImageJ by measuring the fluorescence integrated density along axon segments (approximately 20 µm) selected as ROIs. Quantification of Synaptogyrin-3 levels were performed by measuring Synaptogyrin-3 integrated density at Synapsin-labeled presynaptic puncta. The relative intensity of 5-10 puncta per axon/cell was normalized to the Synapsin signal and then averaged to give n=1 data point per cell. Quantification of synapse size was performed by quantifying the area of Synapsin puncta in ImageJ. Quantification of synapse number was manually counted as a function of axon segment length.

1.14. Field Stimulation and Synaptic Vesicle Mobility Assay in Primary Neurons

The vesicle dispersion assay is based on a protocol previously described (Wang et al., 2014). Coverslips containing DIV17 hippocampal neurons transduced on DIV4-5 with lentivirus expressing Synaptophysin-eGFP and, where indicated, lentivirus encoding scramble or anti-syngr3 shRNAs, were transferred out of their medium and bathed for 5 min in recording buffer (25 mM HEPES pH 7.4, 119 mM NaCl, 2.5 mM KCl, 2 mM $CaCl_2$, 2 mM $MgCl_2$, 30 mM glucose) supplemented with 50 µM D-APV (Abcam) and 10 µM CNQX (Sigma) to halt ongoing network activity. Coverslips were transferred into a RC-49MFSH field stimulation chamber (Warner Instruments) and the coverslip was sealed around the edges with oil. Platinum wire electrodes on either side of the recording chamber were connected to the stimulus isolator unit. Recording buffer was added to cover the electrodes, and a 60×1.0 N.A. water-immersion objective was dipped into the chamber. Live imaging was performed on an upright Nikon A1R confocal microscope, using a pinhole opening of 5 Airy units in 1 s intervals using 0.5-1.0% laser power in the 488 nm laser line with acquisitions in 1 s intervals. Fluorescence was recorded for 30 s to ensure no photobleaching or loss of focus before stimulation began. From 30 s onwards, neurons were stimulated for 180 s by delivering 1 ms pulses at 33.3 ms intervals (30 Hz) using a A310 Accupulser (World Precision Instruments) connected to a A365 Stimulus Isolator (World Precision Instruments) set to 50 mA and unipolar mode. For each recording, the change in Synaptophysin-GFP puncta fluorescence intensity (to was set to 100%) was quantified from 20-40 synapses (all clear puncta in view for each coverslip were selected as individual ROIs using Nikon analysis software) from 2-5 axons in view and averaged to give n=1 averaged trace per coverslip.

1.15. Electrophysiology of Autaptic Hippocampal Neurons.

The establishment of autaptic neuronal cultures has been previously described (Bekkers and C. F. Stevens, 1991; Burgalossi et al., 2012). Glass coverslips were grid-stamped with poly-lysine and laminin, and dried. Primary astrocytes dissociated from cortices of P0 NMRI mouse pups (Charles River) were cultivated to 60-70% confluence in a flask containing DMEM+10% FBS, split, and 25,000 astrocytes were plated per 32 mm glass coverslip in a 6-well plate and allowed to form micro-dot islands in DMEM+10% FBS for 4 days. Medium was then exchanged for modified NB-B27 medium (Neurobasal medium+1× B27 supplement, 0.5 mM Glutamax, 12 mM D-glucose, 25 µm β-mercaptoethanol, 0.2× Pen-Strep, Invitrogen), and 2,500 hippocampal neurons were plated directly onto islands. Where indicated, neurons were transduced with lentivirus on DIV5 for 6 hours, followed by a single one-half volume medium change.

Whole-cell voltage clamp electrophysiology was performed on DIV17-19 neurons. All recordings were performed at room temperature, and only islands with single neurons were used for recording. The intracellular pipette solution contained 136 mM KCl, 18 mM HEPES, 4 mM Na-ATP, 4.6 mM $MgCl_2$, 4 mM $K_2$-ATP, 15 mM Creatine Phosphate, 1 mM EGTA and 50 U/mL Phospocreatine Kinase (300 mOsm, pH 7.30). The extracellular solution used during recordings contained 140 mM NaCl, 2.4 mM KCl, 4 mM $CaCl_2$, 4 mM $MgCl_2$, 10 mM HEPES, 10 mM glucose (300 mOsm, pH 7.30). Neurons were whole-cell voltage clamped at 70 mV using a double EPC-10 amplifier (HEKA Elektronik, Lambrecht/Pfalz, Germany) under control of Patchmaster v2×32 software (HEKA Elektronik). Currents were recorded at 20 Hz and low-pass filtered at 3 kHz when stored. Pipettes were pulled using a Sutter P-1000 and resistance ranged from 3 to 5 MΩ. The series resistance was compensated to 75-85%. Cells with series resistances above 15 MΩ were excluded for analysis. Spontaneous glutamatergic release (mEPSCs) was recorded at 70 mV. Evoked release was induced using brief depolarization of the cell soma (from 70 to 0 mV for 1 ms) to initiate action potential-dependent glutamatergic release (eEPSCs).

1.16. Statistical Analyses.

All statistical analyses were performed with GraphPad Prism 7 software. Where quantifications are shown, the graph representation and error bars are defined in each legend, together with the definition of n and which statistical test was performed. Error bars either depict standard deviation (SD) or standard error of the mean (SEM), as indicated. In all instances, statistical significance was defined as follows: ns—not significant ($p>0.05$), * $p<0.05$,  $p<0.01$, * $p<0.001$. For multiple comparisons using one-way ANOVA, Dunnett's multiple comparisons test was used to compare each condition to a single control group.

2. Results 2.1. Synaptogyrin-3 is a Physical and Genetic Interactor of Tau

The localization of pathological hyperphosphorylated Tau to presynaptic terminals of Alzheimer's disease patient brains was previously described (Tai et al. 2014; 2012; Zhou et al. 2017), and recent work demonstrated that presynaptically-localized Tau binds to fly and rodent synaptic vesicles (SVs) via its N-terminal domain (Zhou et al. 2017). To assess the possible relevance of Tau association with SVs in human disease, post-mortem brain tissue from Alzheimer's disease patients or non-demented controls were biochemically fractionated to isolate SVs (FIGS. 5A-B, Table S1). By examining a cohort of 15 patients, enrichment of hyperphosphorylated Tau species in the SV fractions from Alzheimer's disease patient brain using antibodies recognizing disease-associated phospho-Tau epitopes was detected (FIGS. 5C-E). These data suggest the association of Tau with SVs in Alzheimer's disease, warranting further exploration of this pathway as a potential contributor to Tau-induced synaptic dysfunction in human disease.

First, the binding mechanism of Tau to SVs was determined in order to identify new targets to disrupt this interaction. SVs are comprised of the vesicle membrane, integral transmembrane SV proteins, and peripheral SV-associated proteins (Takamori et al. 2006). It was first assessed whether protein-protein interactions or membrane lipid interactions mediate the association of Tau with SVs. SVs were isolated from mouse brain (FIGS. 6A-B) and limited proteolysis was performed by incubation with trypsin, which degrades all peripheral SV-associated proteins and the cytoplasmic domains of transmembrane SV proteins, but leaves the membrane lipid bilayer intact (FIGS. 1A-B). Untreated or trypsinized SVs were then incubated with recombinant human Tau purified from bacteria (FIG. 6C). Following incubation with Tau, SVs are pelleted by ultracentrifugation and the binding of Tau to SVs is assessed by immunoblotting for Tau in the SV pellet. In this co-sedimentation assay, Tau binds to untreated SVs, but this binding is largely lost upon proteolysis of SV proteins (FIGS. 1C-D), indicating that SV proteins are required for Tau binding to SVs. In agreement therewith, Tau binding to synthetic protein-free liposomes which are similar in size and lipid composition to SVs was not detected (FIG. 6D). Thus, protein-protein interactions underlie the binding of Tau to SVs.

To further delineate whether Tau binds to SVs via interaction with transmembrane SV proteins or peripheral SV-associated proteins, carbonate stripping of SVs was performed. This manipulation removes peripheral SV-associated proteins but leaves transmembrane SV proteins intact (FIG. 1E).

When introduced into the sedimentation assay, Tau binds equally well to untreated and carbonate-stripped SVs (FIGS. 1F-G), indicating that peripheral SV-associated proteins are dispensable for binding. Together, these data indicate that Tau binds to SVs via interaction with transmembrane SV proteins.

An unbiased forward proteomics approach was then utilized to identify the transmembrane SV proteins that bind Tau (FIG. 1H). High-detergent lysis of isolated SVs to solubilize SV proteins was followed by a co-immunoprecipitation (co-IP) reaction using purified recombinant $Tau^{FL}$-His or $Tau^{\Delta N}$-His as bait (FIG. 6C), followed by mass spectrometry analysis to identify bound proteins. The N-terminal domain of Tau is required for binding to SVs (Zhou et al. 2017), and thus the interactor of Tau on SVs should bind full-length Tau ($Tau^{FL}$) but not N-terminally truncated Tau ($Tau^{\Delta N}$). Using this approach, 8 SV proteins were identified as potential interactors of Tau (FIG. 1I, Table S2), but only one protein was both transmembrane and specific to the N-terminus of Tau: Synaptogyrin-3 (Syngr3).

Syngr3 is the only candidate which fits the criteria as a potential interactor of Tau in vitro; nevertheless, it was tested whether Drosophila homologues of any of the 8 SV proteins identified in our proteomics approach show a genetic interaction with Tau in vivo by performing a fly genetic screen. In this screen, flies expressing FTDP-17 clinical mutant $Tau^{P301L}$ were crossed to loss-of-function alleles or shRNA constructs for the Drosophila homologues of these 8 candidate interactors, and colocalization of Tau with SVs was measured as a readout of Tau-SV association in vivo (FIG. 1.1, see also below). In third-instar Drosophila larvae expressing human Tau carrying FTDP-17 clinical mutations (P301L, V337M, or R406W) in motor neurons, mutant Tau dissociates from axonal microtubules and relocalizes to presynaptic neuromuscular junction (NMJ) boutons. At boutons, Tau colocalizes with SVs that organize in a ring-like pattern in the periphery of the bouton (FIGS. 2A-B), which is quantifiable using the Pearson co-localization coefficient between Tau and SVs immunolabeled with anti-Cysteine String Protein (CSP) antibodies. $Tau^{P301L}$ showed a diffuse pattern when the expression level of Synaptogyrin was lowered (Syngr, the single Drosophila homologue of Syngr3 (Stevens et al. 2012)), but not any other candidate interactor (FIGS. 1K, 2A-B). Similarly, two other pathogenic FTDP-17 Tau mutants also show diffuse localization at boutons when Syngr expression is lowered (FIG. 2C). Both heterozygous loss (50% reduction) and shRNA-mediated knock-down (90% reduction, FIGS. 6E-F) of Syngr were effective to cause dissociation of Tau from SVs to a similar extent as genetically deleting the N-terminal SV binding domain of Tau (expression of $Tau^{\Delta N}$) (FIGS. 1K, 2A-C), indicating that partial loss of Syngr is sufficient to reduce Tau-SV binding in vivo.

To test if Syngr is required for the direct physical interaction of Tau with SVs, SVs were isolated from wild-type (WT) or syngr null knock-out (KO) adult fly brains (FIGS. 6G-H). In the co-sedimentation assay, recombinant human Tau binds to WT SVs, but binding to syngr KO SVs is severely reduced (FIGS. 2D-E). These results complement the findings at NMJs in vivo where reduction of Syngr caused the diffuse localization of pathogenic Tau (FIGS. 2A-C). Taken together, these data indicate that the physical interaction between Tau and Syngr is the principle mechanism underlying the binding of Tau to SVs.

2.2. Reduction of Synaptogyrin Rescues Tau-Induced Presynaptic Dysfunction in Drosophila When Tau binds to SVs they become cross-linked and less mobile, causing defects in the recruitment of a sufficient number of vesicles to maintain neurotransmitter release during sustained activity (Zhou et al. 2017). It was shown here that Syngr mediates the association of Tau with SVs and it was therefore assessed whether reduction of Syngr is sufficient to rescue Tau-induced presynaptic defects. As a readout of SV crosslinking, the mobility of SVs at larval NMJs was examined using fluorescence recovery after photobleaching (FRAP). In larvae expressing the live SV marker Synaptotagmin-GFP (Syt-GFP), photobleaching of a small area of SVs within a presynaptic bouton depletes those vesicles of Syt-GFP fluorescence, and the recovery of fluorescence signal over time in that area therefore reflects the mobility of other SVs which diffuse in (Seabrooke et al. 2010). In comparison to controls, SV mobility at presynaptic boutons in larvae expressing three independent pathogenic Tau mutants is reduced, indicative of Tau-induced SV crosslinking (FIGS. 3A-B). Notably, heterozygous loss of Syngr is sufficient to restore SV mobility back to control levels in all three mutant Tau backgrounds (FIGS. 3A-B). This increased vesicle mobility was specific to Tau, as $syngr^{+/-}$ larvae alone did not differ in SV mobility in comparison to controls (FIG. 3B). Thus, Syngr-dependent binding of Tau to SVs directly impairs SV mobility at presynaptic terminals.

To test if reduction of Syngr is also sufficient to ameliorate Tau-induced defects in neurotransmission during sustained activity, excitatory junction potentials (EJPs) at larval NMJs in response to 10 Hz stimulation for 10 minutes were recorded. Larvae expressing $Tau^{P301L}$ exhibit progressively lower EJP amplitudes during this stimulation paradigm; however, this defect is rescued back to control levels upon reduction of Syngr ($syngr^{+/-}$) (FIGS. 3C-E). Taken together, these data support the hypothesis that presynaptically-localized pathogenic Tau directly binds and crosslinks SVs via Syngr, preventing vesicle recruitment into release and ultimately attenuating neurotransmitter release during sustained activity.

2.3. Synaptogyrin-3 Mediates Presynaptic Dysfunction in Hippocampal Neurons from a Tauopathy Mouse Model The mammalian genome encodes four Synaptogyrins which are distantly related to Synaptophysin and Synaptoporin, and share a common topology of four transmembrane domains with cytoplasmic exposed N- and C-terminal tails (Kedra et al. 1998). Only Synaptogyrins-1 and -3 are neuron-specific and present on synaptic vesicles (Belizaire et al. 2004). The proteomics screen described above only identified Syngr3 as a Tau interactor and it was therefore tested whether reduction of Syngr3 is sufficient to ameliorate synaptic dysfunction in neurons of a well-established transgenic mouse model of Tauopathy. Tau PS19 mice express human FTDP-17 clinical mutant $Tau^{P301S}$ and show disease-relevant features of synaptic dysfunction, synapse loss and neurodegeneration during ageing (Yoshiyama et al. 2007). First, it was assessed if FTDP-17 mutant $Tau^{P301S}$ localizes to presynaptic terminals in mouse hippocampal neurons. A primary neuronal culture was established from the hippocampi of E18 Tau PS19 transgenic mouse embryos, allowed them to mature for 17 days in culture, and then assessed Tau$^{P301S}$ localization by immunohistochemistry together with the presynaptic markers VGlut1 or Synapsin and the dendritic marker MAP2. At distal axons, a punctate staining of Tau$^{P301S}$ along the axon that colocalizes with the presynaptic marker VGlut1 was observed (FIGS. 7A-C). Thus, consistent with the fly model, pathogenic mutant Tau localizes to presynaptic terminals in hippocampal neurons from Tau PS19 mice, recapturing this key pathogenic event also observed in sporadic disease conditions such as in Alzheimer's disease.

It was subsequently assessed whether lowering the expression level of Syngr3 alters this punctate presynaptic localization of Tau. Lentiviruses encoding RFP as well as short hairpin sequences targeting Syngr3 were produced, and two independent shRNA constructs that result in more than 95% reduction of Syngr3 levels but did not obviously affect neuronal viability, morphology or synapse formation were validated (FIGS. 7D-G). In neurons transduced with scrambled control virus, Tau$^{P301S}$ maintained its punctate localization along the axon, showing tight localization to Synapsin-labeled presynaptic vesicle clusters in the axon, negative for the dendritic marker MAP2 (FIG. 4A). In contrast, virus-mediated shRNA knock-down of Syngr3 resulted in a more diffuse staining pattern of Tau$^{P301S}$ along the axon, and Tau$^{P301S}$ no longer tightly associated with SV clusters (FIG. 4A). As a measure of Tau association with presynaptic vesicle clusters, Tau$^{P301S}$ colocalization with the SV marker Synapsin along axons was quantified, which revealed a significant reduction in Tau$^{P301S}$ association to presynaptic SV clusters upon Syngr3 knockdown (FIG. 4B), whereas overall Tau levels are unaffected (FIG. 4C). Thus, Syngr3 recruits Tau$^{P301S}$ to sites of presynaptic vesicle clusters in mouse hippocampal neurons, suggesting Syngr3-dependent association of Tau with SVs.

It was further determined whether Syngr3-dependent association of Tau with SVs leads to reduced SV mobility in hippocampal neurons using a SV dispersion assay. At mammalian central synapses, SVs sit in tight clusters along the axon, which become more mobile and diffuse during neuronal activity (Sankaranarayanan & Ryan 2000). Measuring the change in fluorescence intensity of a live SV marker to assess vesicle diffusion during neuronal stimulation can therefore serve as a measure of vesicle mobility (Wang et al. 2014). Hippocampal neurons were transduced with lentivirus expressing the live SV marker Synaptophysin-GFP (Syph-GFP). Live imaging was used to record changes in Syph-GFP fluorescence intensity, which decreased in response to 30 Hz stimulation, reflecting activity-dependent vesicle mobilization (FIG. 4D). In comparison to neurons from non-transgenic (Non Tg) littermates, neurons from Tau$^{P301S}$ transgenic mice showed reduced change in Syph-GFP fluorescence during 30 Hz stimulation (FIGS. 4D-E), indicative of impaired SV mobility. Upon reducing Syngr3 levels in Tau$^{P301S}$ neurons by transduction with Syngr3 knock-down virus, SV mobility was restored back to control levels (FIGS. 4D and 4F). Thus, Syngr3-dependent binding of Tau to SVs underlies Tau-induced defects in presynaptic vesicle mobility.

Finally, it was determined if Tau-induced, Syngr3-mediated defects in SV mobility were functionally related to defects in neurotransmission by performing electrophysiology on autaptic cultures of hippocampal neurons. Whole-cell voltage clamp recordings of DIV17-19 neurons did not show obvious differences in basal release parameters in neurons from Tau$^{P301S}$ mice as compared to Non Tg littermates. However, measuring release in response to repeated 10 Hz stimulation trains revealed that Tau$^{P301S}$ neurons could not sustain evoked release efficacy as well as Non Tg neurons (FIGS. 4G-H). In contrast, reducing Syngr3 levels in Tau$^{P301S}$ neurons by transduction with Syngr3 knock-down virus restored evoked neurotransmitter release to a similar range as Non Tg controls (FIGS. 4G, 4I). These data strongly support the model of Tau crosslinking SVs via Syngr3 and rendering a portion of the SV pool unable to be recruited into release, ultimately lowering neurotransmitter release during sustained stimulation.

Taken together, these data identify Syngr3 as a novel interactor of Tau which mediates synaptic release deficits in fly and mouse models of Tauopathy by acting as the receptor of Tau on presynaptic SVs. By targeting Syngr3, an exclusively presynaptic SV protein, the presynaptic function of Tau was genetically uncoupled from other potential pathological functions and revealed that specific inhibition of Syngr3-dependent Tau-SV binding ameliorates defects in presynaptic function and neurotransmitter release.

2.4. Tau Protein and Synaptogyrin-3 Directly Interact

To check whether Tau and Syngr-3 directly interact a split luciferase assay was used, more precisely we made use of the NanoLuc Binary Technology (NanoBir). Briefly, in this split reporter assay, target proteins that interact with each other are fused to one of two luciferase subunits. Said subunits interact only weakly with each other, hence luciferase assembly is driven by the affinity/interaction of the target proteins onto which the luciferase subunits are appended. Upon structural complementation, an active and bright luciferase is formed (FIG. 8). Such approach allows accurate quantification of Tau-Syngr3 interaction under physiological conditions relevant to the cellular environment.

We have engineered several constructs comprising Tau or Syngr3 (as well as p53 as control) fused to either the large subunit (LgBit) or the small subunit (SmBit) of luciferase. The constructs were expressed in HEK-293T cells and using a standard multimode plate reader the luminescence was determined. A strong luminescence signal was detected for the Tau-Syngr3 interaction in contrast to the controls (FIG. 9). These data are in line with the above and illustrate a direct interaction between Tau and Syngr3.

2.5 Screening for Inhibitors of the Tau-Syngr3 Interaction

Besides genetic inhibition of synaptogyrin-3 using for example shRNAs, gapmers or Crispr-Cas effectors, current document also discloses a screen to find small molecules that block the binding or interaction between synaptogyrin-3 and the Tau protein.

The above split luciferase approach is performed in 384 wells to be compatible with a large-scale compound screening. Compounds are selected based on their ability to decrease the luminescence signal and thus the level of Tau-Syngr3 interaction. The identified compounds are further selected on their selectivity by testing the possibility of targeting related proteins, such as Syngr1.

3. Discussion

Synaptic dysfunction is thought to be an early and important pathogenic step in Alzheimer's disease and other neurodegenerative diseases associated with Tau. While numerous lines of evidence position Tau itself as a major executor of synaptic dysfunction, the precise mechanisms underlying Tau-induced synaptic pathology have remained elusive. Tau can act postsynaptically, where it affects glutamate receptor organization (Hoover et al. 2010; Ittner et al. 2010), as well as presynaptically, where it clusters SVs via F-actin networks (Zhou et al. 2017). Here, it was defined that Tau binding to the transmembrane SV protein Syngr3 mediates Tau-induced defects in presynaptic SV mobility, preventing SV recruitment into release and lowering neurotransmission. Given that Syngr3 is exclusively present on presynaptic vesicles, these findings present Syngr3 as a novel Tau interactor involved in Tau pathogenesis at the presynapse. This work opens new avenues for specifically targeting the presynaptic function of Tau both to selectively evaluate the contribution of this pathway to disease progression in animal models, as well as for future therapeutic approaches targeting synaptic dysfunction in Alzheimer's disease and related Tauopathies.

The mechanism of Tau-SV binding was validated as disease-relevant by finding that pathological Tau species associate with SVs isolated from Alzheimer's disease patient brains. In vitro assays of recombinant human Tau binding to isolated mouse SVs were used to mechanistically define that Tau binds to SVs via protein-protein interactions with transmembrane SV proteins. Using a forward proteomics approach, eight candidate SV interactors were identified, but only Syngr3 was both transmembrane and specific to the N-terminal SV binding domain of Tau. In agreement therewith, when testing the genetic interaction of all eight candidates with Tau in flies, only the Syngr3 homologue reduced Tau association with SVs in vivo. The identification of other candidate interactors may have been due to secondary interactions with other domains of Tau and could have small contributions to SV binding. Nonetheless, this work found the interaction between the N-terminus of Tau and Syngr3 to be the predominant mechanism by which Tau associates with SVs, and the reduction of Syngr3 alone was sufficient to reduce the associated presynaptic deficits in neurons.

The mammalian genome encodes four Synaptogyrins, but only Syngr1 and Syngr3 are neuron-specific and present on SVs (Belizaire et al. 2004; Kedra et al. 1998). While a redundant role of Syngr1 and Synaptophysin in synaptic plasticity has been described (Janz et al. 1999), there is no known physiological function of Syngr3. Nevertheless, our preliminary studies indicate the potential safety of targeting Syngr3: >95% knock-down of Synaptogyrin-3 in mouse neurons did not obviously affect neuron or synapse development, and rescued Tau-induced presynaptic defects without inducing additional toxicity in the parameters we measured. Furthermore, *Drosophila* syngr null KO flies are viable, healthy, and do not show overt defects in presynaptic function (Stevens et al. 2012). Importantly, in our fly model a 50% reduction (heterozygous loss) was already sufficient to rescue functional defects, suggesting only mild reduction of Syngr3 may be effective to bring levels of Tau-SV binding below a pathogenic threshold, likely because many non-essential SV proteins are present in low copy number, i.e. 1-2 per SV (Takamori et al. 2006). Hence, inhibiting the Syngr3-Tau interaction may be a relatively safe therapeutic avenue to pursue.

Finally, several observations make Syngr3 interesting as a potentially disease-relevant Tau interactor. First, while expressed throughout the brain, Syngr3 expression is enriched in the hippocampus (Belizaire et al. 2004), a region particularly vulnerable to neuronal dysfunction in Alzheimer's disease and Tauopathy mouse models (Braak & Braak 1991; Yoshiyama et al. 2007). Second, Syngr3 levels are 4-fold higher on glutamatergic SVs compared to GABAergic SVs (Bragina et al. 2010), consistent with a recent report showing that early Tau pathology preferentially affects excitatory neurons (Fu et al. 2017). Third, Syngr3 is also present on exosomes (Gallart-Palau et al. 2016), which has been proposed as a mechanism of cell-to-cell transfer of pathological Tau species which is also synapse- and activity-dependent (Calafate et al. 2015; Thompson et al. 2016; Wu et al, 2016). While these connections are only speculative, they nonetheless poise Syngr3 as an interesting and potentially relevant interactor of Tau warranting further investigation. Importantly, perturbations in synaptic function associated with Tau are thought to drive disease progression but the contribution of the presynaptic role of Tau has never been tested experimentally due to lack of a specific approach. Therefore, the identification of Syngr3, an exclusively presynaptic SV protein, provides a new way to assess the contribution of the presynaptic role of Tau to overall synaptic dysfunction, independent of other pathways such as Tau aggregation or Tau localization to post-synapses.

In sum, we uncovered the interaction of Tau with the SV protein Syngr3 as the principle mechanism of Tau binding to presynaptic vesicles, a key step which leads to excessive Tau-induced SV clustering, resulting in restricted SV mobility and ultimately attenuating neurotransmission. Syngr3 is therefore a new culprit in Tau pathogenesis, opening a new avenue for specific targeting of Tau synaptotoxicity in early stages of synaptic and cognitive dysfunction in Alzheimer's disease and related Tauopathies.

TABLE S1

Patient data for human brain samples related to FIG. 5. All samples were collected from the postmortem hippocampus of non-demented (ND) control patients or patients diagnosed with Alzheimer's disease (AD) and biochemically fractionated according to the scheme depicted in FIG. 5A.

| Internal Reference | Age | Gender | Diagnosis | Stage | MRC Database No. (BBN) |
|---|---|---|---|---|---|
| Control Group | | | | | |
| BD 2010-062 | 94 | Female | ND | — | N/A |
| BD 2010-038 | 79 | Female | ND | — | N/A |
| Ed2 SD055/12 | 76 | Male | ND | — | 9508 |
| Ed2 SD014/13 | 74 | Female | ND | — | 14395 |
| Ed2 SD048/12 | 63 | Male | ND | — | 7626 |
| Ed2 SD032/13 | 61 | Male | ND | — | 16425 |
| Ed1 SD029/13 | 58 | Male | ND | — | 15809 |
| Ed1 SD011/15 | 57 | Male | ND | — | 24781 |
| Ed1 SD010/15 | 57 | Female | ND | — | 24780 |
| Ed1 SD017/13 | 45 | Female | ND | — | 14397 |
| Ed1 SD022/13 | 45 | Male | ND | — | 15222 |
| Ed1 SD022/16 | 39 | Male | ND | — | 28959 |
| Ed1 SD026/16 | 37 | Female | ND | — | 28960 |

TABLE S1-continued

Patient data for human brain samples related to FIG. 5. All samples were collected from the postmortem hippocampus of non-demented (ND) control patients or patients diagnosed with Alzheimer's disease (AD) and biochemically fractionated according to the scheme depicted in FIG. 5A.

| Internal Reference | Age | Gender | Diagnosis | Stage | MRC Database No. (BBN) |
|---|---|---|---|---|---|
| AD Group | | | | | |
| Ed1 SD013/13 | 86 | Male | AD | 4 | 15812 |
| Ed2 SD033/14 | 85 | Female | AD | 3 | 22627 |
| Ed2 SD045/13 | 85 | Female | AD | 3 | 19600 |
| Ed2 SD035/13 | 85 | Female | AD | 4 | 18798 |
| Ed1 SD033/14 | 85 | Female | AD | 3 | 22627 |
| Ed1 SD045/13 | 85 | Female | AD | 3 | 19600 |
| Ed1 SD035/13 | 85 | Female | AD | 4 | 18798 |
| Ed1 SD046/14 | 83 | Female | AD | 3 | 24306 |
| BD 2007-009 | 82 | Female | AD | 4 | N/A |
| Ed2 SD019/13 | 82 | Female | AD | 4 | 15814 |
| Ed1 SD019/13 | 82 | Female | AD | 4 | 15814 |
| BD 2010-011 | 80 | Male | AD | 4 | N/A |
| Ed2 SD023/15 | 77 | Male | AD | 3 | 26491 |
| Ed1 SD017/14 | 75 | Male | AD | 3 | 20994 |
| Ed2 SD050/14 | 67 | Male | AD | 4 | 24323 |

TABLE S2

Complete mass spectrometry dataset from co-IP of $Tau^{FL}$ and $Tau^{\Delta N}$ with synaptic vesicle lysate. Related to FIG. 1.
Proteins identified were cross-referenced against previous data sets defining the synaptic vesicle proteome, and proteins were classified as transmembrane SV proteins, SV-associated proteins, or others (contaminates). Spectral counts are given from three technical replicates.

| Accession | Description | Gene Name | Spectral Counts IgG only | | | Spectral Counts $Tau^{FL}$ | | | Spectral Counts $Tau^{\Delta N}$ | | |
|---|---|---|---|---|---|---|---|---|---|---|---|
| | Transmembrane synaptic vesicle proteins | | | | | | | | | | |
| Q8R191 | Synaptogyrin-3 | Syngr3 | 0 | 0 | 0 | 0 | 1 | 1 | 0 | 0 | 0 |
| P46096 | Synaptotagmin-1 | Syt1 | 0 | 0 | 0 | 1 | 0 | 0 | 0 | 1 | 3 |
| | Peripheral synaptic vesicle-associated proteins | | | | | | | | | | |
| Q8CHC4 | Synaptojanin-1 | Synj1 | 0 | 0 | 0 | 0 | 1 | 0 | 0 | 2 | 1 |
| P47708 | Rabphilin-3A | Rph3a | 0 | 0 | 0 | 2 | 0 | 0 | 0 | 0 | 0 |
| P39053 | Dynamin-1 | Dnm1 | 5 | 5 | 5 | 50 | 46 | 54 | 67 | 65 | 58 |
| P39054 | Dynamin-2 | Dnm2 | 0 | 0 | 1 | 5 | 5 | 7 | 5 | 5 | 0 |
| Q8BZ98 | Dynamin-3 | Dnm3 | 0 | 0 | 0 | 10 | 14 | 9 | 13 | 9 | 15 |
| O55131 | Septin-7 | Sept7 | 0 | 0 | 0 | 19 | 15 | 18 | 22 | 23 | 21 |
| O88935 | Synapsin-1 | Syn1 | 47 | 51 | 50 | 26 | 20 | 22 | 12 | 15 | 12 |
| Q64332 | Synapsin-2 | Syn2 | 1 | 1 | 0 | 1 | 0 | 2 | 0 | 1 | 2 |
| Q9QYX7 | Protein piccolo | Pclo | 1 | 0 | 0 | 0 | 0 | 0 | 0 | 0 | 0 |
| | Other non-synaptic vesicle proteins (absent in negative control) | | | | | | | | | | |
| Q9Z2Q6 | Septin-5 | Sept5 | 0 | 0 | 0 | 8 | 9 | 10 | 6 | 9 | 7 |
| Q8QZT1 | Acetyl-CoA acetyltransferase, mitochondrial | Acat1 | 0 | 0 | 0 | 8 | 9 | 7 | 9 | 10 | 10 |
| Q8BYI9 | Tenascin-R | Tnr | 0 | 0 | 0 | 7 | 9 | 4 | 1 | 0 | 1 |
| Q8C1B7 | Septin-11 | Sept11 | 0 | 0 | 0 | 7 | 8 | 4 | 7 | 8 | 8 |
| Q9R1T4 | Septin-6 | Sept6 | 0 | 0 | 0 | 7 | 5 | 6 | 7 | 7 | 6 |
| Q9Z1S5 | Neuronal-specific septin-3 | Sept3 | 0 | 0 | 0 | 6 | 7 | 5 | 7 | 6 | 4 |
| Q5SQX6 | Cytoplasmic FMR1-interacting protein 2 | Cyfip2 | 0 | 0 | 0 | 3 | 1 | 2 | 2 | 1 | 2 |
| Q8OUG5 | Septin-9 | Sept9 | 0 | 0 | 0 | 2 | 3 | 4 | 4 | 5 | 4 |
| Q8CBW3 | Abl interactor 1 | Abi1 | 0 | 0 | 0 | 2 | 3 | 2 | 7 | 4 | 5 |
| Q8R5H6 | Wiskott-Aldrich syndrome protein family member 1 | Wasf1 | 0 | 0 | 0 | 2 | 1 | 3 | 4 | 1 | 1 |
| Q8CHH9 | Septin-8 | Sept8 | 0 | 0 | 0 | 2 | 1 | 2 | 2 | 1 | 1 |
| | 40S ribosomal protein | | | | | | | | | | |

TABLE S2-continued

Complete mass spectrometry dataset from co-IP of Tau$^{FL}$ and Tau$^{\Delta N}$ with synaptic vesicle lysate. Related to FIG. 1.
Proteins identified were cross-referenced against previous data sets defining the synaptic vesicle proteome, and proteins were classified as transmembrane SV proteins, SV-associated proteins, or others (contaminates). Spectral counts are given from three technical replicates.

| Accession | Description | Gene Name | Spectral Counts IgG only | | | Spectral Counts Tau$^{FL}$ | | | Spectral Counts Tau$^{\Delta N}$ | | |
|---|---|---|---|---|---|---|---|---|---|---|---|
| P62281 | S11 | Rps11 | 0 | 0 | 0 | 1 | 2 | 1 | 0 | 0 | 0 |
| P62484 | Abl interactor 2 | Abi2 | 0 | 0 | 0 | 1 | 2 | 0 | 2 | 0 | 3 |
| P47754 | F-actin-capping protein subunit alpha-2 | Capza2 | 0 | 0 | 0 | 1 | 1 | 1 | 3 | 1 | 2 |
| P28660 | Nck-associated protein 1 | Nckap1 | 0 | 0 | 0 | 1 | 1 | 1 | 2 | 2 | 2 |
| Q8R550 | SH3 domain-containing kinase-binding protein 1 | Sh3kbp1 | 0 | 0 | 0 | 1 | 1 | 1 | 1 | 1 | 1 |
| P62631 | Elongation factor 1-alpha 2 | Eef1a2 | 0 | 0 | 0 | 1 | 1 | 1 | 0 | 1 | 1 |
| P42208 | Septin-2 | Sept2 | 0 | 0 | 0 | 1 | 1 | 0 | 1 | 1 | 1 |
| P99024 | Tubulin beta-5 chain | Tubb5 | 0 | 0 | 0 | 1 | 1 | 0 | 1 | 1 | 0 |
| Q60737 | Casein kinase II subunit alpha | Csnk2a1 | 0 | 0 | 0 | 1 | 1 | 0 | 0 | 1 | 1 |
| P68372 | Tubulin beta-4B chain | Tubb4b | 0 | 0 | 0 | 1 | 0 | 0 | 1 | 0 | 0 |
| P42669 | Transcriptional activator protein Pur-alpha | Pura | 0 | 0 | 0 | 1 | 0 | 0 | 0 | 0 | 0 |
| P80314 | T-complex protein 1 subunit beta | Cct2 | 0 | 0 | 0 | 0 | 2 | 0 | 0 | 0 | 0 |
| P59644 | Phosphatidylinositol 4,5-bisphosphate 5-phosphatase A | Inpp5j | 0 | 0 | 0 | 0 | 1 | 1 | 0 | 0 | 0 |
| P14873 | Microtubule-associated protein 1B | Map1b | 0 | 0 | 0 | 0 | 1 | 0 | 0 | 0 | 0 |
| P62267 | 40S ribosomal protein S23 | Rps23 | 0 | 0 | 0 | 0 | 1 | 0 | 0 | 0 | 0 |
| P62301 | 40S ribosomal protein S13 | Rps13 | 0 | 0 | 0 | 0 | 1 | 0 | 0 | 0 | 0 |
| Q6H1V1 | Bestrophin-3 | Best3 | 0 | 0 | 0 | 0 | 1 | 0 | 0 | 0 | 0 |
| P28661 | Septin-4 | Sept4 | 0 | 0 | 0 | 0 | 0 | 1 | 1 | 0 | 1 |
| P59999 | Actin-related protein 2/3 complex subunit 4 | Arpc4 | 0 | 0 | 0 | 0 | 0 | 1 | 0 | 0 | 0 |
| Q3UJD6 | Ubiquitin carboxyl-terminal hydrolase 19 | Usp19 | 0 | 0 | 0 | 0 | 0 | 1 | 0 | 0 | 0 |
| Q62086 | Serum paraoxonase/arylesterase 2 | Pon2 | 0 | 0 | 0 | 0 | 0 | 1 | 0 | 0 | 0 |
| Q812A2 | SLIT-ROBO Rho GTPase-activating protein 3 | Srgap3 | 0 | 0 | 0 | 0 | 0 | 0 | 1 | 0 | 0 |
| P62082 | 40S ribosomal protein S7 | Rps7 | 0 | 0 | 0 | 0 | 0 | 0 | 0 | 1 | 0 |
| P63085 | Mitogen-activated protein kinase 1 | Mapk1 | 0 | 0 | 0 | 0 | 0 | 0 | 0 | 0 | 1 |
| Q91VR8 | Protein BRICK1 | Brk1 | 0 | 0 | 0 | 0 | 0 | 0 | 0 | 0 | 1 |
| | Other non-synaptic vesicle proteins (present in negative control) | | | | | | | | | | |
| P20357 | Microtubule-associated protein 2 | Map2 | 23 | 15 | 21 | 19 | 16 | 12 | 11 | 9 | 6 |
| P04370 | Myelin basic protein | Mbp | 14 | 13 | 13 | 13 | 13 | 11 | 10 | 12 | 10 |
| P27546 | Microtubule-associated protein 4 | Map4 | 11 | 12 | 10 | 5 | 4 | 6 | 4 | 2 | 2 |
| P16858 | Glyceraldehyde-3-phosphate dehydrogenase | Gapdh | 9 | 9 | 5 | 13 | 8 | 10 | 9 | 8 | 11 |
| Q6PEV3 | WAS/WASL-interacting protein family member 2 | Wipf2 | 8 | 9 | 7 | 1 | 1 | 0 | 0 | 0 | 0 |
| E9Q6B2 | Coiled-coil domain-containing protein 85C | Ccdc85c | 6 | 4 | 5 | 0 | 0 | 0 | 0 | 0 | 0 |
| Q61191 | Host cell factor 1 | Hcfc1 | 6 | 3 | 5 | 0 | 0 | 0 | 0 | 0 | 0 |
| P02535 | Keratin, type I cytoskeletal 10 | Krt10 | 5 | 4 | 5 | 1 | 1 | 2 | 2 | 3 | 2 |
| Q7TQD2 | Tubulin polymerization-promoting protein | Tppp | 4 | 4 | 5 | 3 | 4 | 3 | 2 | 1 | 4 |
| P14131 | 40S ribosomal protein S16 | Rps16 | 4 | 3 | 3 | 2 | 1 | 1 | 1 | 1 | 1 |
| P62862 | 40S ribosomal protein S30 | Fau | 3 | 2 | 3 | 1 | 1 | 2 | 1 | 3 | 2 |
| P10126 | Elongation factor 1-alpha 1 | Eef1a1 | 2 | 3 | 3 | 3 | 3 | 2 | 3 | 2 | 2 |
| Q7TSJ2 | Microtubule-associated protein 6 | Map6 | 2 | 3 | 3 | 1 | 0 | 0 | 1 | 0 | 1 |

TABLE S2-continued

Complete mass spectrometry dataset from co-IP of Tau$^{FL}$ and Tau$^{\Delta N}$ with synaptic vesicle lysate. Related to FIG. 1.
Proteins identified were cross-referenced against previous data sets defining the synaptic vesicle proteome, and proteins were classified as transmembrane SV proteins, SV-associated proteins, or others (contaminates). Spectral counts are given from three technical replicates.

| Accession | Description | Gene Name | Spectral Counts IgG only | | | Spectral Counts Tau$^{FL}$ | | | Spectral Counts Tau$^{\Delta N}$ | | |
|---|---|---|---|---|---|---|---|---|---|---|---|
| Q3TTY5 | Keratin, type II cytoskeletal 2 epidermal | Krt2 | 2 | 2 | 2 | 0 | 0 | 1 | 0 | 0 | 0 |
| Q8CC35 | Synaptopodin | Synpo | 2 | 2 | 1 | 0 | 0 | 0 | 0 | 0 | 0 |
| P04104 | Keratin, type II cytoskeletal 1 | Krt1 | 2 | 1 | 2 | 0 | 0 | 0 | 1 | 1 | 1 |
| P62274 | 40S ribosomal protein S29 | Rps29 | 2 | 1 | 1 | 1 | 1 | 1 | 0 | 1 | 1 |
| P62259 | 14-3-3 protein epsilon | Ywhae | 2 | 0 | 1 | 0 | 0 | 1 | 0 | 0 | 0 |
| P08730 | Keratin, type I cytoskeletal 13 | Krt13 | 1 | 2 | 2 | 0 | 0 | 0 | 0 | 0 | 0 |
| P07724 | Serum albumin | Alb | 1 | 2 | 1 | 1 | 1 | 0 | 1 | 1 | 1 |
| P62270 | 40S ribosomal protein S18 | Rps18 | 1 | 1 | 3 | 4 | 7 | 4 | 1 | 3 | 2 |
| P15105 | Glutamine synthetase | Glul | 1 | 1 | 1 | 2 | 2 | 1 | 1 | 1 | 1 |
| P50446 | Keratin, type II cytoskeletal 6A | Krt6a | 1 | 1 | 1 | 1 | 1 | 1 | 1 | 1 | 1 |
| P02088 | Hemoglobin subunit beta-1 | Hbb-b1 | 1 | 1 | 1 | 1 | 0 | 1 | 1 | 1 | 1 |
| P28665 | Murinoglobulin-1 | Mug1 | 1 | 1 | 1 | 0 | 0 | 0 | 1 | 1 | 0 |
| Q3UV17 | Keratin, type II cytoskeletal 2 oral | Krt76 | 1 | 1 | 1 | 0 | 0 | 0 | 1 | 1 | 0 |
| P01868 | Ig gamma-1 chain C region secreted form | Ighg1 | 1 | 1 | 1 | 0 | 0 | 0 | 0 | 0 | 0 |
| P97315 | Cysteine and glycine-rich protein 1 | Csrp1 | 1 | 1 | 0 | 1 | 1 | 1 | 1 | 0 | 0 |
| Q8VED5 | Keratin, type II cytoskeletal 79 | Krt79 | 1 | 1 | 0 | 1 | 0 | 0 | 1 | 0 | 1 |
| D3YZU1 | SH3 and multiple ankyrin repeat domains protein 1 | Shank1 | 1 | 1 | 0 | 0 | 0 | 0 | 0 | 0 | 0 |
| P0CG14 | Chromosome transmission fidelity protein 8 homolog isoform 2 | Chtf8 | 1 | 0 | 1 | 0 | 0 | 0 | 0 | 0 | 0 |
| Q91YD9 | Neural Wiskott-Aldrich syndrome protein | Wasl | 1 | 0 | 1 | 0 | 0 | 0 | 0 | 0 | 0 |
| P05213 | Tubulin alpha-1B chain | Tuba1b | 1 | 0 | 0 | 1 | 1 | 1 | 1 | 1 | 1 |
| Q3U3V8 | X-ray radiation resistance-associated protein 1 | Xrra1 | 1 | 0 | 0 | 1 | 1 | 1 | 1 | 1 | 1 |
| A2AQ07 | Tubulin beta-1 chain | Tubb1 | 1 | 0 | 0 | 1 | 1 | 1 | 0 | 1 | 0 |
| P62702 | 40S ribosomal protein S4, X isoform | Rps4x | 1 | 0 | 0 | 0 | 1 | 1 | 0 | 1 | 0 |
| P63325 | 40S ribosomal protein S10 | Rps10 | 1 | 0 | 0 | 0 | 0 | 0 | 0 | 0 | 0 |
| Q69ZU8 | Ankyrin repeat domain-containing protein 6 | Ankrd6 | 1 | 0 | 0 | 0 | 0 | 0 | 0 | 0 | 0 |
| Q6ZQ06 | Centrosomal protein of 162 kDa | Cep162 | 1 | 0 | 0 | 0 | 0 | 0 | 0 | 0 | 0 |
| Q8BJH1 | Zinc finger C2HC domain-containing protein 1A | Zc2hc1a | 1 | 0 | 0 | 0 | 0 | 0 | 0 | 0 | 0 |
| Q9JJ18 | 60S ribosomal protein L38 | Rpl38 | 1 | 0 | 0 | 0 | 0 | 0 | 0 | 0 | 0 |
| Q62415 | Apoptosis-stimulating of p53 protein 1 | Ppp1r13b | 0 | 3 | 2 | 0 | 0 | 0 | 0 | 0 | 0 |
| Q9WUM5 | Succinyl-CoA ligase subunit alpha (mitochondrial) | Suclg1 | 0 | 1 | 1 | 1 | 0 | 1 | 0 | 0 | 0 |
| P01027 | Complement C3 | C3 | 0 | 1 | 0 | 0 | 0 | 0 | 0 | 0 | 0 |
| P60710 | Actin, cytoplasmic 1 | Actb | 0 | 1 | 0 | 0 | 0 | 0 | 0 | 0 | 0 |
| Q5F2E7 | Nuclear fragile X mental retardation-interacting protein 2 | Nufip2 | 0 | 0 | 1 | 0 | 0 | 0 | 0 | 0 | 0 |

REFERENCES

Ballatore et al. 2007. Nature Reviews Neuroscience 8, 663-672. doi:10.1038/nrn2194

Belizaire et al. 2004. J. Comp. Neurol. 470, 266-281. doi:10.1002/cne.20008 Braak & Braak 1991. Acta Neuropathol 82, 239-259. doi:10.1007/BF00308809

Bragina et al. 2010. Neuroscience 165, 934-943. doi:10.1016/j.neuroscience.2009.11.009

Caffrey & Wade-Martins 2007. Neurobiol. Dis. 27, 1-10. doi:10.1016/j.nbd.2007.04.006

Calafate et al. 2015. Cell Rep 11, 1176-1183. doi:10.1016/j.celrep.2015.04.043

Crimins et al. 2012. Acta Neuropathol 124, 777-795. doi:10.1007/s00401-012-1038-9

DeKosky & Scheff 1990. Ann. Neurol. 27, 457-464. doi:10.1002/ana.410270502

Fu et al. 2017. Neuron 93, 533-541.e5. doi:10.1016/j.neuron.2016.12.023

Gallart-Palau et al. 2016. Mol Neurodegener 11, 41. doi:10.1186/s13024-016-0108-1

Hong et al. 1998. Science 282, 1914-1917. doi:10.1126/science.282.5395.1914

Hoover et al. 2010. Neuron 68, 1067-1081. doi:10.1016/j.neuron.2010.11.030

Hutton et al. 1998. Nature 393, 702-705. doi:10.1038/31508

Ittner et al. 2010. Cell 142, 387-397. doi:10.1016/j.cell.2010.06.036

Janz et al. 1999. Neuron 24, 687-700. doi:10.1016/50896-6273(00)81122-8

Kedra et al. 1998. Hum. Genet. 103, 131-141. doi:10.1007/s004390050795

Koss et al. 2016. Acta Neuropathol 132, 875-895. doi:10.1007/s00401-016-1632-3

Le Guennec et al. 2016. Molecular Psychiatry 1-7. doi:10.1038/mp.2016.226

Polydoro et al. 2014. Acta Neuropathol 127, 257-270. doi:10.1007/s00401-013-1215-5

Roberson et al. 2007. Science 316, 750-754. doi:10.1126/science.1141736

Rocher et al. 2010. Exp. Neurol. 223, 385-393. doi:10.1016/j.expneurol.2009.07.029 Sankaranarayanan & Ryan 2000. Nature Cell Biology 2, 197-204. doi:10.1038/35008615

Santacruz et al. 2005. Science 309, 476-481. doi:10.1126/science.1113694

Seabrooke et al. 2010. BMC Neurosci 11, 37. doi:10.1186/1471-2202-11-37

Spires-Jones & Hyman 2014. Neuron 82, 756-771. doi:10.1016/j.neuron.2014.05.004

Stevens et al. 2012. J. Neurosci. 32, 18054-67-18067a. doi:10.1523/JNEUROSCI.2668-12.2012

Tai et al. 2012. Am. J. Pathol. 181, 1426-1435. doi:10.1016/j.ajpath.2012.06.033

Tai et al. 2014. Acta Neuropathol Commun 2, 146. doi:10.1186/s40478-014-0146-2

Takamori et al. 2006. Cell 127, 831-846. doi:10.1016/j.cell.2006.10.030

Thompson et al. 2016. Nat Rev Neurol 12, 346-357. doi:10.1038/nrneurol.2016.68

Wang et al. 2014. Curr. Biol. 24, 2319-2326. doi:10.1016/j.cub.2014.08.027

Wang & Mandelkow 2016. Nat. Rev. Neurosci. 17, 5-21. doi:10.1038/nrn.2015.1

Wu et al. 2016. Nat. Neurosci. 19, 1085-1092. doi:10.1038/nn.4328

Yoshiyama et al. 2007. Neuron 53, 337-351. doi:10.1016/j.neuron.2007.01.010

Zhao et al. 2016. Nat. Med. 22,1268-1276. doi:10.1038/nm.4199

Zhou et al. 2017. Nature Communications 8,1-13. doi:10.1038/ncomms15295

Ahmed et al. 2013. Nat Protoc 8,998-1009. doi:10.1038/nprot.2013.053 Bekkers & Stevens 1991. Proc. Natl. Acad. Sci. U.S.A. 88,7834-7838.

Bigay et al. 2005. EMBO J. 24,2244-2253. doi:10.1038/sj.emboj.7600714

Brose et al. 1995. J. Biol. Chem. 270,25273-25280.

Burgalossi et al. 2012. Nat Protoc 7,1351-1365. doi:10.1038/nprot.2012.074

Burré et al. 2006. Proteomics 6,6250-6262. doi:10.1002/pmic.200600357

Depner et al. 2014. Nat Protoc 9,2796-2808. doi:10.1038/nprot.2014.192

DiAntonio et al. 1993. Cell 73,1281-1290.

Greenberg et al. 1992. J. Biol. Chem. 267,564-569.

Kasprowicz et al. 2014. J Cell Biol 204,1141-1156. doi:10.1083/jcb.201310090

Otvos et al. 1994. J. Neurosci. Res. 39,669-673. doi:10.1002/jnr.490390607

Piccoli et al. 2014. Mol. Cell. Biol. 34,2147-2161. doi:10.1128/MCB.00914-13

Verstreken et al. 2003. Neuron 40,733-748. doi:10.1038/nrn1315

---

The invention claimed is:

1. A method of inhibiting synaptogyrin-3 expression in a subject, the method comprising:
    determining that the subject is suffering from pathological Tau-induced presynaptic dysfunction; and
    treating the subject with a synaptogyrin-3 inhibitor selected from the group consisting of an antisense oligonucleotide, a gapmer, an siRNA, a shRNA, a CRISPR gRNA, and a nucleic acid encoding any one of the foregoing.

2. The method according to claim 1, wherein the synaptogyrin-3 inhibited by the synaptogyrin-3 inhibitor is human synaptogyrin-3.

3. The method according to claim 1, wherein the subject suffers from a disorder selected from the group consisting of Alzheimer's disease, progressive supranuclear palsy (PSP), progressive supranuclear palsy-parkinsonism (PSP-P), Richardson's syndrome, argyrophilic grain disease, corticobasal degeneration Pick's disease, frontotemporal dementia with parkinsonism associated with chromosome 17 (FTDP-17), post-encephalitic parkinsonism, Parkinson's disease complex of Guam, Guadeloupean parkinsonism, Huntington disease, Down's syndrome, dementia pugilistica, familial British dementia, familial Danish dementia, myotonic dystrophy, Hallevorden-Spatz disease, Niemann Pick type C, chronic traumatic encephalopathy, tangle-only dementia, white matter tauopathy with globular glial inclusions, subacute sclerosing panencephalitis, SLC9A6-related mental retardation, non-Guamanian motor neuron disease with neurofibrillary tangles, neurodegeneration with brain iron accumulation, Gerstmann-Sträussler-Scheinker disease, frontotemporal lobar degeneration, diffuse neurofibrillary tangles with calcification, chronic traumatic encephalopathy, amyotrophic lateral sclerosis of Guam, amyotrophic lateral sclerosis and parkinsonism-dementia complex, prion protein cerebral amyloid angiopathy, and progressive subcortical gliosis.

4. The method according to claim 1, wherein the subject suffers from a symptom selected from the group of mild cognitive impairment, dementia, cognitive decline, decline of motor function, oculomotor and bulbar dysfunction, synaptic dysfunction, neurotoxicity, neuronal degeneration, neuronal dysfunction, synapse loss, and amyloid deposition.

5. The method according to claim 4, wherein the synaptic dysfunction is pre-synaptic dysfunction.

6. A method of treating pathological Tau-induced presynaptic dysfunction, the method comprising:
    determining that the subject is suffering from pathological Tau-induced presynaptic dysfunction; and
    administering to the subject a synaptogyrin-3 inhibitor selected from the group consisting of an antisense oligonucleotide, a gapmer, an siRNA, a shRNA and a Crispr gRNA.

7. The method according to claim 6, wherein the neurons are hippocampal neurons.

8. A method of treating or inhibiting progression of a tauopathic disorder in a subject, the method comprising:
    treating the subject with a synaptogyrin-3 inhibitor selected from the group consisting of an antisense oligonucleotide, a gapmer, an siRNA, a shRNA and a CRISPR gRNA.

* * * * *